(12) United States Patent
Lacey et al.

(10) Patent No.: US 12,311,374 B2
(45) Date of Patent: *May 27, 2025

(54) CELL CULTURE VESSEL

(71) Applicant: CORNING INCORPORATED, Corning, NY (US)

(72) Inventors: William Joseph Lacey, North Andover, MA (US); Gregory Roger Martin, Acton, ME (US); Ana Maria del Pilar Pardo, Portsmouth, NH (US); Allison Jean Tanner, Portsmouth, NH (US)

(73) Assignee: CORNING INCORPORATED, Corning, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/525,119

(22) Filed: Nov. 30, 2023

(65) Prior Publication Data
US 2024/0091778 A1 Mar. 21, 2024

Related U.S. Application Data

(62) Division of application No. 16/628,474, filed as application No. PCT/US2018/042133 on Jul. 13, 2018, now Pat. No. 11,857,970.

(Continued)

(51) Int. Cl.
*B01L 3/00* (2006.01)
*C12M 1/00* (2006.01)
*C12M 1/24* (2006.01)

(52) U.S. Cl.
CPC .......... *B01L 3/5085* (2013.01); *C12M 23/08* (2013.01); *C12M 23/38* (2013.01); *B01L 2300/0858* (2013.01)

(58) Field of Classification Search
None
See application file for complete search history.

(56) References Cited

U.S. PATENT DOCUMENTS 2,947,116 A 8/1960 Wilton et al.
3,630,849 A 12/1971 David et al.
(Continued)

FOREIGN PATENT DOCUMENTS

AU 2004256209 A1 1/2005
CA 2558946 A1 1/2005
(Continued)

OTHER PUBLICATIONS

Song et al., Sinusoidal wavy surfaces for curvature-guided migration of T lymphocytes, 2015, Biomaterials, 51, pp. 151-160 (Year: 2016).*

(Continued)

*Primary Examiner* — Holly Kipouros
(74) *Attorney, Agent, or Firm* — Chandra J. Duncan

(57) ABSTRACT

A cell culture vessel has a wall and cell culture surface having a plurality of microcavities for culturing cells in three-dimensional conformation, referred to as "spheroids". The inner surface of the wall and the cell culture surface define a cell culture chamber of the vessel. The wall is attached to the cell culture surface in a way that does not provide flat surfaces on or around the cell culture surface so that the vessel provides an environment suitable for the production of a homogeneous population of three-dimensional cell clusters, or spheroids.

10 Claims, 24 Drawing Sheets

Related U.S. Application Data

(60) Provisional application No. 62/642,427, filed on Mar. 13, 2018, provisional application No. 62/532,648, filed on Jul. 14, 2017, provisional application No. 62/532,681, filed on Jul. 14, 2017, provisional application No. 62/532,639, filed on Jul. 14, 2017, provisional application No. 62/532,671, filed on Jul. 14, 2017.

(56) References Cited

U.S. PATENT DOCUMENTS

| | | |
|---|---|---|
| 4,382,685 A | 5/1983 | Pearson |
| 4,461,836 A | 7/1984 | Von Froreich |
| 4,498,785 A | 2/1985 | De Bruyne |
| 4,534,656 A | 8/1985 | De Bruyne |
| 4,670,396 A | 6/1987 | Bear et al. |
| 4,760,028 A | 7/1988 | De Bruyne et al. |
| 4,927,764 A | 5/1990 | Lyman et al. |
| 4,980,293 A | 12/1990 | Jeffs |
| 5,047,347 A | 9/1991 | Cline |
| 5,151,366 A | 9/1992 | Serkes et al. |
| 5,171,994 A | 12/1992 | Bahraman |
| 5,171,995 A | 12/1992 | Gast et al. |
| 5,240,854 A | 8/1993 | Berry et al. |
| 5,272,084 A | 12/1993 | O'Connell et al. |
| 5,319,436 A | 6/1994 | Manns et al. |
| 5,374,557 A | 12/1994 | Verma |
| 5,398,837 A | 3/1995 | Degrassi |
| 5,487,872 A | 1/1996 | Hafeman et al. |
| 5,554,536 A | 9/1996 | Rising |
| 5,587,321 A | 12/1996 | Smith et al. |
| 5,598,262 A | 1/1997 | Jutard et al. |
| 5,665,562 A | 9/1997 | Cook |
| 5,693,537 A | 12/1997 | Wilson et al. |
| 5,707,869 A | 1/1998 | Wolf et al. |
| 5,710,043 A | 1/1998 | Pay |
| 5,736,397 A | 4/1998 | Garcia et al. |
| 5,759,494 A | 6/1998 | Szlosek |
| 5,766,949 A | 6/1998 | Liau et al. |
| 5,772,905 A | 6/1998 | Chou |
| 5,783,440 A | 7/1998 | Stevens |
| 5,792,653 A | 8/1998 | Weibezahn et al. |
| 5,858,309 A | 1/1999 | Mathus et al. |
| 5,972,694 A | 10/1999 | Mathus |
| 6,030,829 A | 2/2000 | Dannoux et al. |
| 6,039,972 A | 3/2000 | Barlow et al. |
| 6,306,646 B1 | 10/2001 | Saad et al. |
| 6,348,999 B1 | 2/2002 | Summersgill et al. |
| 6,514,464 B1 | 2/2003 | Knebel |
| 6,521,451 B2 | 2/2003 | Potter |
| 6,567,675 B1 | 5/2003 | Rosen et al. |
| 6,767,607 B2 | 7/2004 | Tanner et al. |
| 6,811,752 B2 | 11/2004 | Barbera-Guillem |
| 6,908,767 B2 | 6/2005 | Bader |
| 6,987,019 B1 | 1/2006 | Rogalsky |
| 7,470,424 B2 | 12/2008 | Kataoka et al. |
| 7,547,547 B2 | 6/2009 | Dang et al. |
| 7,674,346 B2 | 3/2010 | Clements et al. |
| 7,687,262 B2 | 3/2010 | Cattadoris |
| 7,691,369 B2 | 4/2010 | Kataoka et al. |
| 7,727,759 B2 | 6/2010 | Ozawa et al. |
| 7,745,209 B2 | 6/2010 | Martin et al. |
| 7,745,210 B2 | 6/2010 | Martin |
| 7,800,749 B2 | 9/2010 | Leblanc et al. |
| 7,897,379 B2 | 3/2011 | Kenney et al. |
| 7,919,319 B2 | 4/2011 | Jervis et al. |
| 8,053,230 B2 | 11/2011 | Whittlinger |
| 8,143,053 B2 | 3/2012 | Yerbic |
| 8,148,152 B2 | 4/2012 | Kolossov et al. |
| 8,158,426 B2 | 4/2012 | Wilson et al. |
| 8,158,427 B2 | 4/2012 | Wilson et al. |
| 8,163,537 B2 | 4/2012 | Martin et al. |
| 8,168,432 B2 | 5/2012 | Wilson et al. |
| 8,178,345 B2 | 5/2012 | Bennett et al. |
| 8,273,572 B2 | 9/2012 | Martin et al. |
| 8,318,479 B2 | 11/2012 | Domansky et al. |
| 8,415,144 B2 | 4/2013 | Wilson et al. |
| 8,470,589 B2 | 6/2013 | Martin et al. |
| D685,497 S | 7/2013 | Kenney et al. |
| 8,486,692 B2 | 7/2013 | Simon |
| 8,597,597 B2 | 12/2013 | Deutsch et al. |
| 8,617,879 B2 | 12/2013 | Yu et al. |
| 8,697,443 B2 | 4/2014 | Wilson et al. |
| 8,759,017 B2 | 6/2014 | Owen et al. |
| 8,778,669 B2 | 7/2014 | Lacey et al. |
| 8,846,399 B2 | 9/2014 | Martin et al. |
| 8,906,685 B2 | 12/2014 | Takayama et al. |
| 8,932,544 B2 | 1/2015 | Mueller et al. |
| 9,039,883 B2 | 5/2015 | Guerrieri et al. |
| 9,040,293 B2 | 5/2015 | Gulzow et al. |
| 9,045,721 B2 | 6/2015 | Martin et al. |
| 9,068,281 B2 | 6/2015 | Wu et al. |
| 9,126,199 B2 | 9/2015 | Moritz et al. |
| 9,169,460 B2 | 10/2015 | Cecchi |
| D748,812 S | 2/2016 | Kenney et al. |
| 9,260,684 B1 | 2/2016 | Egeler et al. |
| 9,260,695 B2 | 2/2016 | Crowley et al. |
| 9,389,187 B2 | 7/2016 | Furnas |
| 9,436,990 B2 | 9/2016 | Otani et al. |
| 9,493,733 B2 | 11/2016 | Giles |
| 9,494,577 B2 | 11/2016 | McGarr et al. |
| 9,573,128 B1 | 2/2017 | McClelland |
| 9,587,213 B2 | 3/2017 | Morgan et al. |
| 9,636,680 B2 | 5/2017 | Fattinger et al. |
| 9,732,317 B2 | 8/2017 | Wilson |
| 9,790,465 B2 | 10/2017 | Bennett et al. |
| 9,845,451 B2 | 12/2017 | Martin et al. |
| 9,862,918 B2 | 1/2018 | Ito |
| 9,933,373 B2 | 4/2018 | Vild et al. |
| 10,067,065 B1 | 9/2018 | Alam et al. |
| 10,254,274 B2 | 4/2019 | Miklas et al. |
| 11,345,880 B2 | 5/2022 | Goral |
| 11,441,121 B2 | 9/2022 | Bennett et al. |
| 11,613,722 B2 | 3/2023 | Martin et al. |
| 2002/0022219 A1 | 2/2002 | Clements et al. |
| 2002/0172621 A1 | 11/2002 | Barbera-Guillem |
| 2003/0031829 A1 | 2/2003 | Tanner et al. |
| 2003/0104494 A1 | 6/2003 | Ravkin et al. |
| 2003/0183958 A1 | 10/2003 | Goff et al. |
| 2003/0186217 A1 | 10/2003 | Bader |
| 2003/0205511 A1 | 11/2003 | Olivier et al. |
| 2003/0215941 A1 | 11/2003 | Campbell et al. |
| 2004/0091397 A1 | 5/2004 | Picard |
| 2004/0101955 A1 | 5/2004 | Whitley |
| 2004/0125266 A1 | 7/2004 | Miyauchi et al. |
| 2004/0216835 A1 | 11/2004 | Tanner et al. |
| 2004/0259242 A1 | 12/2004 | Malinge et al. |
| 2004/0259423 A1 | 12/2004 | Elbaz et al. |
| 2005/0032208 A1 | 2/2005 | Oh et al. |
| 2005/0047971 A1 | 3/2005 | Clements et al. |
| 2005/0074873 A1 | 4/2005 | Shanler et al. |
| 2005/0112030 A1 | 5/2005 | Gaus |
| 2005/0116717 A1 | 6/2005 | Dransfield et al. |
| 2005/0147959 A1 | 7/2005 | Frondoza et al. |
| 2006/0110822 A1 | 5/2006 | Robbins et al. |
| 2006/0234370 A1 | 10/2006 | Korpinen et al. |
| 2006/0252044 A1 | 11/2006 | Okumura et al. |
| 2006/0292654 A1 | 12/2006 | Reardon |
| 2007/0178441 A1 | 8/2007 | Li |
| 2007/0216897 A1 | 9/2007 | Sonda |
| 2008/0003671 A1 | 1/2008 | Martin |
| 2008/0009027 A1 | 1/2008 | Fraker et al. |
| 2008/0118974 A1 | 5/2008 | Martin et al. |
| 2008/0206857 A1 | 8/2008 | Kenney et al. |
| 2008/0268515 A1 | 10/2008 | Cullimore et al. |
| 2008/0297784 A1 | 12/2008 | Leblanc et al. |
| 2008/0299649 A1 | 12/2008 | Martin et al. |
| 2008/0300278 A1 | 12/2008 | Torrens et al. |
| 2009/0017540 A1 | 1/2009 | Nishio et al. |
| 2009/0018033 A1 | 1/2009 | Morgan et al. |
| 2009/0029462 A1 | 1/2009 | Beardsley et al. |
| 2009/0037293 A1 | 2/2009 | Unger et al. |
| 2009/0170190 A1 | 7/2009 | Nishi et al. |

(56) References Cited

U.S. PATENT DOCUMENTS

| | | |
|---|---|---|
| 2009/0191620 A1 | 7/2009 | Martin et al. |
| 2009/0288963 A1 | 11/2009 | Guerrieri et al. |
| 2009/0298164 A1 | 12/2009 | Cattadoris et al. |
| 2009/0298166 A1 | 12/2009 | Fang et al. |
| 2010/0055774 A1 | 3/2010 | Wilson |
| 2010/0068793 A1 | 3/2010 | Ungrin et al. |
| 2010/0074515 A1 | 3/2010 | Zhao et al. |
| 2010/0093075 A1 | 4/2010 | Mueller |
| 2010/0112014 A1 | 5/2010 | Gilbert et al. |
| 2010/0112684 A1 | 5/2010 | Lee et al. |
| 2010/0119418 A1 | 5/2010 | Clements et al. |
| 2010/0170790 A1 | 7/2010 | Takahashi et al. |
| 2010/0190197 A1 | 7/2010 | Martin et al. |
| 2010/0197013 A1 | 8/2010 | Kamp et al. |
| 2010/0247386 A1 | 9/2010 | Deutsch et al. |
| 2010/0273258 A1 | 10/2010 | Lannutti et al. |
| 2010/0296084 A1 | 11/2010 | Berg et al. |
| 2010/0297600 A1 | 11/2010 | Cecchi |
| 2011/0086375 A1 | 4/2011 | Ungrin et al. |
| 2011/0097790 A1 | 4/2011 | Yerbic |
| 2011/0104730 A1 | 5/2011 | Larsen et al. |
| 2011/0129923 A1 | 6/2011 | Wilson et al. |
| 2011/0229961 A1 | 9/2011 | Higashi et al. |
| 2012/0064627 A1 | 3/2012 | Khine et al. |
| 2012/0129208 A1 | 5/2012 | Khine et al. |
| 2012/0129257 A1 | 5/2012 | Yu et al. |
| 2012/0219572 A1 | 8/2012 | Prockop et al. |
| 2013/0052331 A1 | 2/2013 | Kram et al. |
| 2013/0122539 A1 | 5/2013 | Li et al. |
| 2013/0122580 A1 | 5/2013 | Tsukada et al. |
| 2013/0143254 A1 | 6/2013 | Thomas et al. |
| 2013/0164848 A1 | 6/2013 | Munaka et al. |
| 2013/0203159 A1 | 8/2013 | Itoh et al. |
| 2013/0344598 A1 | 12/2013 | Nistor |
| 2014/0004086 A1 | 1/2014 | Peak |
| 2014/0027784 A1 | 1/2014 | Wada et al. |
| 2014/0099717 A1 | 4/2014 | Fraker et al. |
| 2014/0106394 A1 | 4/2014 | Ko et al. |
| 2014/0106452 A1 | 4/2014 | Vukasinovic |
| 2014/0120573 A1 | 5/2014 | Tavana et al. |
| 2014/0178992 A1 | 6/2014 | Nakashima et al. |
| 2014/0221225 A1 | 8/2014 | Danen et al. |
| 2014/0226004 A1 | 8/2014 | Son et al. |
| 2014/0227784 A1 | 8/2014 | Ejiri et al. |
| 2014/0240489 A1 | 8/2014 | Furnas |
| 2014/0315296 A1 | 10/2014 | Wilson |
| 2014/0322806 A1 | 10/2014 | Bennett et al. |
| 2015/0004686 A1 | 1/2015 | Goral et al. |
| 2015/0064738 A1 | 3/2015 | Tsukada et al. |
| 2015/0072405 A1 | 3/2015 | Ito |
| 2015/0184119 A1 | 7/2015 | Tsukada et al. |
| 2015/0247112 A1 | 9/2015 | Orr et al. |
| 2016/0003796 A1 | 1/2016 | Kranbuehl |
| 2016/0017267 A1 | 1/2016 | Hansen et al. |
| 2016/0040120 A1 | 2/2016 | Gottwald et al. |
| 2016/0137962 A1 | 5/2016 | Ejiri et al. |
| 2016/0194588 A1 | 7/2016 | Guenat et al. |
| 2016/0216250 A1 | 7/2016 | Ritter et al. |
| 2016/0250631 A1 | 9/2016 | Kang et al. |
| 2017/0067009 A1 | 3/2017 | Sloane et al. |
| 2017/0067019 A1 | 3/2017 | Ho |
| 2017/0073625 A1 | 3/2017 | Kasuto et al. |
| 2017/0226455 A1 | 8/2017 | Fang et al. |
| 2017/0226458 A1 | 8/2017 | Li et al. |
| 2017/0267959 A1 | 9/2017 | Martin et al. |
| 2017/0283757 A1 | 10/2017 | Carter et al. |
| 2017/0306281 A1 | 10/2017 | Martin et al. |
| 2017/0342363 A1 | 11/2017 | Fang et al. |
| 2018/0166743 A1 | 6/2018 | Lee et al. |
| 2018/0201888 A1 | 7/2018 | Miwa et al. |
| 2018/0301754 A1 | 10/2018 | Badding et al. |
| 2019/0006707 A1 | 1/2019 | Sakamoto et al. |
| 2020/0064197 A1 | 2/2020 | Furnas |
| 2020/0131461 A1 | 4/2020 | Martin et al. |
| 2020/0179923 A1 | 6/2020 | Lacey et al. |
| 2020/0181552 A1 | 6/2020 | Martin et al. |
| 2020/0199006 A1 | 6/2020 | Jain et al. |
| 2020/0239854 A1 | 7/2020 | Ayano et al. |
| 2021/0062126 A1 | 3/2021 | Martin et al. |
| 2022/0220434 A1 | 7/2022 | Martin et al. |
| 2022/0259540 A1 | 8/2022 | Li et al. |

FOREIGN PATENT DOCUMENTS

| | | |
|---|---|---|
| CA | 2679011 A1 | 9/2008 |
| CA | 2848875 A1 | 3/2013 |
| CN | 2186755 Y | 1/1995 |
| CN | 1168921 A | 12/1997 |
| CN | 1234112 A | 11/1999 |
| CN | 1867663 A | 11/2006 |
| CN | 1875093 A | 12/2006 |
| CN | 201261785 Y | 6/2009 |
| CN | 201626959 U | 11/2010 |
| CN | 101978041 A | 2/2011 |
| CN | 102105578 A | 6/2011 |
| CN | 102257123 A | 11/2011 |
| CN | 102449135 A | 5/2012 |
| CN | 102687023 A | 9/2012 |
| CN | 202450098 U | 9/2012 |
| CN | 202849407 U | 4/2013 |
| CN | 103080294 A | 5/2013 |
| CN | 103119151 A | 5/2013 |
| CN | 203513696 U | 4/2014 |
| CN | 103814125 A | 5/2014 |
| CN | 204608026 U | 9/2015 |
| CN | 204702760 U | 10/2015 |
| CN | 204714819 U | 10/2015 |
| CN | 204752742 U | 11/2015 |
| CN | 204803327 U | 11/2015 |
| CN | 205170866 U | 4/2016 |
| CN | 205669029 U | 11/2016 |
| CN | 205839030 U | 12/2016 |
| CN | 205990396 U | 3/2017 |
| CN | 107109340 A | 8/2017 |
| CN | 107109341 A | 8/2017 |
| CN | 107208025 A | 9/2017 |
| CN | 107460125 A | 12/2017 |
| DE | 3116926 A1 | 11/1982 |
| DE | 8309876 U1 | 12/1983 |
| DE | 10019862 A1 | 11/2001 |
| DE | 202006017853 U1 | 1/2007 |
| DE | 102009005526 A1 | 7/2010 |
| DE | 102014214077 A1 | 1/2016 |
| DE | 102014017728 A1 | 6/2016 |
| DE | 102015116732 A1 | 4/2017 |
| EP | 0307048 A2 | 3/1989 |
| EP | 0605527 A1 | 7/1994 |
| EP | 0681846 A2 | 11/1995 |
| EP | 0800571 A2 | 10/1997 |
| EP | 0834552 A1 | 4/1998 |
| EP | 0965633 A1 | 12/1999 |
| EP | 1181349 A1 | 2/2002 |
| EP | 1348533 A2 | 10/2003 |
| EP | 1358937 A1 | 11/2003 |
| EP | 1445022 A2 | 8/2004 |
| EP | 1988152 A1 | 11/2008 |
| EP | 2032262 A2 | 3/2009 |
| EP | 2085463 A1 | 8/2009 |
| EP | 2617807 A1 | 7/2013 |
| EP | 2653531 A1 | 10/2013 |
| EP | 2759592 A1 | 7/2014 |
| EP | 2896684 A1 | 7/2015 |
| EP | 3081627 A1 | 10/2016 |
| EP | 3296018 A1 | 3/2018 |
| EP | 3351615 A1 | 7/2018 |
| EP | 3372666 A1 | 9/2018 |
| GB | 2147100 A | 5/1985 |
| JP | 03-139350 A | 6/1991 |
| JP | 06-038734 A | 2/1994 |
| JP | 06-327462 A | 11/1994 |
| JP | 09-173049 A | 7/1997 |
| JP | 09-234811 A | 9/1997 |
| JP | 10-210866 A | 8/1998 |
| JP | 10-210966 A | 8/1998 |

(56) References Cited

FOREIGN PATENT DOCUMENTS

| | | |
|---|---|---|
| JP | 2001-106749 A | 4/2001 |
| JP | 2003-135056 A | 5/2003 |
| JP | 2003-180335 A | 7/2003 |
| JP | 2004-129558 A | 4/2004 |
| JP | 2004-535829 A | 12/2004 |
| JP | 2005-080660 A | 3/2005 |
| JP | 2006-121991 A | 5/2006 |
| JP | 2006-191809 A | 7/2006 |
| JP | 2007-510429 A | 4/2007 |
| JP | 3139350 U | 2/2008 |
| JP | 2009-017810 A | 1/2009 |
| JP | 2009-050194 A | 3/2009 |
| JP | 2009-183288 A | 8/2009 |
| JP | 2009-542230 A | 12/2009 |
| JP | 2010-088347 A | 4/2010 |
| JP | 2010-104327 A | 5/2010 |
| JP | 2010-518879 A | 6/2010 |
| JP | 2010-158214 A | 7/2010 |
| JP | 2011-509686 A | 3/2011 |
| JP | 2011-521642 A | 7/2011 |
| JP | 2011-172533 A | 9/2011 |
| JP | 2011-528226 A | 11/2011 |
| JP | 2012-249547 A | 12/2012 |
| JP | 2013-055911 A | 3/2013 |
| JP | 2014-132869 A | 7/2014 |
| JP | 2015-012827 A | 1/2015 |
| JP | 2015-029431 A | 2/2015 |
| JP | 2015-073520 A | 4/2015 |
| JP | 2016-002023 A | 1/2016 |
| JP | 5845185 B2 | 1/2016 |
| JP | 2016-093149 A | 5/2016 |
| JP | 2016-136920 A | 8/2016 |
| JP | 2016-136921 A | 8/2016 |
| JP | 2017-532970 A | 11/2017 |
| JP | 2018-108032 A | 7/2018 |
| KR | 10-2014-0113319 A | 9/2014 |
| KR | 10-2014-0125662 A | 10/2014 |
| KR | 10-2017-0008539 A | 1/2017 |
| KR | 10-2460969 B1 | 10/2022 |
| WO | 92/07063 A2 | 4/1992 |
| WO | 93/07258 A1 | 4/1993 |
| WO | 96/21851 A2 | 7/1996 |
| WO | 98/15355 A2 | 4/1998 |
| WO | 98/31466 A1 | 7/1998 |
| WO | 01/80997 A1 | 11/2001 |
| WO | 01/92462 A1 | 12/2001 |
| WO | 2004/044120 A2 | 5/2004 |
| WO | 2004/094060 A1 | 11/2004 |
| WO | 2005/047464 A2 | 5/2005 |
| WO | 2006/043267 A1 | 4/2006 |
| WO | 2007/015770 A1 | 2/2007 |
| WO | 2007/097120 A1 | 8/2007 |
| WO | 2008/006104 A2 | 1/2008 |
| WO | 2008/008149 A2 | 1/2008 |
| WO | 2008/106771 A1 | 9/2008 |
| WO | 2008/118500 A1 | 10/2008 |
| WO | 2008/140295 A1 | 11/2008 |
| WO | 2008/149039 A2 | 12/2008 |
| WO | 2008/153783 A1 | 12/2008 |
| WO | 2009/094125 A2 | 7/2009 |
| WO | 2009/148509 A1 | 12/2009 |
| WO | 2009/148512 A2 | 12/2009 |
| WO | 2010/008566 A2 | 1/2010 |
| WO | 2010/042072 A1 | 4/2010 |
| WO | 2010/069589 A1 | 6/2010 |
| WO | 2012/036011 A1 | 3/2012 |
| WO | 2012/077683 A1 | 6/2012 |
| WO | 2012/170232 A1 | 12/2012 |
| WO | 2013/042360 A1 | 3/2013 |
| WO | 2013/108293 A1 | 7/2013 |
| WO | 2013/116449 A1 | 8/2013 |
| WO | 2014/042162 A1 | 3/2014 |
| WO | 2014/072432 A1 | 5/2014 |
| WO | 2014/140181 A1 | 9/2014 |
| WO | 2014/156455 A1 | 10/2014 |
| WO | 2014/165273 A1 | 10/2014 |
| WO | 2014/171782 A1 | 10/2014 |
| WO | 2014/179196 A1 | 11/2014 |
| WO | 2014/196204 A1 | 12/2014 |
| WO | 2015/033507 A1 | 3/2015 |
| WO | 2015/061907 A1 | 5/2015 |
| WO | 2015/087369 A1 | 6/2015 |
| WO | 2016/020992 A1 | 2/2016 |
| WO | 2016/064757 A1 | 4/2016 |
| WO | 2016/069885 A1 | 5/2016 |
| WO | 2016/069892 A1 | 5/2016 |
| WO | 2016/069895 A1 | 5/2016 |
| WO | 2016/069917 A1 | 5/2016 |
| WO | 2016/069930 A1 | 5/2016 |
| WO | 2016/157322 A1 | 10/2016 |
| WO | 2017/025584 A1 | 2/2017 |
| WO | 2017/047735 A1 | 3/2017 |
| WO | 2017/077163 A1 | 5/2017 |
| WO | 2017/142410 A1 | 8/2017 |
| WO | 2018/068034 A1 | 4/2018 |
| WO | 2018/200893 A1 | 11/2018 |
| WO | 2019/010401 A1 | 1/2019 |
| WO | 2019/014621 A1 | 1/2019 |
| WO | 2019/014627 A1 | 1/2019 |
| WO | 2019/014635 A1 | 1/2019 |
| WO | 2019/014636 A1 | 1/2019 |
| WO | 2019/178039 A1 | 9/2019 |

OTHER PUBLICATIONS

"Identification grid for microplates", Rtreived from: https://www.kisker-biotech.com/frontoffice/product?produitId=0N-27-11, 2 pages, 2021.

"Laboratory Flasks Selection Guide: Types, Features, Applications", Engineering360, <https://www.globalspec.com/learnmore/labware_scientific_instruments/labware_consumables/laboratory_flasks#:~:text=Laboratory%20flasks%20are%20lab%20vessels,the%20opening%20at%20the%20neck.> accessed Apr. 8, 2022 (Year: 2022).

Achilli et al, "Advances in the Formation, Use and Understanding of Multi-Cellular Spheroids", Expert Opin. Biol. Ther. (2012) 12(10):1347-1360.

Alepee et al, "State-Of-The-Art 3D Cultures (Organs-On-A-Chip) in Safety Testing and Pathophysiology"; Transatlantic Think Tank for Toxicology, T4 Workshop Report, Altex 31, 4/14, pp. 441-477, Retrieved From: http://dx.doi.org/10.14573/altex1406111 (Jul. 14, 2014).

Aline, "We Engineer Microfluidic Products" ; 7 Pages; (2020) https://alineinc.com/.

Anada et al; "An Oxygen-Permeable Spheroid Culture System for the Prevention of Central Hypoxia and Necrosis of Spheroids"; Biomaterials, 33, (2012) 8430-8441.

AxoSIM, Nerve-On-A-Chip Mini-Brain About Team; 6 Pages; (Downloaded Mar. 9, 2020); http://axosim.com/.

AxoSIM, NerveSim BrianSim About Resources; Available on (http://axosim.com/), Accessed May 13, 2021, 6 Pages.

Bartosh et al; "Aggregation of Human Mesenchymal Stromal Cells (MSCS) Into 3D Spheroid Enhances Their AntiInflammatory Properties"; PNAS, Aug. 3, 2010, vol. 107, No. 31 pp. 13724-13729.

BioIVT Elevating Science(Registered); 6 Pages; (2020); http://www.hepregen.com/.

BioIVT Elevating Science, HEPATOPAC® Technology, Available at (https://bioivt.com/about/technologies/hepatopactechnology), Accessed May 13, 2021, 3 Pages.

Brandrup et al., "Polymer Handbook", Fourth Edition, Wiley-Interscience Publication, , Permeability and diffusion data, 1999, 9 pages (Contributors; Preface).

Carver et al; Multicellular Tumor Spheroids as a Model for Assessing Delivery of Oligonucleotides in Three Dimensions; Molecular Therapy-Nucleic Acids (2014) 3, E153; 8 Pages.

Chen et al., "Microfluidic array for three-dimensional perfusion culture of human mammary epithelial cells." Biomed Microdevices, vol. 13 (2011), pp. 753-758.

(56) References Cited

OTHER PUBLICATIONS

Cheng et al., "MicroRNA-34a Targets Forkhead Box J2 to Modulate Differentiation of Endothelial Progenitor Cells in Response to Shear Stress", J Mol Cell Cardiol. 74 (2014) 4-12.

Choi et al., "Feasibility of a simple double-layered coculture system incorporating metabolic processes of the intestine and liver tissue: application to the analysis of benzo[a]pyrene toxicity" Toxicology in Vitro, vol. 18, pp. 393-402, 2004.

CN-Bio, "Transforming Drug Discovery and the Lives of Patients"; 5 Pages; (2020) http://cn-bio.com/.

Colazzo et al., "Shear Stress and VEGF Enhance Endothelial Differentiation of Human Adipose-Derived Stem Cells", Growth Factors, 2014, 32(5):139-149.

Corning Life Sciences Product Portfolio; 5 Pages Saved Mar. 6, 2020.

Corning(Registered) HTS Transwell(Registered)-96 Tissue Culture Systems, Permeable Supports for High Throughput Screening Applications; 2 Pages (2004).

Curcio et al. "Mass transfer and metabolic reactions in hepatocyte spheroids cultured in rotating wall gas-permeable membrane system." Biomaterials 28 (2007) 5487-5497. (Year: 2007).

Document entitled Description EP2653531A1, machine translation of EP 2653531 A1 (original document already made of record by Applicant) provided by Proquest, original document published 2013 (Year: 2013).

Dolznig et al, "Organotypic spheroid cultures to study tumor-stroma interaction during cancer development", Drug Discovery Today: Disease Models, 2011, 8(2-3):113-118.

Domansky et al, "Perfused Multiwell Plate for 3D Liver Tissue Engineering", Lab Chip, 2010, 10:51-58.

ElveFlow; "Microfluidics Innovation Center"; 6 Pages; (Downloaded Mar. 9, 2020); https://www.elveflow.com.

Emulate, 6 Pages; (2019) https://emulatebio.com/.

Endo et al., "Gene transfection to spheroid culture system on micropatterned culture plate by polyplex nanomicelle: a novel platform of genetically-modified cell transplantation", Drug Deliv. and Transl. Res., 2012, vol. 2, p. 398-405.

Engelberg et al, "Essential operating principles for tumor spheroid growth", BMC Systems Biology 2008, 2:110, 19 pages.

English language machine translation of JP06327462 (Nov. 29, 1994).

English language machine translation of JP2009050194 (Mar. 12, 2009).

Evenou et al. "Spontaneous Formation of Highly Functional Three-Dimensional Multilayer from Human Hepatoma Hep G2 Cells Cultured on an Oxygen-Permeable Polydimethylsiloxane Membrane." Tissue Engineering: Part C vol. 16, No. 2, 2010, pp. 311-318. (Year: 2010).

Friedrich et al. "Spheroid—based drug screen: considerations and practical approach." Nature protocols, 2009, vol. 4 No. 3, 309-323.

Friedrich et al: "Experimental anti-tumor therapy in 3-D: spheroids—old hat or new challenge?" Int J Radiat Biol 2007, 83:849-871.

Frith et al. "Dynamic three-dimensional culture methods enhance mesenchymal stem cell properties and increase therapeutic potential." Tissue engineering, 2010, 16, No. 4, 735-749.

Fukuda et al, "Efficacy of a polyurethane foam/spheroid artificial liver by using human hepaloblastoma cell line (Hep G2)", Cell Transplantation, 2003, 12:51-58.

G-Plate: Accelerate your cell cultures to the next dimension, "An original cell culture model allowing for inland shaped 3D cell aggregates" 1 page, retrieved Sep. 8, 2015.

GeoChem Incorporated, Product Line; hllps://www.geocheminc.com, 4 Pages; (2020).

Hμrel (Registered) Corporation, Bioanalytic Tools Company; 2 Pages; (2013); http://hurelcorp.com/.

Haycock, "3D cell culture: a review of current approaches and techniques", Methods Mol Biol, 2011; 695:1-15.

Hirschhaeuser et al., "Multicellular tumor spheroids: An underestimated tool is catching up again." Journal of Biotechnology, 2010, 148, 3-15.

Howes et al; "3-Dimensional Culture Systems for Anit-Cancer Compound Profiling and High-Throughput Screening Reveal Increases in EGFR Inhibitor-Mediated Cytotoxicity Compared to Monolayer Culture Systems"; PLOS One; Sep. 2004, vol. 9, Issue 9, 11 Pages.

Hribar et al; "Nonlinear 3D Projection Printing of Concave Hydrogel Microstructures for Long-Term Multicellular Spheroid and Embryoid Body Culture"; Lab Chip, 2015, 15, 2412-2418.

Hsiao et al., "Effects of 3D Microwell Culture on Initial Fate Specification in Human Embryonic Stem Cells", Published in final edited form as AIChE J. vol. 60 No. 4, Apr. 2014, pp. 1225-1235.

Huang et al., "Preparation of dense Ta-LLZO/MgO composite Li-ion solid electrolyte: Sintering, microstructure, performance and the role of MgO", Journal of Energy Chemistry, vol. 39, 2019, pp. 8-16.

Hwang et al; "Microwell-Mediated Control of Embryoid Body Size Regulates Embryonic Stem Cell Fate via Differential Expression of WNT5A and WNT11"; PNAS; Oct. 6, 2009, vol. 106, No. 40, pp. 16978-16983.

Jeon et al, "Combined Effects of Flow-Induced Shear Stress and Micropatterned Surface Morphology on Neuronal Differentiation of Human Mesenchymal Stem Cells" J Biosci Bioeng, 2014, 117(2):242-247.

Jiang et al, "Shear Enhances Thrombopoiesis and Formation of Microparticles That Induce Megakaryocytic Differentiation of Stem Cells", Blood, Sep. 25, 2014; 124(13):2094-2103.

Junji Fukuda et al., "Hepatocyte Spheroid Arrays Inside Microwells Connected With Microchannels", Biomicrofluidics 5, 2011, pp. 10.

Kelm et al, "Method for generation of homogeneous multicellular tumor spheroids applicable to a wide variety of cell types", Biotechnology and Bioengineering 2003; 83(2):173-180.

Kim et al, "Shear Stress Induced by an Interstitial Level of Slow Flow Increases the Osteogenic Differentiation of Mesenchymal Stem Cells Through TAZ Activation" PLoS ONE, Mar. 21, 2014; 9(3), e92427, 9 pages.

Urich et al, "Multicellular Self-Assembled Spheroidal Model of the Blood Brain Barrier"; Scientific Reports, 3, 1500, 8 Pages.

Vinci et al. Advances in establishment and analysis of three-dimensional tumor spheroid-based functional assays for target validation and drug evaluation, BMC Biology 2012, 10:29.

Weegman et al, "Nutrient Regulation by Continuous Feeding Removes Limitations on Cell Yield in the Large-Scale Expansion of Mammalian Cell Spheroids"; PLOS ONE, 2013, vol. 8, Issue 10, e76611, 10 Pages.

Wikipedia, "Antiroll Tanks"; 3 Pages; Page Last Edited May 23, 2019.

WO 2017/077163 (Year: 2017).

WO-2008149039 translation (Year: 2008).

Wrighton et al, "Forces of Change: Mechanics Underlying Formation of Functional 3D Organ Buds" Cell Stem Cell, May 7, 2015; 16(5): 453-454.

Xu et al, "Characterisation of some cytotoxic endpoints using rat liver and HepG2 spheroids as in vitro models and their application in hepatotoxicity studies. I. Glucose metabolism and enzyme release as cytotoxic markers." Toxicol Appl Pharmacol 2003;189:100-111.

Yamada et al, "Efficient induction of hepatocyte spheroids in a suspension culture using a water-soluble synthetic polymer as an artificial matrix." J Biochem 1998; 123:1017-1023.

Yang et al.,"An Agarose-Gel Based Method for Transporting Cell Lines", Current Chemical Genomics, vol. 3, Jan. 2009, pp. 50-53.

Zuidema et al., "Fabrication and Characterization of Tunable Polysaccharide Hydrogel Blends for Neural Repair", Acta Biomaterialia, vol. 7, No. 4, Apr. 2011, pp. 1634-1643.

Koide et al, "Formation of multicellular spheroids composed of adult rat hepatocytes in dishes with positively charged surfaces and under other nonadherent environments", Exp Cell Res 1990; 186:227-235.

Koike et al. "Characterization of Embryo id Bodies of Mouse Embryonic Stem Cells Formed under Various Culture Conditions and Estimation of Differentiation Status of Such Bodies." Journal of Bioscience and Bioengineering vol. I 04, No. 4, 294-299. 2007. (Year: 2007).

(56) References Cited

OTHER PUBLICATIONS

Kunz-Schughart et al, "The use of 3-D cultures for high-throughput screening: the multicellular spheroid model", J Biomol Screen 2004, 9(4):273-285.
Kutsuzawa et al, "Highly Robust Protein Production by Co-Culture of CHO Spheroids Layered on Feeder Cells in Serum-Free Medium"; Colloid Polym Sci (2014) 292; 839-848.
Labusca et al. "Scaffold-free culture of mesenchymal stem cell spheroids in suspension preserves multilineage potential", Cell Tissue Res. Mar. 2012; 347(3): 701-711.
Labusca, "Scaffold free 3D culture of mesenchymal stem cells; implications for regenerative medicine", J Transplant Stem Cel Biol 2015 2(1): 8.
Landry et al, "Spheroidal aggregate culture of rat liver cells: histotypic reorganization, biomatrix deposition, and maintenance of functional activities" J Cell Biol 1985; 101:914-923.
Lau et al., "Evaluation of a Novel In Vitro CACO-2 Hepatocyte Hybrid System for Predicting In Vivo Oral Bioavailability" Drug Metabolism and Disposition, vol. 32, No. 9, pp. 937-942, 2004.
Lin et al., "La2Zr2O7 and MgO co-doped composite Li-Garnet solid electrolyte", Journal of Energy Chemistry, vol. 40, 2020, pp. 132-136.
Liquid Surge Control, LLC; "The Latest in Drop-In Baffle Technology"; 2 Pages; (2019).
Liu et al. "Quasi-spherical microwells on superhydrophobic substrates for long term culture of multicellular spheroids and high throughput assays" Biomaterials and Cancer 35 (2014) pp. 6060-6068.
Liu et al; "Advanced Micromachining of Concave Microwells for Long Term On-Chip Culture of Multicellular Tumour Spheroids", ACS Appl. Mater. Interfaces, 2014, 35 Pages.
LONZA Inc., "SeaPrep Agarose: An Ultralow Gelling, Soft Agarose", Available Online at <http://www.lonzabio.jp/catalog/pdf/pd/PD031.pdf>, 2007, pp. 1-4.
Lovett et al. "Vascularization Strategies for Tissue Engineering" Tissue Engineering Part B, 2009, vol. 15, No. 3, pp. 353-370.
LQUID Surge Control, LLC; "The Latest in Drop-In Baffle Technology"; 2 Pages; (2019).
Lu et al. "Galactosylated PVDF membrane promotes hepatocyte attachment and functional maintenance." Biomaterials 2003;24:4893-903.
Markovitz-Bishitz, "A polymer microstructure array for the formation, culturing, and high throughput drug screening of breast cancer spheroids" Biomaterials and Biotechnology 31 (2010) pp. 8436-8444.
Martin et al., "Agarose and Methylcellulose Hydrogel Blends for Nerve Regeneration Applications", J. Neural Eng., vol. 5, 2008, pp. 221-231.
McMillan, "Shear stress in microfluidic devices" Darwin Microfludics interner article (Year: 2017).
Messner et al, Multi-cell type human liver microtissues for hepatotoxicity testing. Archives of Toxicology, Nov. 11, 2012, 5 pages.
Mimetas the Organ-On-A-Chip Company; "Organ-On-A-Chip Models for Science and Pharma"; 4 Pages; (Downloaded Mar. 9, 2020); https://mimetas.com/.
Mironov et al; "Organ Printing: Tissue Spheroids as Buliding Blocks" Biomaterials, 2009; 30 (12) 2164-2174.
Moon et al; "Optimizing Human Embryonic Stem Cells Differentiation Efficiency by Screening Size-Tunable Homogenous Embryoid Bodies"; Biomaterials; 35 (2014) 5987-5997.
Murphy et al; "3D Bioprinting of Tissues and Organs"; Nature Biotechnology, vol. 32, No. 8. Aug. 2014, pp. 773-785.
Nortis; "Bridging the Gap Between In Vitro and In Vivo Research"; 16 Pages; (2015); https://www.nortisbio.com/.
Office Action and Search Report for CN 201580071454.0 mailed Sep. 27, 2019; 8 pages; Chinese Patent Office.
Office Action dated Aug. 8, 2019 pertaining to U.S. Appl. No. 15/708,473, filed Sep. 19, 2017, 20 pgs.
Organovo, "Pioneering Bioprinted Tissues to Treat Disease"; 2 Pages; (Downloaded Mar. 9, 2020) http://organovo.com/.
Otsuka et al, "Two-dimensional multiarray formation of hepatocyte spheroids on a microfabricated PEG-brush surface." ChemBioChem 2004; 5:850-855.
Peshwa et al, "Mechanistics of formation and ultrastructural evaluation of hepatocyte spheroids." In Vitro Cell Dev Biol Anim 1996; 32:197-203.
Polyimide: Japan Polyimide and Aromatic Polymers Study Group, 2010, pp. 364-371 Table 2.
Rezende et al, "Scalable Biofabrication of Tissue Spheroids for Organ Printing"; Sciverse Science Direct, Procedia Cirp 5, (2013) 276-281.
Sa et al. "Round-bottomed Honeycomb Microwells: Embryoid body shape correlates with stem cell fate" Journal of Developmental Biology and Tissue Engineering vol. 4(2), pp. 12-22, May 2012.
Sakai et al, "Large-scale preparation and function of porcine hepatocyte spheroids." Int J Artif Organs 1996; vol. 19, No. 5, pp. 294-301.
Sakai et al, "Technique for the Control of Spheroid Diameter Using Microfabricated Chips"; ScienceDirect, Acta Biomaterialia 3 (2007) 1033-1040.
Sakai et al; "Detachably Assembled Microfluidic Device for Perfusion Culture and Post-Culture Analysis of Spheroid Array"; Biotechnol. J. 2014, 9, 971-979.
Sart et al. "Three-dimensional aggregates of mesenchymal stem cells: cellular mechanisms, biological properties and applications." Tissue engineering, 2013, Part B, vol. 20, No. 5, pp. 1-16.
Satoh et al, "A Pneumatic Pressure-Driven Multi-Throughput Microfluidic Circulation Culture System" Lab Chip, 2016, 16, 2339-2348.
Seldon et al; "Evaluation of Encapsulated Liver Cell Spheroids in a Fluidised-Bed Bioartificial Liver for Treatment of Ischaemic Acute Liver Failure in Pigs in the Translational Setting": PLOS One; Dec. 2013, vol. 8, Issue 12, 12 Pages.
Stemcell Technologies, Reproducible and Uniform Embryoid Bodies Using AggreWell Plates, StemCell Technologies, Version 3.0.0, Mar. 2011, Catalog #29146, pp. 1-28.
Takezawa et al. "Morphological and immunocytochemical characterization of a heterospheroid composed of fibroblasts and hepatocytes." J Cell Sci 1992; 101:495-501.
Tara; "Innovating Predictive Cardiac Physiology"; 4 Pages; (2019) http://tarabiosystems.com/.
The Lab Depot(Registered) Products for Discovery Lab Supplies; Shake Flasks, 3 and 4 Baffles Product Information; 5 Pages (2019).
Tissuse; Technology, Available on (https://www.tissuse.com/en/technology/), Accessed May 11, 2021, 4 pages.
Tobe et al, "Receptor-mediated formation of multilayer aggregates of primary cultured adult rat hepatocytes on tactose-subsliluled polystyrene" Biochem Biophys Res Commun 1992; 184(1):225-230.
Tong et al, "Long-term culture of adult rat hepatocyte spheroids." Exp Cell Res 1992; 200:326-332.
TPP, webpage entitled "Tissue Culture Flask with re-closable Lid", <http://www.1stbio.com/shop/goods/goods_view.php?goodsno=15> cached by Internet Archive Apr. 8, 2017, screenshot attached (Year: 2017).
Truckemller, et al., Thermoforming of Film-Based Biomedical Microdevices, Adv. Mater. 2011, 23, pp. 1311-1329.
Tung et al, "High-throughput 3D spheroid culture and drug testing using 384 hanging drop array" Analyst, 2011, 136 (3), 473-478.
Uchida et al; "An Injectable Spheroid System With Genetic Modification for Cell Transplantation Therapy"; Biomaterials, 35 (2014) 2499-2506.

* cited by examiner

CELL CULTURE VESSEL

CROSS REFERENCE TO RELATED APPLICATION

This application is a divisional of U.S. patent application Ser. No. 16/628,474 filed on Jan. 3, 2020, which is a national stage application under 35 U.S.C. § 371 of International Application No. PCT/US2018/042133 filed on Jul. 13, 2018, which claims the benefit of priority of U.S. Provisional Application Ser. No. 62/642,427 filed on Mar. 13, 2018, entitled "Cell Culture Container and Methods of Culturing Cells"; U.S. Provisional Application Ser. No. 62/532,681 filed on Jul. 14, 2017, entitled "Cell Culture Container and Methods of Culturing Cells"; U.S. Provisional Application Ser. No. 62/532,639 filed on Jul. 14, 2017, entitled "Cell Culture Containers and Methods of Culturing Cells"; U.S. Provisional Application Ser. No. 62/532,648 filed on Jul. 14, 2017, entitled "Cell Culture Container and Methods of Culturing Cells"; and U.S. Provisional Application Ser. No. 62/532,671 filed on Jul. 14, 2017, entitled "Cell Culture Containers and Methods of Culturing Cells"; the content of which are relied upon and incorporated herein by reference in their entireties.

FIELD

The present disclosure relates generally to cell culture vessels and methods of culturing cells, and more particularly, to cell culture vessels for containing three-dimensional cells and methods of culturing three-dimensional cells in the cell culture vessel.

BACKGROUND

It is known to contain three-dimensional cells in a cell culture vessel. It is also known to culture three-dimensional cells in a cell culture vessel.

SUMMARY

The following presents a simplified summary of the disclosure in order to provide a basic understanding of some exemplary embodiments described in the detailed description.

In some embodiments, a cell culture vessel has sidewalls and a bottom surface. In embodiments, the bottom surface, is a cell culture surface having a plurality of microcavities. In embodiments, the cell culture surface is a substrate attached to the sidewalls. In embodiments, the sidewalls are attached to the substrate so that there are no flat surfaces around the periphery of the cell culture surface.

In embodiments, the vessel can include a top, a bottom, sidewalls, a necked opening or aperture and an endwall, opposite the necked opening. Or, in embodiments, the cell culture vessel may have a lid. Or, in embodiments, the cell culture vessel may have a lid, which may be the top of the vessel, and a necked opening or aperture. The interior surface of the bottom of the vessel is, in embodiments, the cell culture surface. The cell culture surface can span a length of the cell culture chamber. The vessel can include a neck portion of the inner surface of the wall extending from the aperture to the cell culture surface at an angle. A method of culturing cells in the cell culture vessel can include passing liquid through the aperture from outside the vessel into the cell culture chamber, thereby providing a predetermined amount of liquid to the cell culture chamber.

In embodiments, each microcavity of the plurality of microcavities has a concave bottom surface and an opening at the top. Liquid enters each microcavity through the opening at the top of each microcavity.

In embodiments, the vessel can have a necked opening or aperture that can be closed with a cap. In embodiments, the top wall of the vessel may be a lid. In embodiments, the lid can be opened, with a sliding opening or with a hinged opening, or with any other known opening mechanism. In embodiments, the vessel does not have a necked opening, and has a lid instead.

A method of culturing cells in the cell culture vessel can include introducing a predetermined amount of liquid, such as liquid media, containing cells, into the cell culture chamber, and depositing at least a portion of the predetermined amount of liquid in at least one microcavity of the plurality of microcavities. The method can further include culturing cells in the at least one microcavity of the plurality of microcavities after depositing the at least a portion of the predetermined amount of liquid in the at least one microcavity.

The above embodiments are exemplary and can be provided alone or in any combination with any one or more embodiments provided herein without departing from the scope of the disclosure. Moreover, it is to be understood that both the foregoing general description and the following detailed description present embodiments of the present disclosure, and are intended to provide an overview or framework for understanding the nature and character of the embodiments as they are described and claimed. The accompanying drawings are included to provide a further understanding of the embodiments, and are incorporated into and constitute a part of this specification. The drawings illustrate various embodiments of the disclosure, and together with the description, serve to explain the principles and operations thereof.

BRIEF DESCRIPTION OF THE DRAWINGS

These and other features, embodiments, and advantages of the present disclosure can be further understood when read with reference to the accompanying drawings in which.

DETAILED DESCRIPTION

Figure 1:
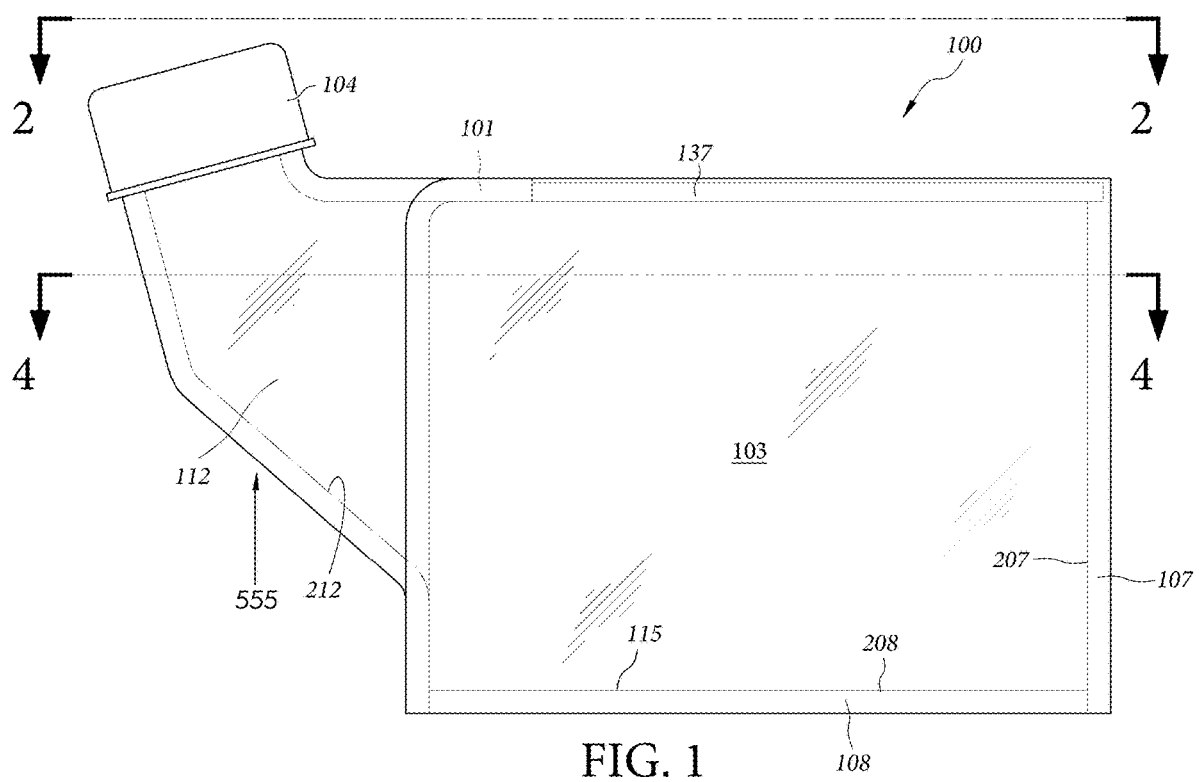
FIG. 1 schematically illustrates a side view of a cell culture vessel in accordance with embodiments of the disclosure.

Features will now be described more fully hereinafter with reference to the accompanying drawings in which exemplary embodiments of the disclosure are shown. Whenever possible, the same reference numerals are used throughout the drawings to refer to the same or like parts. However, this disclosure can be embodied in many different forms and should not be construed as limited to the embodiments set forth herein.

A cell culture vessel (e.g., flask) can provide a sterile cell culture chamber for culturing cells. In some embodiments, culturing cells can provide information related to the study of diseases and toxicology, the efficacy of medications and treatments, characteristics of tumors, organisms, genetics, and other scientific, biological, and chemical principles of and relating to cells.

As compared to two-dimensional cell cultures, in some embodiments, three-dimensional cell cultures can produce multicellular structures that are more physiologically accurate and that more realistically represent an environment in which cells can exist and grow in real life applications as compared to simulated conditions in a laboratory. For example, three-dimensional cell cultures have been found to more closely provide a realistic environment simulating "in vivo" (i.e. within the living, in a real-life setting) cell growth; whereas two-dimensional cell-cultures have been found to provide an environment simulating "in vitro" (i.e., within the glass, in a laboratory setting) cell growth that is less representative of a real-life environment occurring outside of a laboratory. By interacting with and observing the properties and behavior of three-dimensional cell cultures, advancements in the understanding of cells relating to, for example, the study of diseases and toxicology, the efficacy of medications and treatments, characteristics of tumors, organisms, genetics, and other scientific, biological, and chemical principles of and relating to cells can be achieved. Under certain conditions, cells will clump together to form three dimensional "balls" of cells called spheroids or organoids.

For these types of studies and uses, it is desirable to provide controlled, homogeneous populations of spheroids. Cell culture vessels can be structured and arranged to provide an appropriate environment for cells to form spheroids in culture. The cell culture vessel can include a cell culture surface including a plurality of microcavities (e.g., microcavities, micron-sized wells, submillimeter-sized wells). When these microcavities are arranged in an array, providing a large number of microcavities in a single cell culture vessel, it is possible to culture large numbers of spheroids, and therefore it is possible to carry out assays and experiments on a large number of cells.

However, when flat surfaces are present in a cell culture vessel intended to grow spheroids, cells can settle onto these flat surfaces and form irregular cellular conglomerates. These are undesirable. In embodiments, the disclosure provides cell culture vessels that do not have flat surfaces that cells can settle on and grow in an irregular multicellular form. That is, the cell culture surface of the vessel consists substantially of microcavities.

In embodiments, the cell culture surface can be an insert placed in the flask or the cell culture surface can be bonded to the wall of the cell culture vessel. A cell culture surface having an array of microcavities can be bonded to the wall of a cell culture vessel by, for example gluing, laser welding, ultrasonic welding, or some other method. The cell culture surface can include top and/or bottom sides that include undulating (e.g., sinusoidal) surfaces that form the plurality of microcavities.

When culturing cells, the vessel can be filled with a material (e.g., media, solid, liquid, gas) that facilitates growth of three-dimensional cell cultures (e.g., cell aggregates, spheroids). For example, a media including cells suspended in a liquid can be added to the cell culture chamber of the vessel. The suspended cells can collect in the plurality of microcavities and can form (e.g., grow) into groups or clusters of cells. These groups or clusters are spheroids or organoids.

For example, in some embodiments, a single spheroid can form in each microcavity of the plurality of microcavities based at least on gravity causing one or more cells suspended in a liquid to fall through the liquid and become deposited within each microcavity. The shape of the microcavity (e.g., a concave surface or bottom defining a well), and a surface coating of the microcavity that prevents the cells from attaching to the surface can also facilitate growth of three-dimensional cell cultures in each microcavity. That is, the cells form spheroids and are constrained by the dimensions of the microcavity to grow to a certain size. During culturing, the spheroids can consume media (e.g., food, nutrients) and produce metabolite (e.g., waste) as a byproduct. Thus, in some embodiments food media can be added to the cell culture chamber during culturing and waste media can be removed from the cell culture chamber during culturing. Attempts can be made when adding and removing media to avoid displacing the spheroids from the microcavities and promote desired cell culturing of the spheroids.

Figure 2:
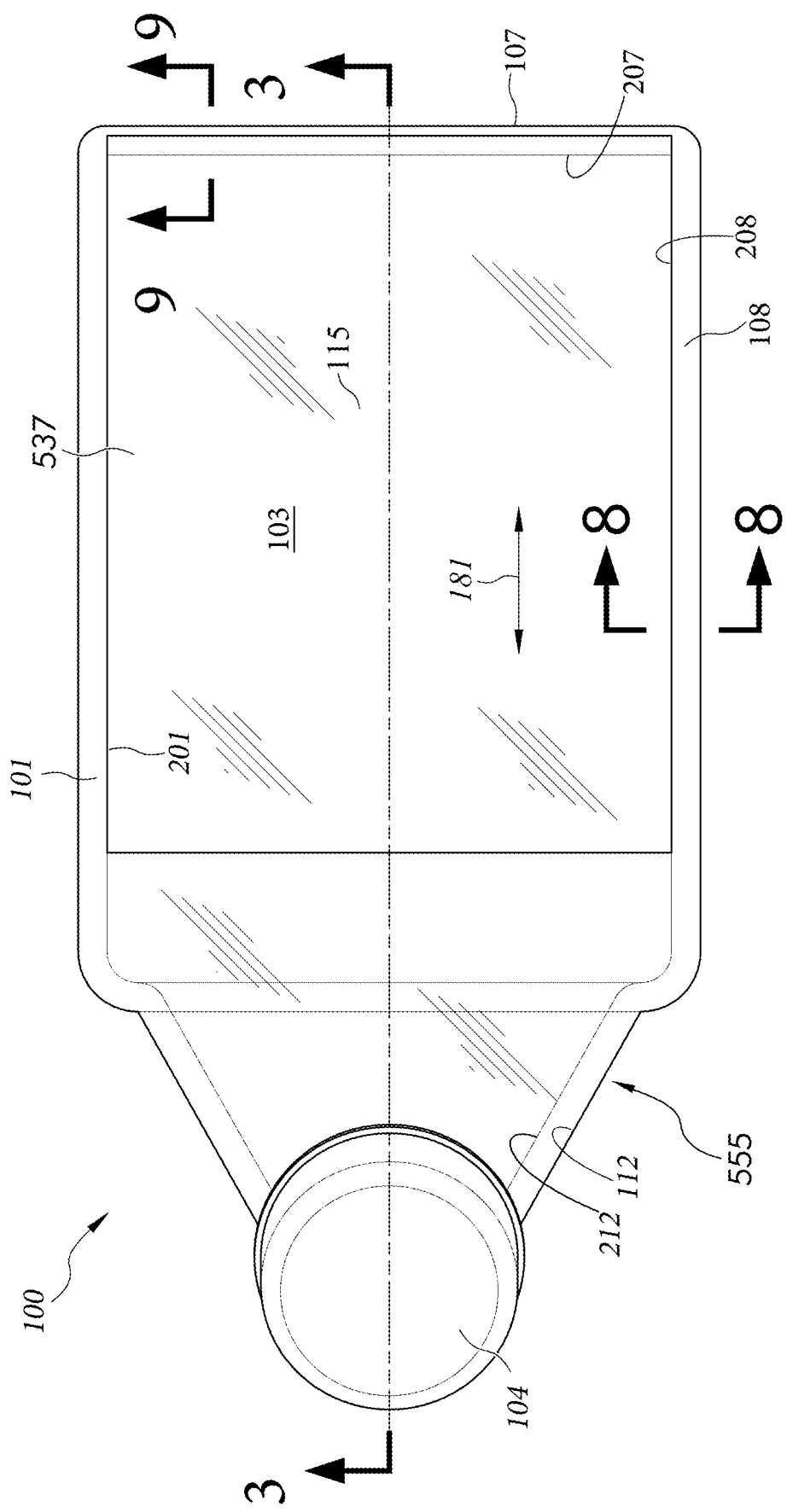
FIG. 2 shows a plan view of cell culture vessel along line 2-2 of FIG. 1 in accordance with embodiments of the disclosure.

Embodiments of cell culture vessel 100 and methods of culturing cells in the cell culture vessel 100 will now be described with reference to FIGS. 1-37. FIG. 1 illustrates a side view of an embodiment of a cell culture vessel 100, and FIG. 2 shows a plan view of the vessel 100 along line 2-2 of FIG. 1. In some embodiments, the cell culture vessel 100 can include a top 101, a bottom 108, a necked opening 112 and a port, shown in FIG. 1 covered by a cap 104. FIG. 2, a plan view, shows wall 107 surrounding the cell culture surface 115. Each of these that features, top 101 bottom 108, and wall 107 (shown in FIG. 2) and the necked opening 112 have interior surfaces. That is, top 101 has an interior surface 201, wall 107 has an interior surface 207, bottom 108 has an interior surface 208, and necked opening 112 has an interior surface 212. These interior surfaces define the cell culture chamber 103. The interior surface 208 of the bottom 108 of the vessel 100 is the cell culture surface 115. This cell culture surface 115 has an array of microcavities (See FIGS. 5-7) for containing and culturing spheroids. As shown in FIG. 2, the interior surface of the wall abuts the cell culture surface 115. In embodiments, there are no flat surfaces between the cell culture surface 115 and the interior surface 207 of wall 107. That is, the cell culture surface 115 is substantially free of flat surfaces. Stated another way, the cell culture surface 115 is made up of microcavities entirely. The cell culture surface consists essentially of microcavities.

Figure 3:
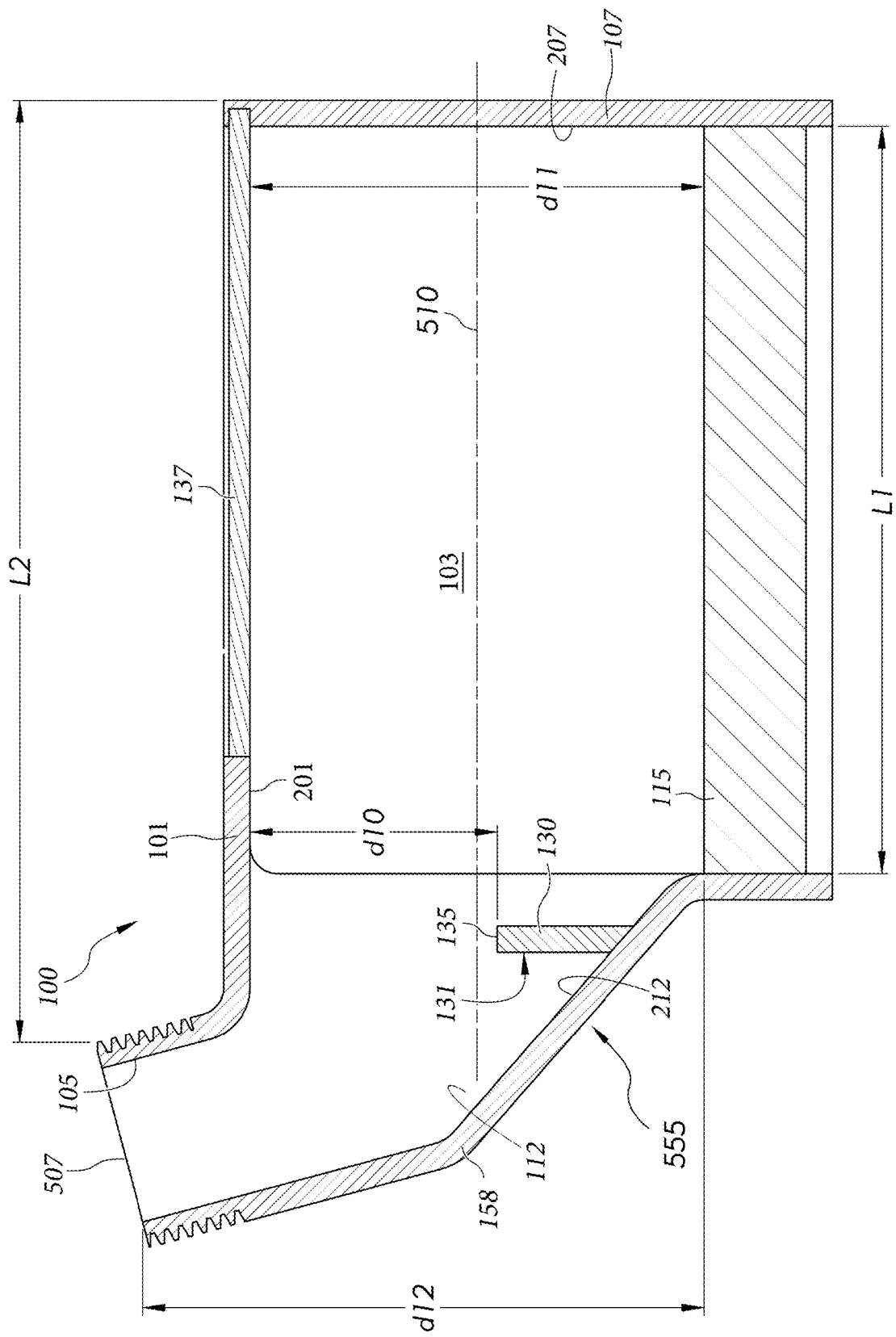
FIG. 3 shows a cross-sectional view of cell culture vessel along line 3-3 of FIG. 1 in accordance with embodiments of the disclosure.

The vessel can be manufactured from a material including, but not limited to, polymer, polycarbonate, glass, and plastic. In the drawing figures, the vessel 100 is illustrated as being manufactured from a clear (e.g., transparent) material; although, in some embodiments, the vessel 100 may, alternatively, be manufactured from a semi-transparent, semi-opaque, or opaque material without departing from the scope of the disclosure. FIG. 3 shows a cross-sectional view of the vessel 100 along line 3-3 of FIG. 1. In some embodiments, the cell culture surface 115 and the inner surface 207 of the wall 107 defines a cell culture chamber 103 of the vessel 100, with an aperture 105 extending through the wall 107 in fluid communication with the cell culture chamber 103. For example, in some embodiments, the cell culture chamber 103 can include an internal spatial volume of the vessel 100.

Turning back to FIG. 1 and FIG. 2, in some embodiments, the vessel 100 can include a cap 104 oriented to cover the aperture 105 to at least one of seal and block the aperture 105, thereby obstructing a path into the cell culture chamber 103 from outside the vessel 100 through the aperture 105. For clarity purposes, the cap 104 is removed and, therefore, not shown in other drawing figures, although it is to be understood that the cap 104 can be provided and selectively added to or removed from the aperture 105 of the vessel 100, in some embodiments, without departing from the scope of the disclosure. In some embodiments, the cap 104 can include a filter that permits the transfer of gas in to and/or out of the cell culture chamber 103 of the vessel 100. For example, in some embodiments, the cap 104 can include a gas-permeable filter oriented to regulate a pressure of gas within the cell culture chamber 103, thereby preventing pressurization (e.g., over-pressurization) of the cell culture chamber 103 relative to a pressure of the environment (e.g., atmosphere) outside the vessel 100.

Figure 4:
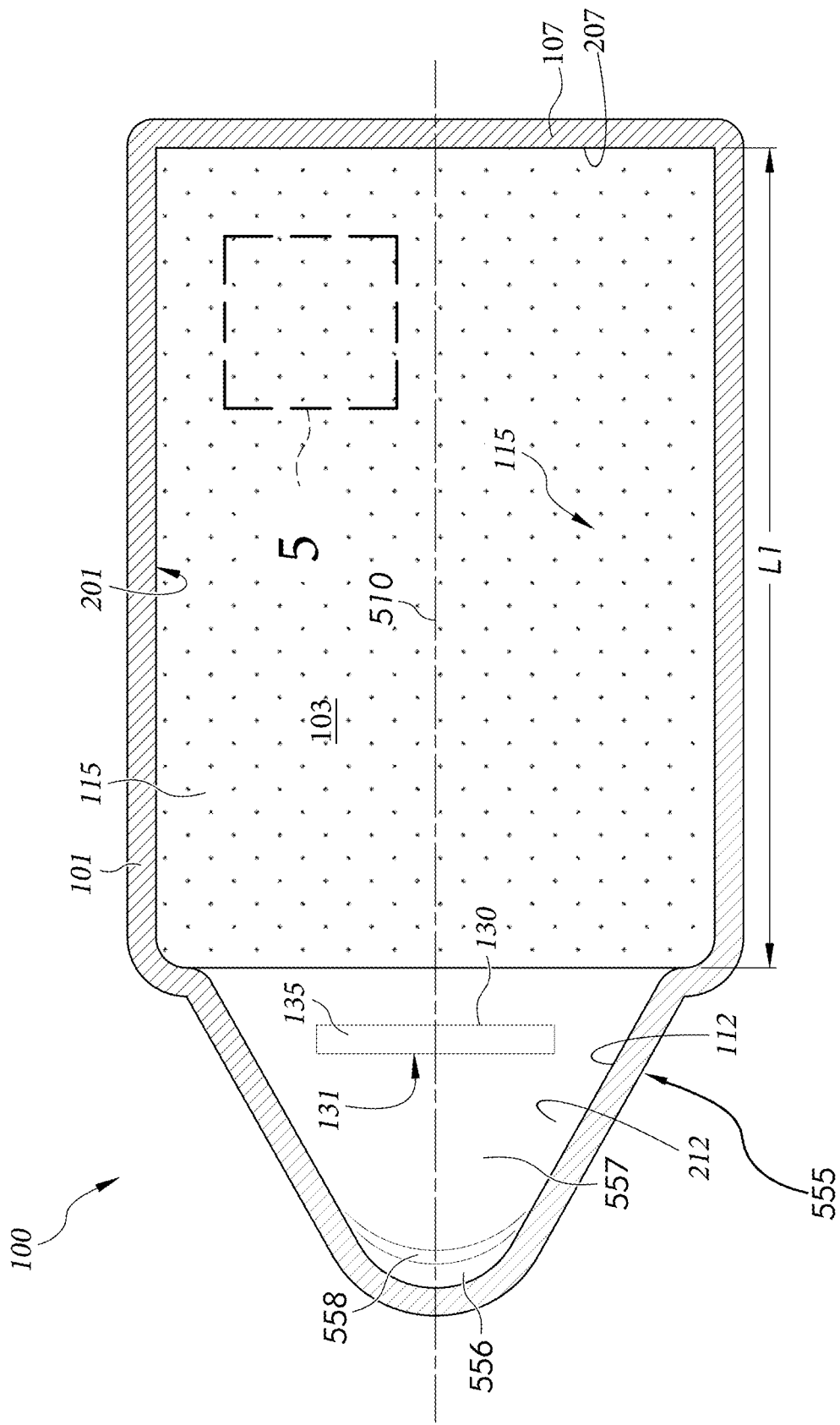
FIG. 4 shows a cross-sectional view of the cell culture vessel along line 4-4 of FIG. 1 in accordance with embodiments of the disclosure.
Figure 5:
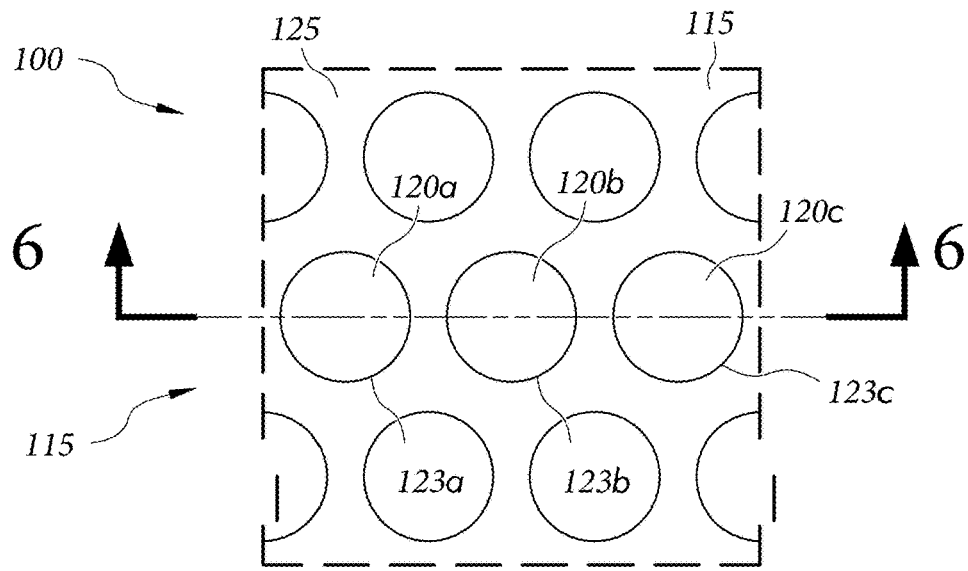
FIG. 5 illustrates an enlarged schematic representation of a cell culture vessel taken at view 5 of FIG. 4 including a cell culture surface having a plurality of microcavities in accordance with embodiments of the disclosure.
Figure 6:
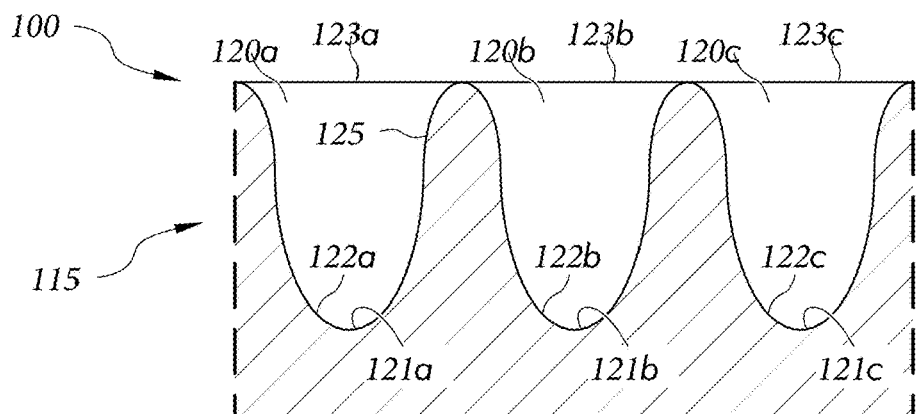
FIG. 6 shows a cross-sectional view of a cell culture vessel having a cell culture surface having a plurality of microcavities along line 6-6 of FIG. 5 in accordance with embodiments of the disclosure.
Figure 7:
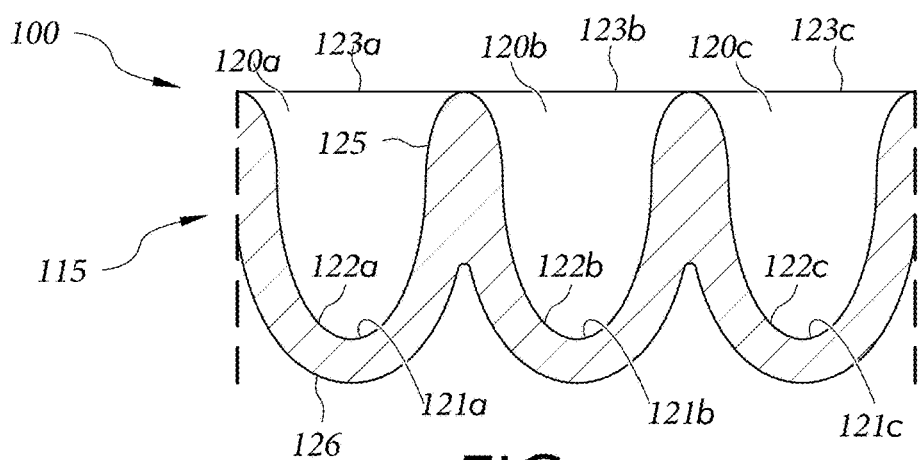
FIG. 7 shows an alternative embodiment of the cross-sectional view of a cell culture vessel including a cell culture surface having a plurality of microcavities of FIG. 6 in accordance with embodiments of the disclosure.

As shown in FIG. 3, which shows a cross-sectional view along line 3-3 of FIG. 2, and in FIG. 4, which shows a cross-sectional view along line 4-4 of FIG. 1, in some embodiments, the cell culture surface 115 can span a length "L1" of the cell culture chamber 103 that extends along the axis 510. FIG. 5 shows an enlarged schematic representation of a portion of the cell culture surface 115 taken at view 5 of FIG. 4. Additionally, FIG. 6 shows a cross-sectional view of the portion of the cell culture surface 115 along line 6-6 of FIG. 5, and FIG. 7 shows an alternative embodiment of the cross-sectional view of FIG. 6. As shown in FIG. 5, in some embodiments, microcavities 120 can be arranged in a diagonal array, although other arrangements can be provided in other embodiments. Additionally, in some embodiments, each microcavity 120*a*, 120*b*, 120*c* can include a concave bottom 121*a*, 121*b*, 121*c* (See FIG. 6 and FIG. 7) defining a well 122*a*, 122*b*, 122*c*. Further, each microcavity 120*a*, 120*b*, 120*c* can include an opening 123*a*, 123*b*, 123*c* in the top of each microcavity 120. As shown in FIG. 6, in some embodiments, the first side 125 of the cell culture surface 115 can include a non-linear (e.g., undulating, sinusoidal) profile and a second side 126 of the cell culture surface 115 can be flat. Similarly, as shown in FIG. 7, in some embodiments, both the first side 125 and the second side 126 of the cell culture surface 115 can include a non-planar (e.g., undulating, sinusoidal) profile.

In embodiments, the cell culture surface 115, and the vessel 100 (as discussed in FIGS. 1-16) and 300 (as discussed in FIG. 17-34) can include a polymeric material including, but not limited to, polystyrene, polymethylmethacrylate, polyvinyl chloride, polycarbonate, polysulfone, polystyrene copolymers, fluoropolymers, polyesters, polyamides, polystyrene butadiene copolymers, fully hydrogenated styrenic polymers, polycarbonate PDMS copolymers, and polyolefins such as polyethylene, polypropylene, polymethyl pentene, polypropylene copolymers and cyclic olefin copolymers. Additionally, in some embodiments, at least a portion of the well 122*a*, 122*b*, 122*c* defined by the concave bottom 121*a*, 121*b*, 121*c* can be coated with an ultra-low binding material, thereby making the at least a portion of the well 122*a*, 122*b*, 122*c* non-adherent to cells. For example, in some embodiments, one or more of perfluorinated polymers, olefins, agarose, non-ionic hydrogels such as polyacrylamides, polyethers such as polyethyleneoxide, polyols such as polyvinylalcohol or mixtures thereof can be applied to at least a portion of the well 122*a*, 122*b*, 122*c* defined by the concave surface 121*a*, 121*b*, 121*c*.

Moreover, in some embodiments, each microcavity 120*a*, 120*b*, 120*c* of the plurality of microcavities 120 (as discussed in FIGS. 1-16) and 320 (as discussed in FIG. 17-34) can include a variety of features and variations of those features without departing from the scope of the disclosure. For example, in some embodiments the plurality of microcavities 120 can be arranged in an array including a linear array (shown), a diagonal array, a rectangular array, a circular array, a radial array, a hexagonal close-packed arrangement, etc. Additionally, in some embodiments, the opening 123*a*, 123*b*, 123*c* can include a variety of shapes. In some embodiments, the opening 123*a*, 123*b*, 123*c* can include one or more of a circle, an oval, a rectangle, a quadrilateral, a hexagon, and other polygonal shapes. Additionally, in some embodiments, the opening 123*a*, 123*b*, 123*c* can include a dimension (e.g., diameter, width, diagonal of a square or rectangle, etc.) from about 100 microns (μm) to about 5000 μm. For example, in some embodiments, the opening 123*a*, 123*b*, 123*c* can include a dimension of 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1000 μm, 1500 μm, 2000 μm, 2500 μm, 3000 μm, 3500 μm, 4000 μm, 4500 μm, 5000 μm, and any dimension or ranges of dimensions encompassed within the range of from about 100 μm to about 5000 μm.

In some embodiments, the well 122*a*, 122*b*, 122*c* (as discussed in FIGS. 1-16) and 322 (as discussed in FIG. 17-34) defined by the concave surface 121*a*, 121*b*, 121*c* can include a variety of shapes. In some embodiments, the well 122*a*, 122*b*, 122*c* defined by the concave surface 121*a*, 121*b*, 121*c* can include one or more of a circular, elliptical, parabolic, hyperbolic, chevron, sloped, or other cross-sectional profile shape. Additionally, in some embodiments, a depth of the well 122*a*, 122*b*, 122*c* (e.g., depth from a plane defined by the opening 123*a*, 123*b*, 123*c* to the concave surface 121*a*, 121*b*, 121*c* can include a dimension from about 100 microns (μm) to about 5000 μm. For example, in some embodiments, the depth of the well 122*a*, 122*b*, 122*c* can include a dimension of 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1000 μm, 1500 μm, 2000 μm, 2500 μm, 3000 μm, 3500 μm, 4000 μm, 4500 μm, 5000 μm, any dimension or ranges of dimensions encompassed within the range of from about 100 μm to about 5000 μm.

In some embodiments, three-dimensional cells 150 (e.g., spheroids, organoids 150*a*, 150*b*, 150*c*) (See FIG. 16) (as discussed in FIGS. 1-16) and 350 (as discussed in FIG. 17-34) that can be cultured in at least one microcavity 120*a*, 120*b*, 120*c* of the plurality of microcavities 120 can include a dimension (e.g., diameter) of from about 50 μm to about 5000 μm, and any dimension or ranges of dimensions encompassed within the range of from about 50 μm to about 5000 μm. In some embodiments, dimensions greater than or less than the explicit dimensions disclosed can be provided and, therefore, unless otherwise noted, dimensions greater than or less than the explicit dimensions disclosed are considered to be within the scope of the disclosure. For example, in some embodiments, one or more dimensions of the opening 123*a*, 123*b*, 123*c*, the depth of the well 122*a*, 122*b*, 122*c*, and the dimension of the three-dimensional cells 150 (e.g., spheroids 150*a*, 150*b*, 150*c*) can be greater than or less than the explicit dimensions disclosed without departing from the scope of the disclosure.

Turning back to FIGS. 1-4, in some embodiments, the vessel 100 can include a neck portion 555 extending from the aperture 105 to the cell culture surface 115. In some embodiments, the neck portion 555 can include one or more of an inclined (e.g., canted) profile, a profile that narrows in a direction toward and/or away from the aperture 105, and a profile that widens in a direction toward and/or away from the cell culture surface 115. As shown in FIG. 3, in some embodiments, the neck portion 555 is angled with respect to the cell culture chamber 103. Additionally, in some embodiments, the neck portion 555 of the vessel can have a bend 158. In embodiments, the bend 158 is higher than the cell culture surface 115. However, it is to be understood that, in some embodiments, the bend can be of any shape. For example, the bend 158 can be curved or sloped or angled or stepped.

In addition or alternatively, as shown in FIG. 3 and FIG. 4, in some embodiments, the cell culture vessel 100 can include a dam 130 extending from interior surface 212 of the neck portion 112. In some embodiments, the dam 130 can include a port-facing surface 131 obstructing a path defined between the aperture 105 and the cell culture surface 115. In some embodiments, the port-facing surface 131 of the dam 130 can be substantially perpendicular to the axis 510 of the vessel 100. Moreover, as shown in FIG. 3, in some embodiments, at least a portion of a free end 135 of the dam 130 can be spaced a distance "d10" from the inner surface 201 of the top 101. In some embodiments, by spacing at least a portion of the free end 135 of the dam 130 from the inner surface 201, in some embodiments, access to a rear portion of the vessel 100 (e.g., opposite the aperture 105) can be provided. For example, in some embodiments, one or more instruments (not shown) can be inserted into the aperture 105 of the vessel 100 past the dam 130 (e.g., through the distance "d10") to access a region of the cell culture chamber 103 positioned behind the dam 130. Accordingly, as disclosed, for example, with respect to the dam 130 of the first exemplary cell culture vessel 100, in some embodiments, the dam 130 of the cell culture vessel 100 can, likewise, at least one of obstruct and slow a velocity of material (e.g., food, nutrients) flowing in to and/or material (e.g., waste) flowing out of the vessel 100 while also permitting bulk access into the cell culture chamber 103 of the vessel 100.

As shown in FIG. 1, in some embodiments, the vessel 100 can include a lid 137. In some embodiments, the lid 137, when closed, can be the top 101 of the vessel 100. (see also FIG. 3). In some embodiments, the first major surface 538 can define at least a portion of the cell culture chamber 103. Additionally, in some embodiments, the lid 137 can be open or closed, or partially open (or partially closed). The lid 137 can be slidingly atached to the vessel 100 or, in embodiments, the lid 137 can be hingedly attached to the vessel 100. In some embodiments, the aperture 536 can be in fluid communication with the cell culture chamber 103.

Moreover, as shown in FIG. 3, in some embodiments, a first distance "d11" from the cell culture surface 115 to top 101 or lid 137 can be less than a second distance "d12" from the cell culture surface 115 to the opening 507 of the aperture 105. In some embodiments, the second distance "d12" from the cell culture surface 115 to the opening 507 of the aperture 105 can be defined at any location of the opening 507. However, in some embodiments, the second distance "d12" from cell culture surface 115 to the opening 507 of the aperture 105 can be defined as the closest location of the opening 507 of the aperture 105 relative to the cell culture surface 115. For example, in some embodiments, when the vessel 100 is oriented with the axis 510 extending in a direction perpendicular to the direction of gravity "g" (See FIG. 17), the second distance "d12" from the cell culture surface 115 to the opening 507 of the aperture 105 can be defined as the lowermost location of the opening 507 of the aperture 105 relative to the direction of gravity "g".

Accordingly, in some embodiments, as compared to a comparable vessel where, for example, a distance from the cell culture surface 115 extending to the lid portion 137 is greater than a second distance from the cell culture surface 115 to the opening 507 of the aperture 105, one or more features of the vessel 100, alone or in combination, can provide a cell culture chamber 103 including a larger volume in which material can be contained. That is, when the vessel 100 is oriented with the axis 510 extending in a direction perpendicular to the direction of gravity "g", the second distance "d12" from the cell culture surface 115 to the opening 507 of the aperture 105 (defined as the lowermost location of the opening 507 of the aperture 105 relative to the direction of gravity "g"), can define a maximum fill line with respect to a volume of material that can be contained within the cell culture chamber 103 of the vessel 100. For example, if the second distance "d12" is less than the first distance "d11", and the vessel 100 is oriented with the axis 510 extending in a direction perpendicular to the direction of gravity "g", the maximum fill line of a volume of material contained within the cell culture chamber 103 would be commensurate with the distance from the lid 137 as any additional material added to the cell culture chamber 103 would flow out of the opening of the aperture 105 rather than being contained within the cell culture chamber 103. Thus, if the second distance "d12" is less than the first distance "d11", and the vessel 100 is oriented with the axis 510 extending in a direction perpendicular to the direction of gravity "g", the vessel 100 can include a volume including a portion of the cell culture chamber 103 that is not employed with respect to containing material. Accordingly, in some embodiments, by providing the vessel 100, in accordance with embodiments of the disclosure, including the second distance "d12" that is greater than the first distance "d11", the entire volume of the cell culture chamber 103 can be employed to contain material, a larger volume of material can be contained in the cell culture chamber 103, and an efficient allocation of material and overall utilization of space of the vessel 100 can be achieved. Likewise, in some embodiments, the second distance "d12" can be equal to the first distance "d11", without departing from the scope of the disclosure.

Moreover, in some embodiments, with respect to a unit area of the cell culture surface 115 (e.g., a unit area providing a respective surface on which one or more cells can be cultured), three-dimensional cell culturing can consume more media (e.g., food, nutrients) and produce more media (e.g., waste) as a byproduct than, for example, a comparable two-dimensional cell culture. Thus, in some embodiments, as compared to, for example, a comparable two-dimensional cell culture, three-dimensional cell cultures in accordance with embodiments of the disclosure can include more frequent media exchanges (e.g., addition of food, nutrients and/or removal of waste) for a comparable period of time. In addition or alternatively, in some embodiments, as compared to, for example, a comparable two-dimensional cell culture, three-dimensional cell cultures in accordance with embodiments of the disclosure can include larger media volumes (e.g., consume more food, nutrients and/or produce more waste) for a comparable period of time. Accordingly, in some embodiments, one or more features of the cell culture vessel 100 and the methods of culturing cells 150 in the cell culture vessel 100 can provide advantages with respect to the frequency of media exchanges as well as the volume of media that can be one or more of contained within the cell culture chamber 103 of the vessel 100, added to the cell culture chamber 103, and removed from the cell culture chamber 103, thereby providing a desirable, effective environment in which to culture three-dimensional cells.

Figure 8:
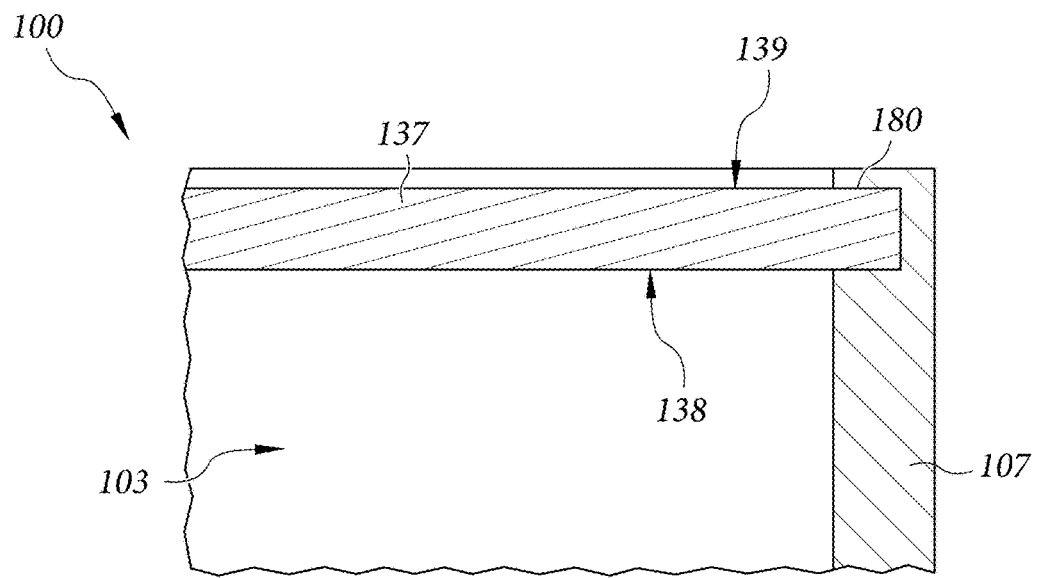
FIG. 8 shows a partial cross-sectional view of a cell culture vessel along line 8-8 of FIG. 2 including a lid portion and a groove in accordance with embodiments of the disclosure.
Figure 9:
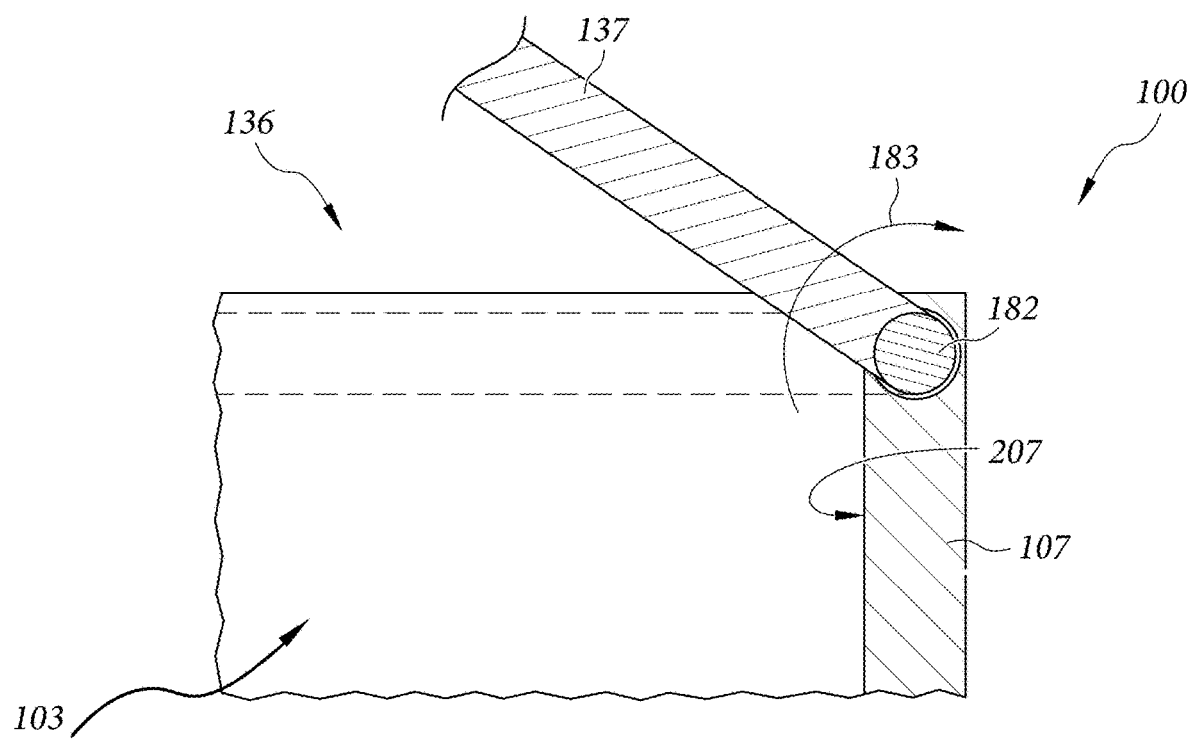
FIG. 9 shows a partial cross-sectional view of a cell culture vessel along line 9-9 of FIG. 2 including a lid and a hinge in accordance with embodiments of the disclosure.

As shown in FIG. 8 which shows a partial cross-sectional view of the vessel 100 along line 8-8 of FIG. 2, in some embodiments, top wall 101 can include a groove 180, and the lid 137 can be slideable within the groove 180 (as shown by arrow 181 in FIG. 2) to selectively provide access to the cell culture chamber 103, for example, through an opening of aperture 136. In addition or alternatively, as shown in FIG. 9 which shows a partial cross-sectional view of the vessel 100 along line 9-9 of FIG. 2, in some embodiments, the vessel 100 can include a hinge 182 connecting the lid 137 to the wall 101. In some embodiments, the lid 137 can be rotatable about the hinge 182 (as shown by arrow 183) to selectively provide access to the cell culture chamber 103, for example, through an opening of aperture 136. Moreover, in some embodiments, the lid 137 can be connected to the wall 101 with one or more fasteners (not shown) and/or adhesives (not shown) including reusable and non-reusable adhesives to, for example, selectively provide access to the cell culture chamber 103, for example, through an opening of aperture 136.

Additionally, in some embodiments, a length "L2" of the vessel 100, measured from the port 105 to the end wall 107 extending along the axis 510 of the vessel can be equal to or greater than the length "L1" of the cell culture surface 115. Accordingly, in some embodiments, a plurality of vessels 100 can be stacked (e.g., vertically relative to the direction of gravity) to, for example, reduce a surface area (e.g., laboratory surface area, table surface area) occupied by the plurality of vessels 100. For example, FIG. 10 schematically illustrates a side view of a plurality of vessels 100, 100a, 100b stacked together in accordance with embodiments of the disclosure.

Figure 10:
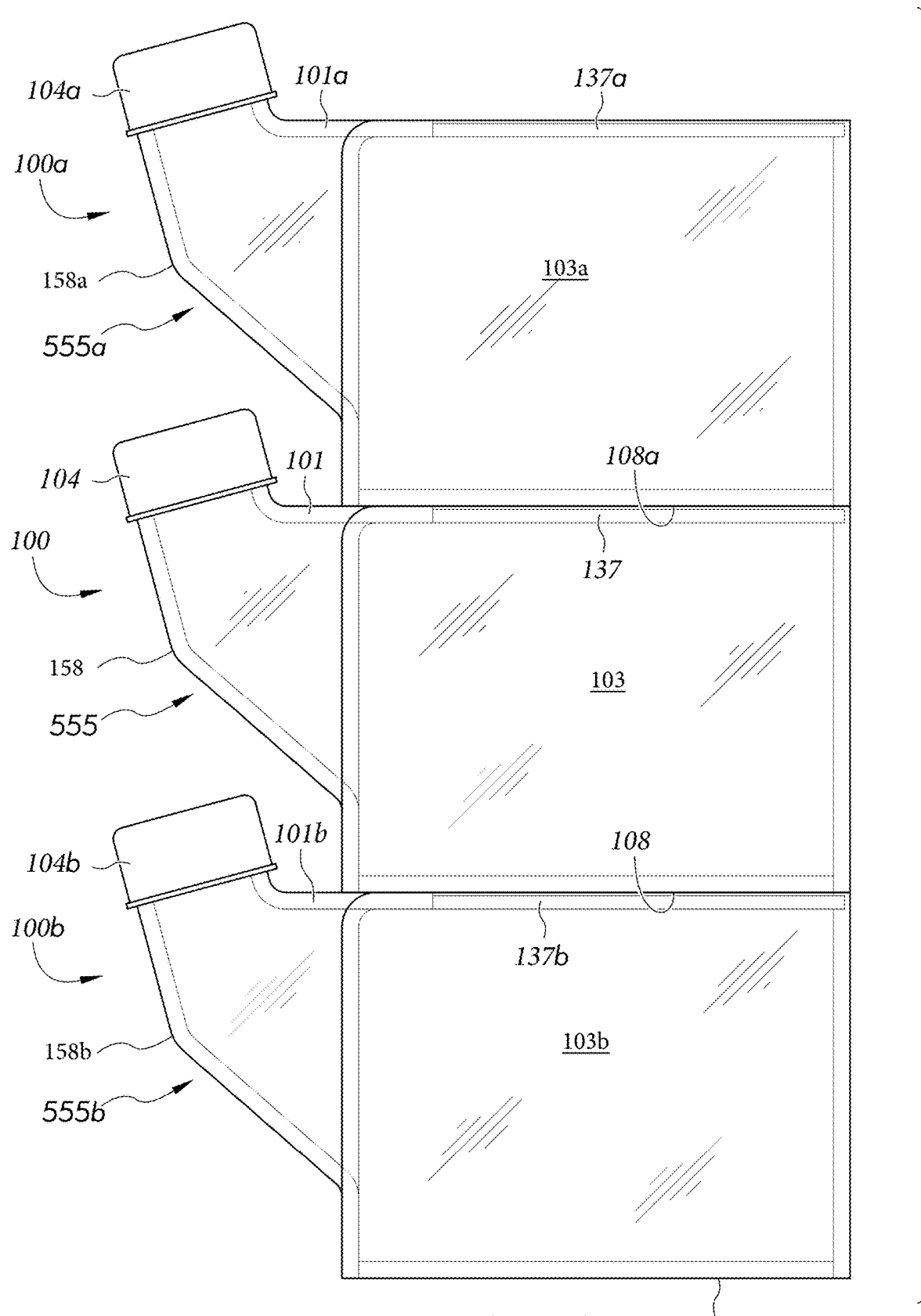
FIG. 10 schematically illustrates a side view of three cell culture vessels that are stacked together in accordance with embodiments of the disclosure.

As shown schematically in FIG. 10, in some embodiments, vessel 100a including wall 101a, cap 104a, neck portion 555a, lid 137a, and a bottom 108a can be stacked, one on top of the other. For example, in some embodiments, the bottom portion 108b of vessel 100b, with walls 101, 101a, 101b, can be placed on a horizontal surface (not shown) that defines a major surface perpendicular to the direction of gravity. In some embodiments, the bottom portion 108 of vessel 100 can be positioned on (e.g., facing) the lid 137b of the vessel 100b. Likewise, in some embodiments, the bottom portion 108a of vessel 100a can be positioned on (e.g., facing) lid 137 of vessel 100. By positioning (e.g., stacking) the plurality of vessels 100, 100a, 100b in accordance with embodiments of the disclosure, the plurality of vessels 100, 100a, 100b can efficiently utilize a space (e.g., area, volume) in which the vessels 100, 100a, 100b are provided, for example, during one or more of storage, cleaning, and culturing with respect to the vessels 100, 100a, 100b. Although shown as a plurality of three stacked vessels 100, 100a, 100b, it is to be understood that, in some embodiments, two vessels or more than three vessels can be stacked in accordance with embodiments of the disclosure, without departing from the scope of the disclosure. Moreover, in some embodiments the plurality of vessels 100, 100a, 100b can be positioned separately and/or together (e.g., stacked) in a variety of configurations including configurations not explicitly disclosed in the disclosure, without departing from the scope of the disclosure.

In embodiments, the vessels are stackable. Moreover, based at least in part on one or more features of the bend 158 in the neck 112, when stacked in accordance with embodiments of the disclosure, access to the ports 105, 105a, 105b can be maintained to, for example, permit addition of material (e.g., food, nutrients) and/or removal of material (e.g., waste) from the respective cell culture chambers 103, 103a, 103b while the plurality of vessels 100, 100a, 100b are stacked (e.g., stationary). For example, in some embodiments, stacking vessels that do not include one or more features of the disclosure could one or more of limit, obstruct, and prevent access to the openings of the apertures. In some embodiments, stacked vessels including openings of the apertures to which access is one or more of limited, obstructed, and prevented may be moved (e.g., at least one of translated and rotated) relative to each other during a culturing process to, for example, provide access to the openings of the apertures. However, in some embodiments, movement of vessels relative to each other during a culturing process may one or more of dislodge and disturb cells being cultured in the vessels, thereby negatively impacting the cell culture process. Accordingly, based at least in part on one or more features of the bend 158, 158a, 158b of the neck 555, 555a, 555b of the vessel 100, 100a, 100b, when stacked in accordance with embodiments of the disclosure, access to the openings of the port can be achieved and advantages with respect to a cell culturing process can be obtained.

Figure 11:
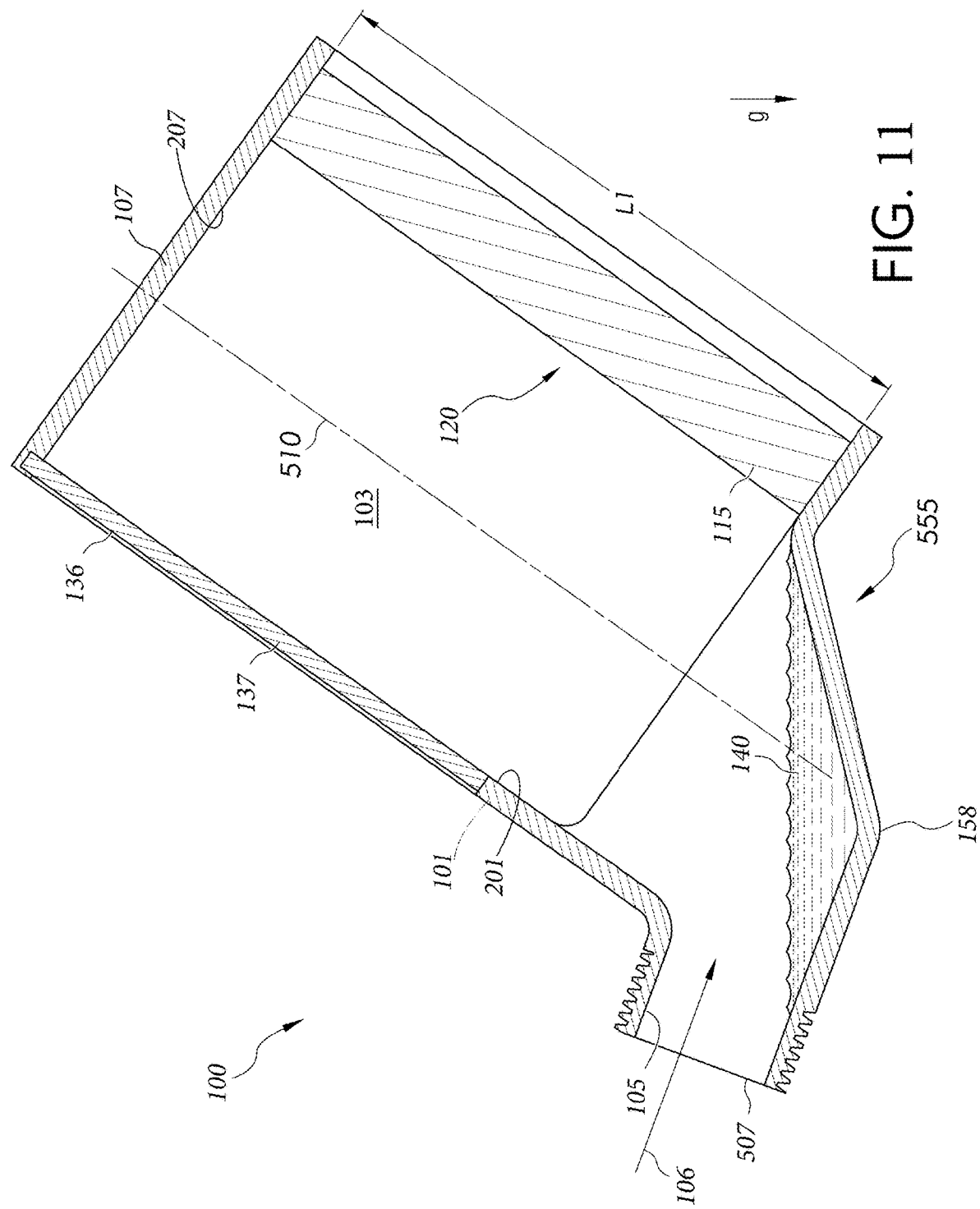
FIG. 11 is a cross-sectional view of an alternative embodiment of the cell culture vessel of FIG. 3 including a method of culturing cells in the fifth exemplary cell culture vessel in accordance with embodiments of the disclosure.

Methods of culturing cells in cell culture vessel 100 will now be described with reference to FIGS. 11-16. As shown in FIG. 11, in some embodiments, a method of culturing cells 150 (See FIG. 15) in the cell culture vessel 100 can include passing liquid (e.g., represented by arrow 106) through the aperture 105 from outside the vessel 100 into the cell culture chamber 103, thereby providing a predetermined amount of liquid 140 in the cell culture chamber 103. In embodiments, the method can be performed in a vessel with or without the optional dam 130.

Also shown is the bend 158 of the neck 112 of the vessel 100. In some embodiments, the method can include tilting the vessel 100 so that the bend 158 forms a low point in the neck 112. Liquid 140 introduced into the vessel can accumulate in the neck 112 at the bend 158. That is, the vessel can contain a predetermined amount of liquid 140 in the bend 158 of the neck 112, without liquid 140 contacting the microcavity array 115. As discussed more fully below, preventing liquid 140 from contacting one or more microcavities 120 of the cell culture surface 115 containing an array of microcavities 120, at this stage of the method, can provide several advantages that, for example, facilitate improved culturing of the cells 150 (See FIG. 15). Then the vessel can be tilted slowly back so that axis 510 is perpendicular to gravity "g", allowing the liquid 140 to slowly flow across the cell culture surface 115 having an array of microcavities 120, allowing the liquid to slowly fill the microcavities 120. This step is shown schematically in FIG. 12.

Figure 12:
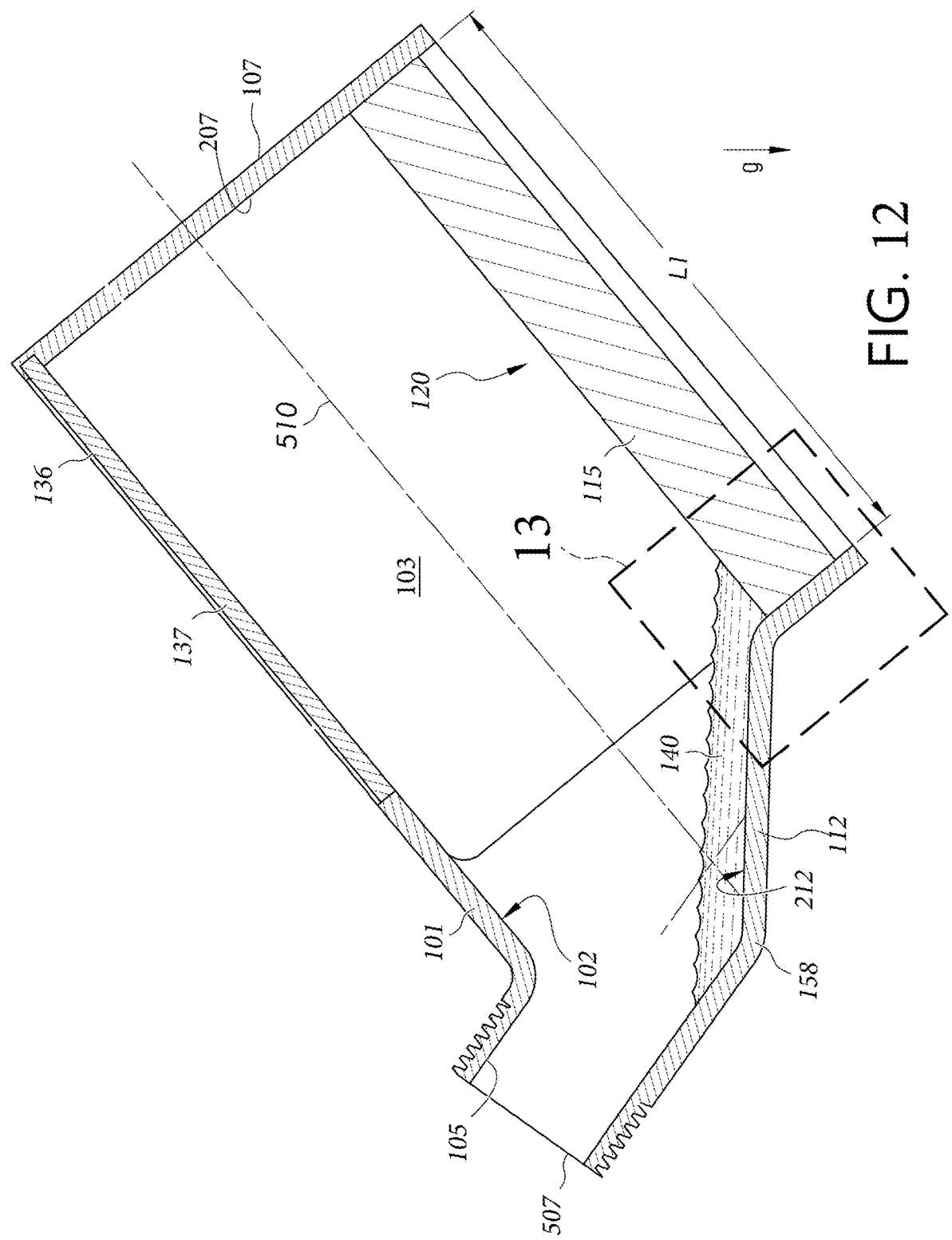
FIG. 12 shows a step of the method of culturing cells in the cell culture vessel of FIG. 11 in accordance with embodiments of the disclosure.
Figure 13:
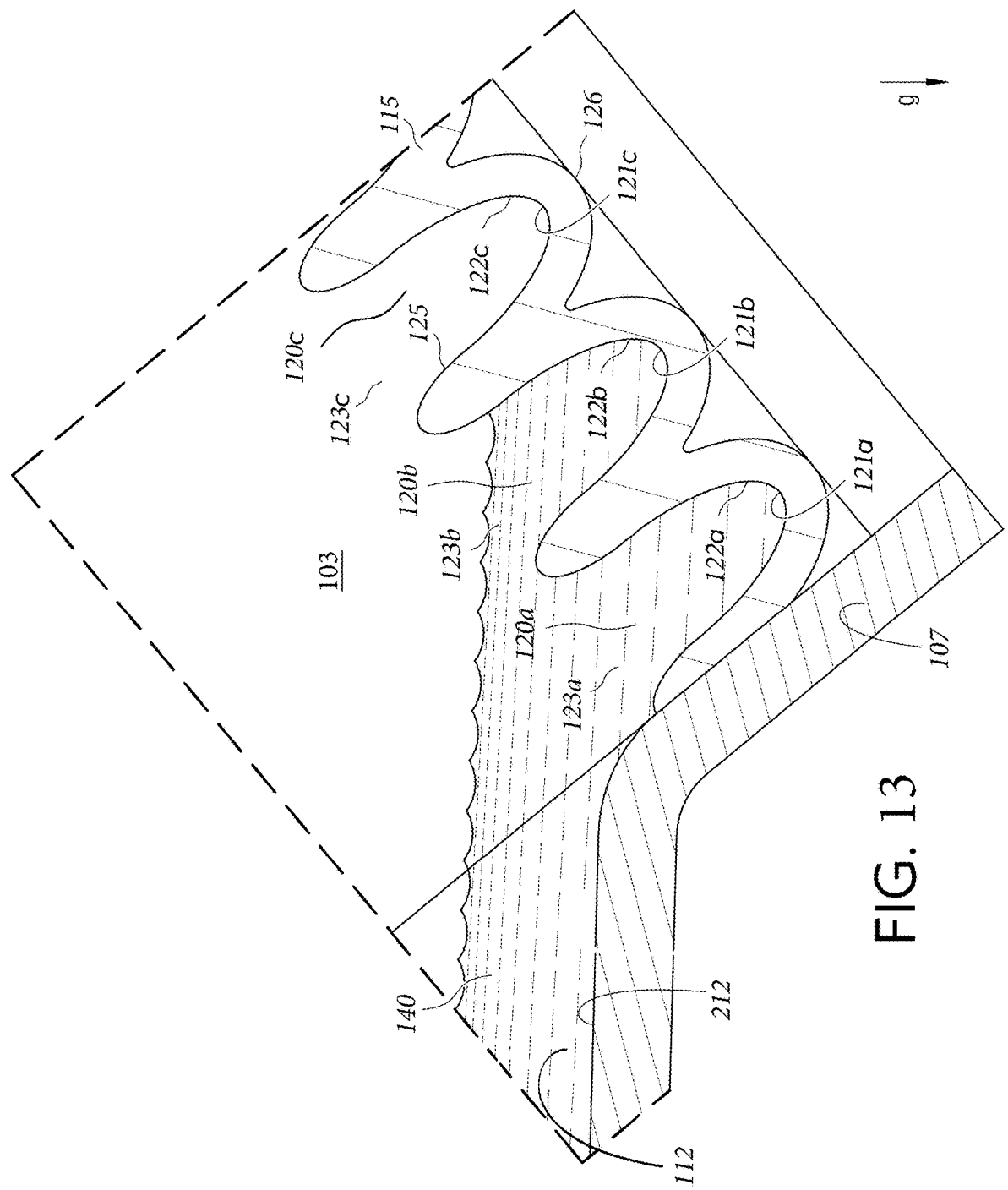
FIG. 13 is an enlarged schematic representation of a cell culture vessel taken at view 13 of FIG. 12 including a cell culture surface having a plurality of microcavities in accordance with embodiments of the disclosure.

For example, FIG. 13 illustrates an enlarged schematic representation of a cell culture vessel 100 taken at view 13 of FIG. 12 showing at least a portion of the liquid 140 flowing from the neck 112 on to the cell culture surface 115 along the length "L1" of the cell culture chamber 103 and entering microcavities 120a, 120b, 120c of the microcavity array 120. In some embodiments, the movement of the vessel 100 to cause the liquid to flow can be controlled and slow (e.g., performed during a duration of time on the order of minutes). For example, it has been observed that directly filling the microcavities 120a, 120b, 120c of the plurality of microcavities 120 with liquid (e.g., not based on the method of the disclosure) can result in bubbles forming in the microcavities. This slow introduction of liquid to the microcavities 120 allows liquid to flow into the microcavities with reduced bubble formation. Bubbles disrupt cell growth. Liquid media can have a high surface tension (it can be thick) and the microcavities 120 are very small. Without intending to be bound by theory, it is believed, when directly and quickly (e.g., performed during a duration of time on the order of seconds) filling the microcavities 120a, 120b, 120c with liquid, because of surface tension, bubbles may become trapped in the microcavities. However, by employing one or more features of the method of the disclosure, it has been observed that, for example, by introducing liquid into the bend 158 of the neck 112 and then slowly tilting the vessel 100 to it's cell culturing position (with the cell culture surface perpendicular to gravity "g", bubble formation can be reduced.

In addition, for long-term cell culture, media must be changed to ensure that the cells maintain a fresh supply of nutrients. This requires removing media and replacing the media while spheroids are in place in each microcavity 120. It is important not to dislodge the spheroids from the microcavities 120 during media changes. When a spheroid 150 "hops" out of its microcavity, it can settle into another, already occupied microcavity. When spheroids touch each other, they form irregular cellular conglomerates 801 (see FIGS. 35 and 36), leading to inhomogeneous cell culture.

In some embodiments, bend 158 of the neck 112 can abut the cell culture surface 115 and fluid 140 can flow from the bend 158 in the neck 112 and deposit into at microcavities 120a, 120b, 120c with controlled flow (e.g., reduced or no liquid splashing and reduced or no turbulent flow), thereby providing a steady flow of liquid depositing into the well 122a, 122b, 122c of the microcavities 120a, 120b, 120c through a portion of the respective opening 123a, 123b, 123c of the microcavities 120a, 120b, 120c while displacing gas from the well 122a, 122b, 122c. In embodiments, the cell culture surface 115 extends from wall 107 to wall 107. In embodiments, the cell culture surface 115 does not have any flat areas. That is, the cell culture surface is an array of microcavities from wall to wall with no border, no flat areas between the cell culture surface and walls 107. In embodiments, the cell culture surface consisting essentially of a plurality of microcavities. In embodiments, there no flat areas in the cell culture chamber for cells to settle on. This is important to ensure that cells do not settle in the cell culture chamber outside of the microwells. When cells settle outside of microwells, on flat areas outside the cell culture surface, cells can grow as irregular cellular conglomerates, and create an inhomogeneous population of multicellular 3D structures in the vessel. In embodiments, a cell culture surface consisting essentially of a plurality of microcavities. When cells settle outside of microwells, on flat areas outside the cell culture surface, cells can grow as irregular cellular conglomerates 801 (See FIGS. 35A and 35B, 36A and 36B), and create an inhomogeneous population of multicellular 3D structures in the vessel. In embodiments, a cell culture surface consisting essentially of a plurality of microcavities.

In embodiments, the cell culture surface 115 extends from wall 107 to wall 107. In embodiments, the cell culture surface 115 does not have any flat areas. That is, the cell culture surface is an array of microcavities 120 extending from wall to wall with no border, no flat areas between the cell culture surface and walls 107. In embodiments, the cell culture surface consisting essentially of a plurality of microcavities. In embodiments, there no flat areas in the cell culture chamber for cells to settle on. This is important to ensure that cells do not settle in the cell culture chamber outside of the microwells. When cells settle outside of microwells, on flat areas outside the cell culture surface, cells can grow as irregular cellular conglomerates 801 (See FIGS. 35A and 35B, 36A and 36B), and create an inhomogeneous population of multicellular 3D structures in the vessel. In embodiments, a cell culture surface consisting essentially of a plurality of microcavities.

Figure 14:
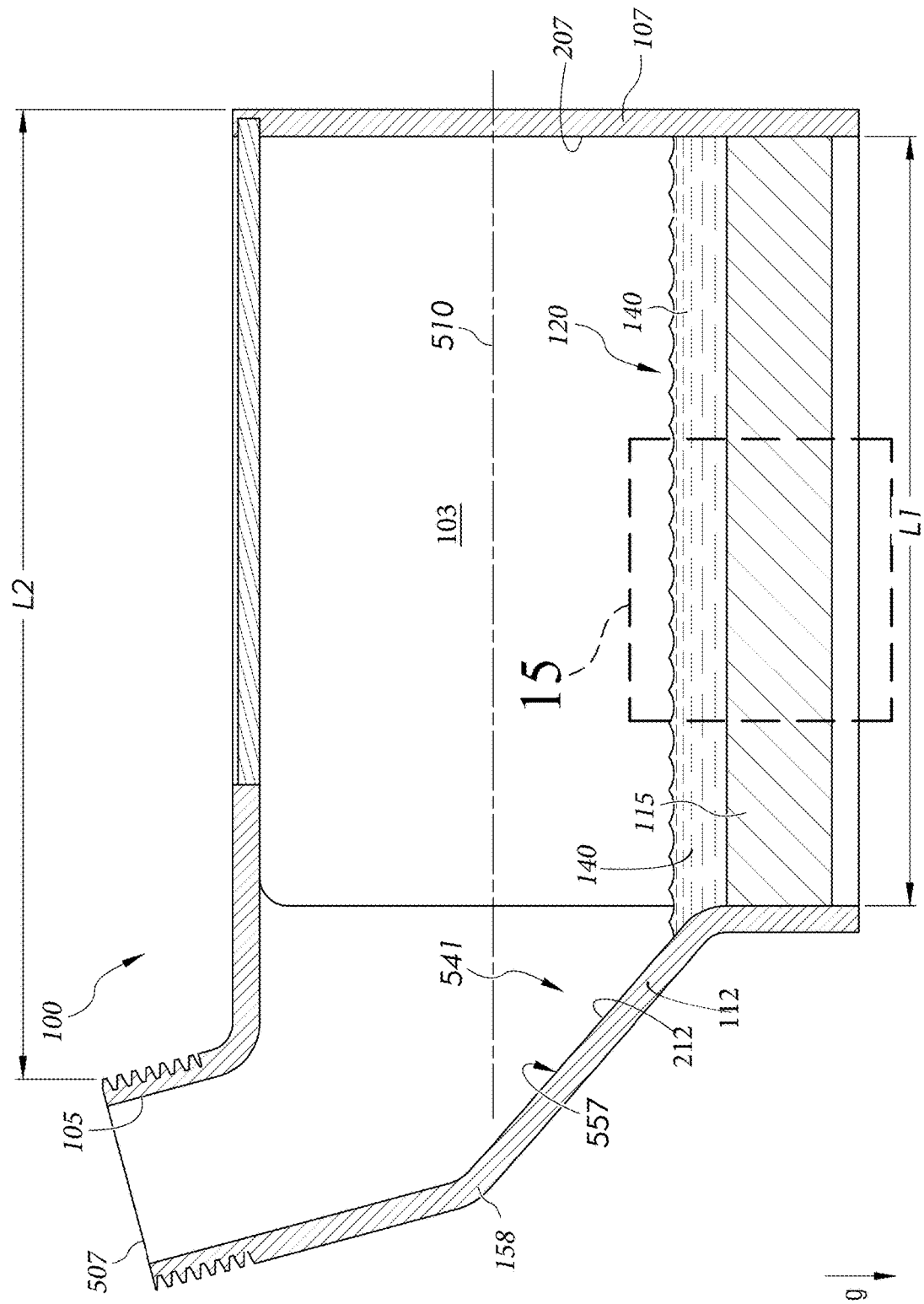
FIG. 14 shows a step of the method of culturing cells in the cell culture vessel of FIG. 11 in accordance with embodiments of the disclosure.
Figure 15:
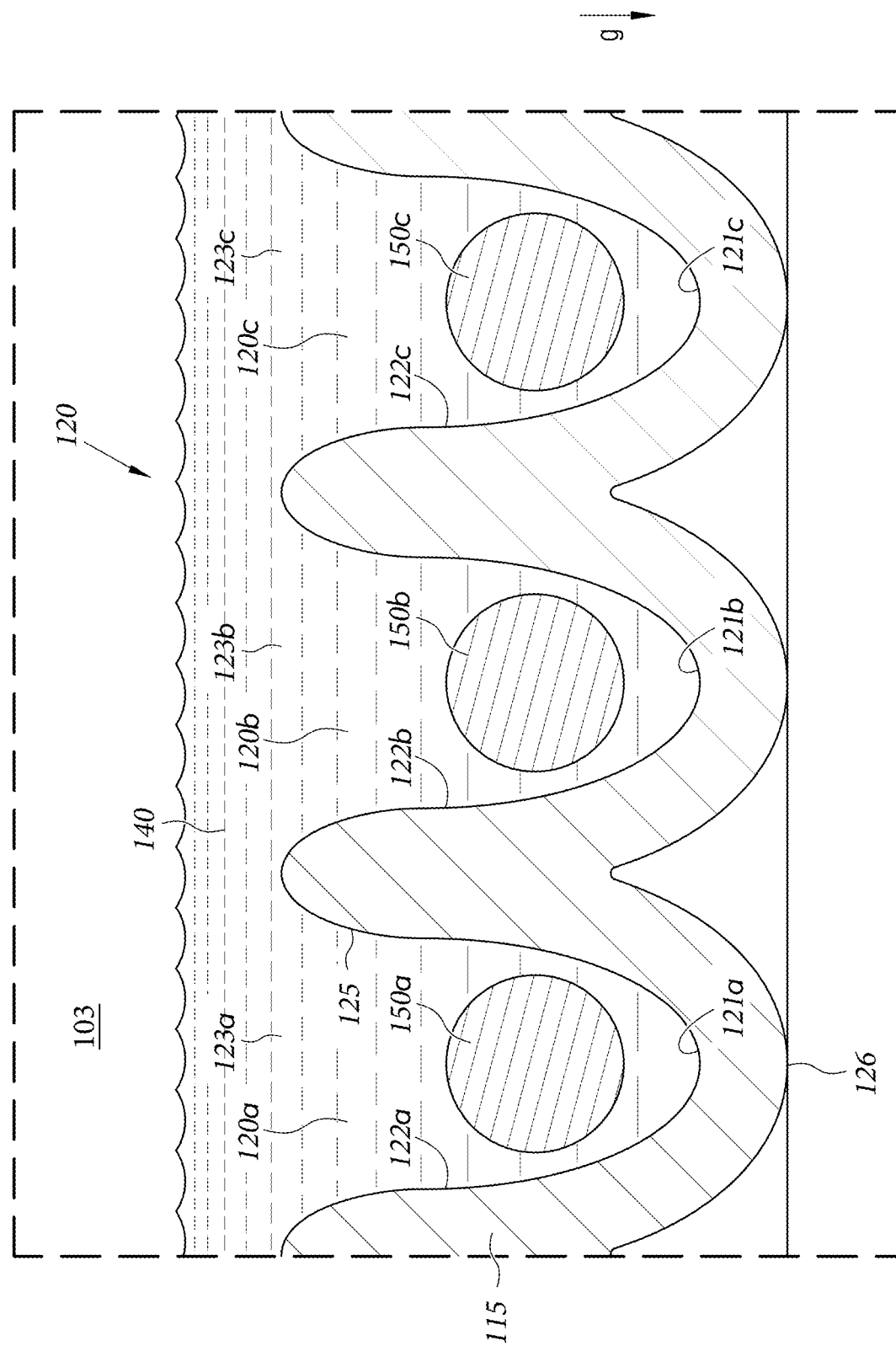
FIG. 15 is an enlarged schematic representation of a cell culture vessel taken at view 15 of FIG. 14 including a cell culture surface having a plurality of microcavities and a method of culturing cells in at least one microcavity of the plurality of microcavities in accordance with embodiments of the disclosure.

As shown in FIG. 14, in some embodiments, the liquid 140 can be caused to flow from the neck 112 over the entire cell culture surface 115 based at least on the movement of the vessel 100. Additionally, FIG. 15 illustrates an enlarged schematic representation of a cell culture vessel 100 taken at view 15 of FIG. 14 including a method of culturing cells 150 in the cell culture vessel 100. For example, in some embodiments, the method can include culturing cells 150 (e.g., spheroid 150a, spheroid 150b, spheroid 150c) in the at least one microcavity 120a, 120b, 120c of the plurality of microcavities 120 after depositing the at least a portion of the predetermined amount of liquid 140 in the at least one microcavity 120a, 120b, 120c. As shown in FIG. 14 and FIG. 15, in some embodiments, the axis 510 of the vessel 100 can be substantially perpendicular relative to the direction of gravity "g" while culturing cells 150 in the microcavities 120.

Figure 16:
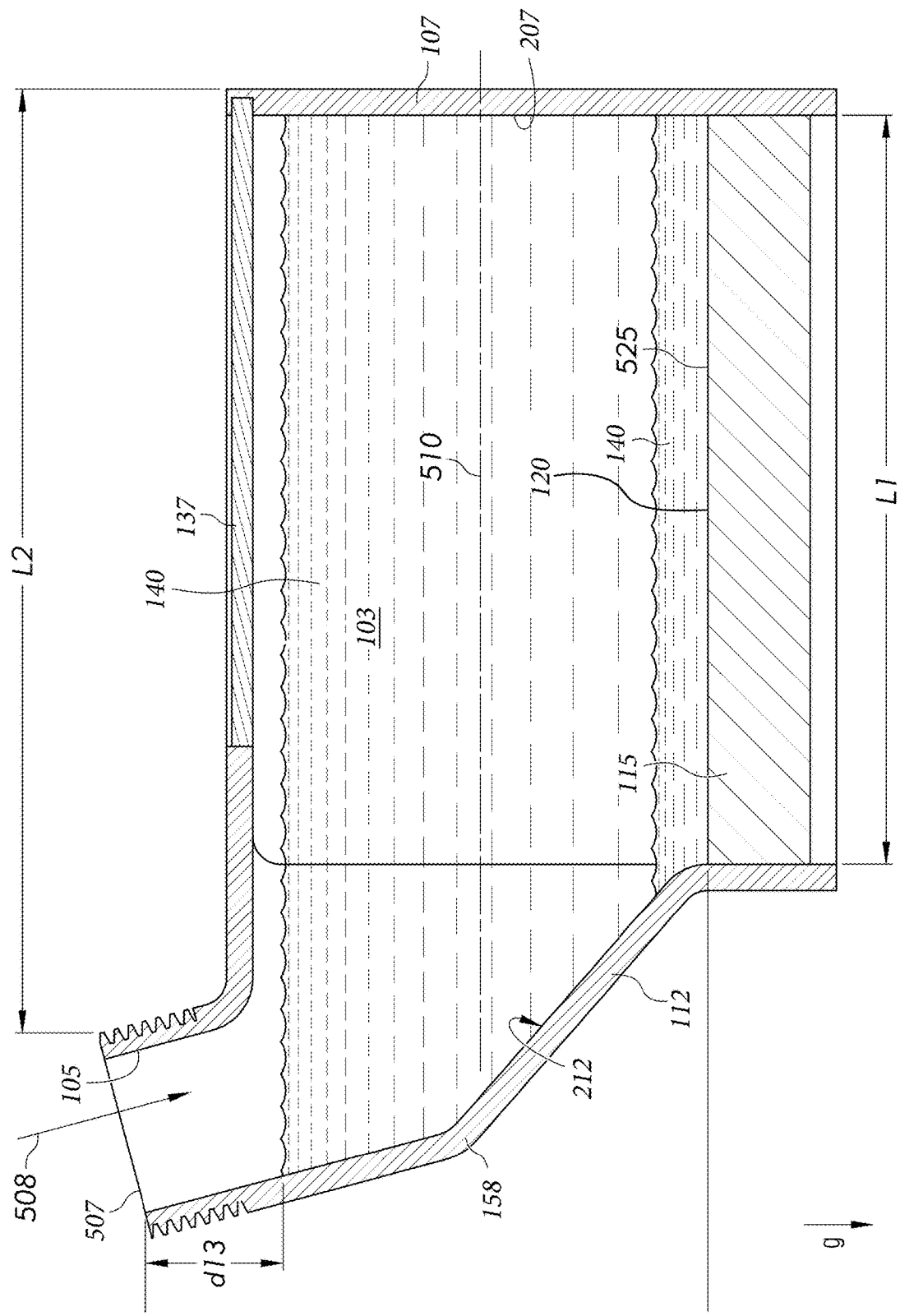
FIG. 16 shows a step of the method of culturing cells in the cell culture vessel of FIG. 4 in accordance with embodiments of the disclosure.

As shown schematically in FIG. 16, in some embodiments, the method can further include adding additional liquid media 140 (as shown by arrow 508) to the cell culture chamber 103. For example, in some embodiments, while culturing cells 150 (See FIG. 15) in the cell culture vessel 100, liquid media 140 (cell food, liquid containing nutrients) can be added to the cell culture chamber 103. Because the port 105 is raised and facing up, liquid 140 can be added to the vessel up to a distance "d13" from lowest point of the aperture 507 of the port 105. That is, in embodiments, the vessel can be filled right up to the lid 137 or top 101 of the vessel 100. In this way, the cell culture chamber 103 can contain larger volume of liquid 140 than it would be able to contain if the port were arranged lower with respect to the top 101 of the vessel 100.

Figure 17:
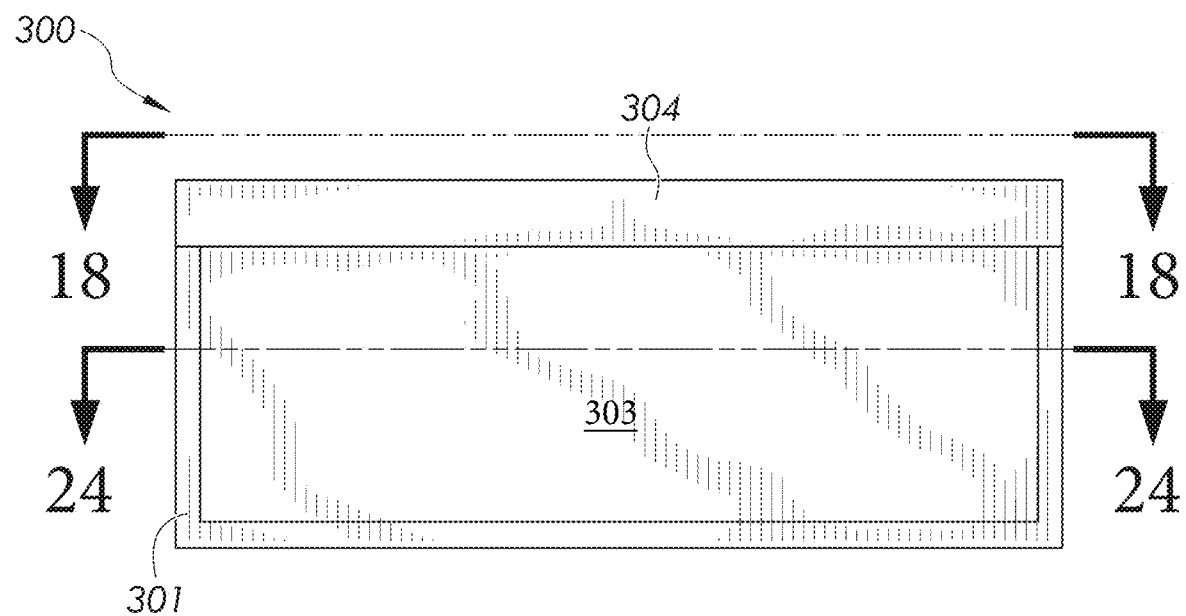
FIG. 17 illustrates a side view of a cell culture vessel in accordance with embodiments of the disclosure.
Figure 18:
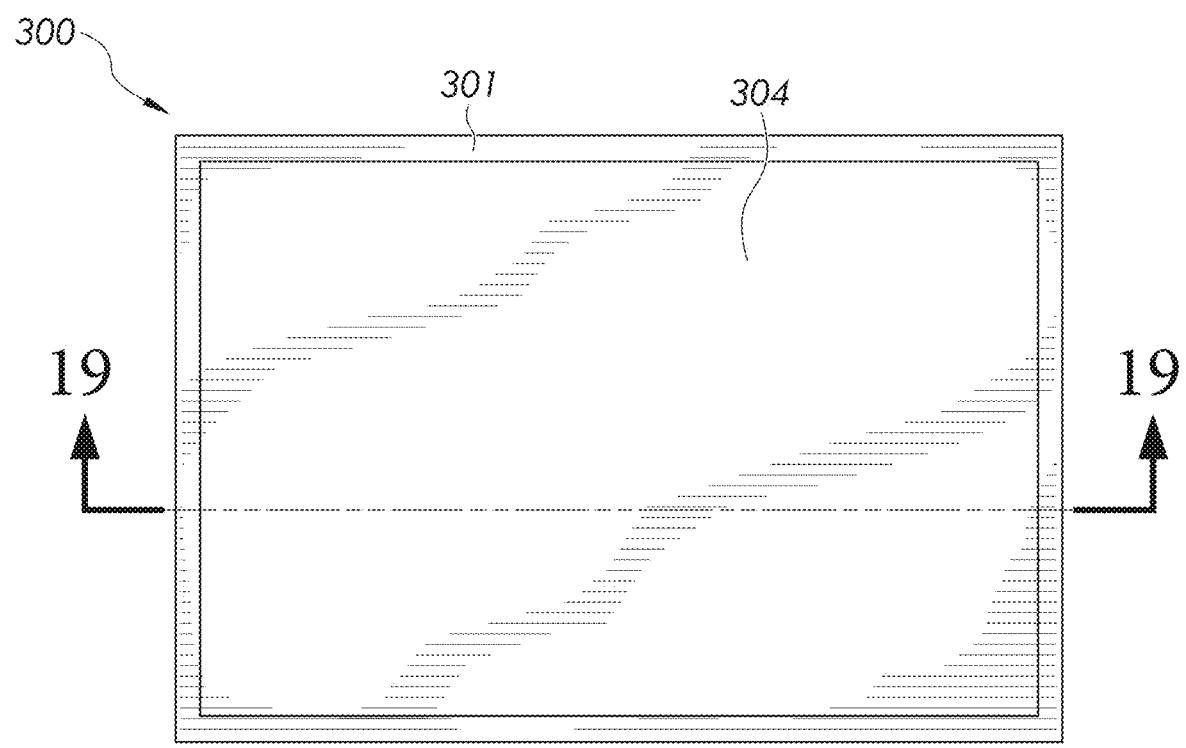
FIG. 18 is a plan view of a cell culture vessel along line 18-18 of FIG. 17 in accordance with embodiments of the disclosure.

In an additional embodiment of a cell culture vessel 300 and methods of culturing cells in the cell culture vessel 300 will now be described with reference to FIGS. 17-34. While the embodiments shown in FIGS. 17-34 show an embodiments without a necked opening or a port, it is to be understood that the embodiments shown in FIGS. 17-34 can be incorporated into the embodiments illustrated in FIGS. 1-16, a vessel with a port. For example, FIG. 17 schematically illustrates a side view of cell culture vessel 300, and FIG. 18 schematically illustrates a plan view of the vessel 300 along line 18-18 of FIG. 17. In some embodiments, the cell culture vessel 300 can include a wall 301 and a lid 304. In the drawing figures, the vessel 300 is illustrated as being manufactured from a clear (e.g., transparent) material; although, in some embodiments, the vessel 300 can, alternatively, be manufactured from a semi-transparent, semi-opaque, or opaque material without departing from the scope of the disclosure. In some embodiments, the lid 304 can be oriented to cover an opening of the vessel 300 to at least one of seal and block the opening, thereby obstructing a path into the cell culture chamber 303 from outside the vessel 300 through the opening. For clarity purposes, the lid 304 is removed and, therefore, not shown in other drawing figures, although it is to be understood that the lid 304 can be provided and selectively added to or removed from the opening of the vessel 300, in some embodiments, without departing from the scope of the disclosure. In some embodiments, the lid 304 can include a filter that permits the transfer of gas in to and/or out of a cell culture chamber 303 (See FIG. 19) of the vessel 300. For example, in some embodiments, the lid 304 can include a gas-permeable filter oriented to regulate a pressure of gas within the cell culture chamber 303, thereby preventing pressurization (e.g., overpressurization) of the cell culture chamber 303 relative to a pressure of the environment (e.g., atmosphere) outside the vessel 300.

Figure 19:
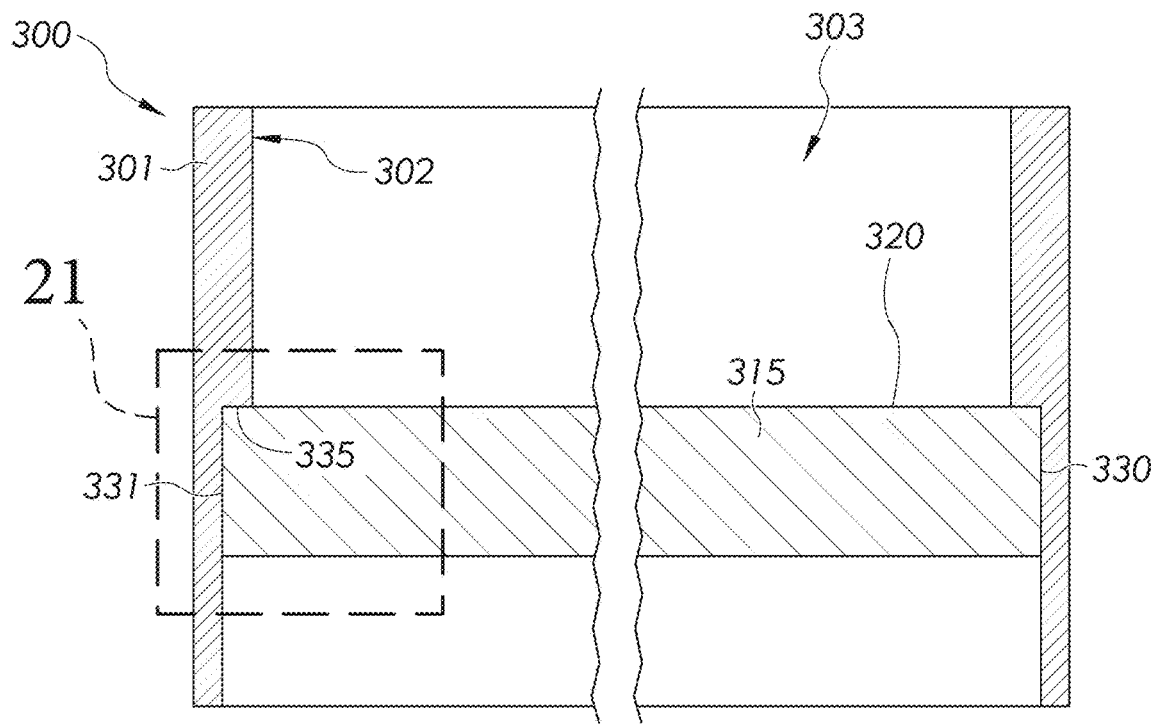
FIG. 19 is a cross-sectional view of an embodiment of a cell culture vessel along line 19-19 of FIG. 18 including a recess in accordance with embodiments of the disclosure.
Figure 20:
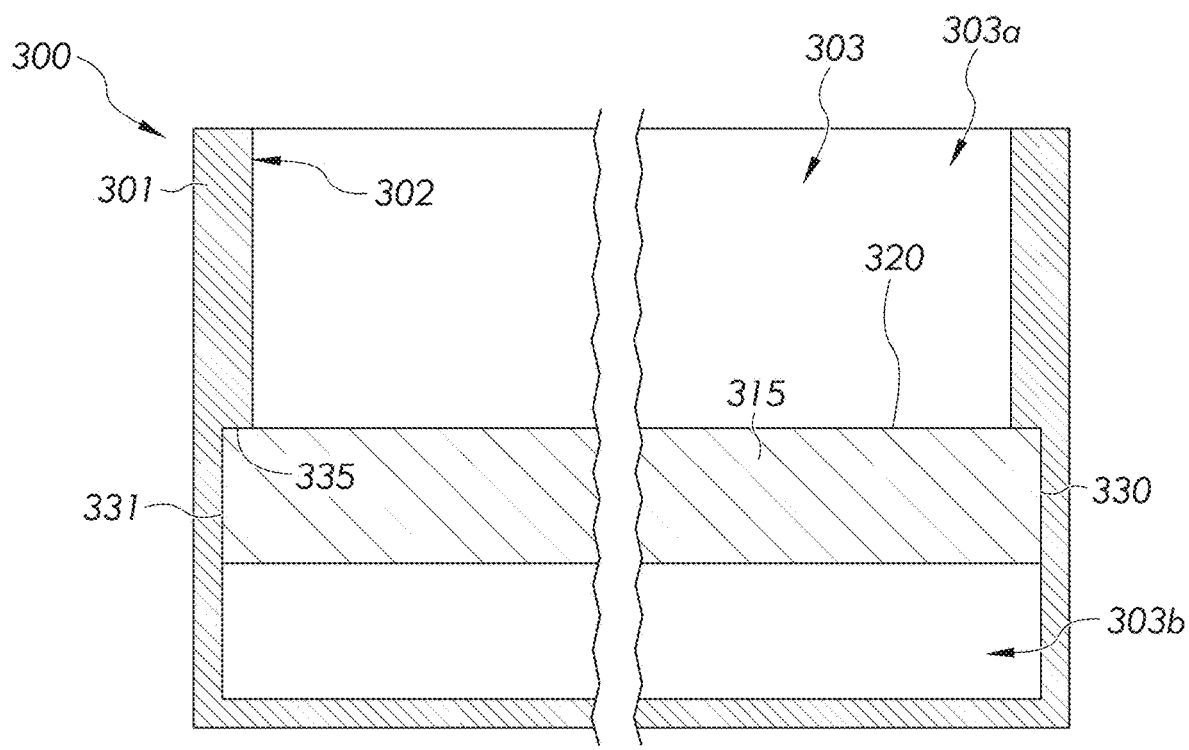
FIG. 20 is a cross-sectional view of an alternative embodiment of the cell culture vessel of FIG. 29 including a recess in accordance with embodiments of the disclosure.
Figure 25:
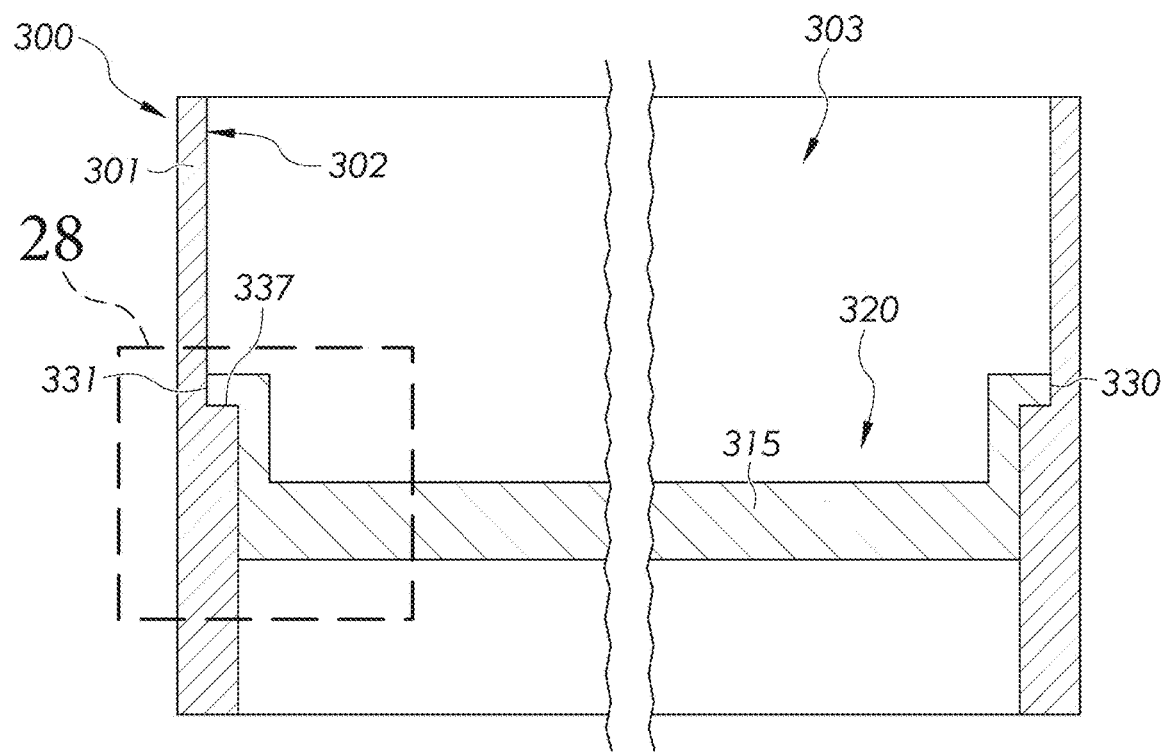
FIG. 25 shows a cross-sectional view of an exemplary cell culture vessel of FIG. 19 including a protrusion in accordance with embodiments of the disclosure.
Figure 26:
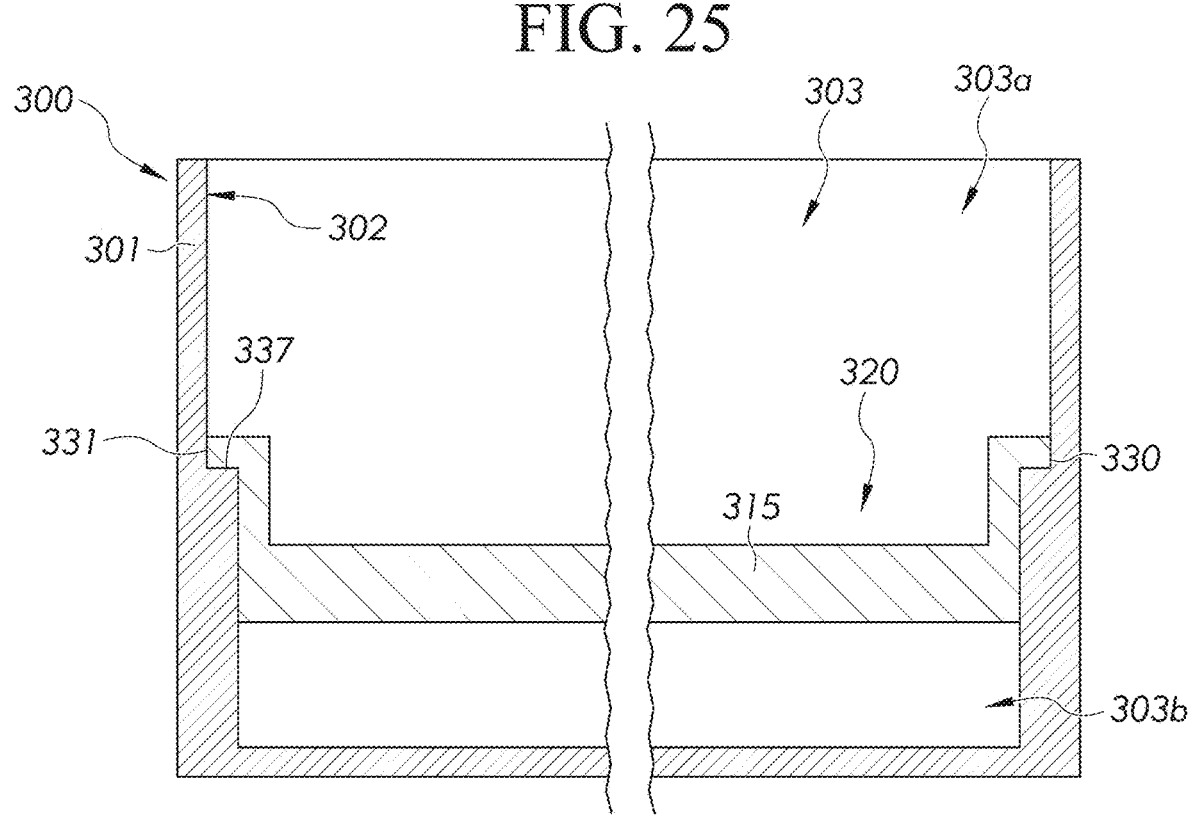
FIG. 26 is a cross-sectional view of a cell culture vessel including a protrusion of FIG. 25 in accordance with embodiments of the disclosure.

FIG. 19 shows a cross-sectional view of an exemplary embodiment of the cell culture vessel 300 along line 19-19 of FIG. 18, and FIG. 20 shows an alternative exemplary embodiment of the cross-sectional view of the cell culture vessel 300 of FIG. 19. Additionally, FIG. 25 shows an alternative exemplary embodiment of the cross-sectional view of the cell culture vessel 300 of FIG. 18, and FIG. 26 shows an alternative exemplary embodiment of the cross-sectional view of the cell culture vessel 300 of FIG. 25. In some embodiments, the wall 301 can include an inner surface 302, and the vessel 300 can include a cell culture surface 315 including a plurality of microcavities 320. As shown in FIG. 19 and FIG. 25, in some embodiments, the cell culture surface 315 and the inner surface 302 of the wall 301 define the cell culture chamber 303 of the vessel 300. Alternatively, as shown in FIG. 20 and FIG. 26, in some embodiments, the inner surface 302 of the wall 301 can define a cell culture chamber 303 of the vessel 300 including, for example, a first region 303a and a second region 303b, and the cell culture surface 315 can be positioned in the cell culture chamber 303, between the first region 303a and the second region 303b.

Figure 24:
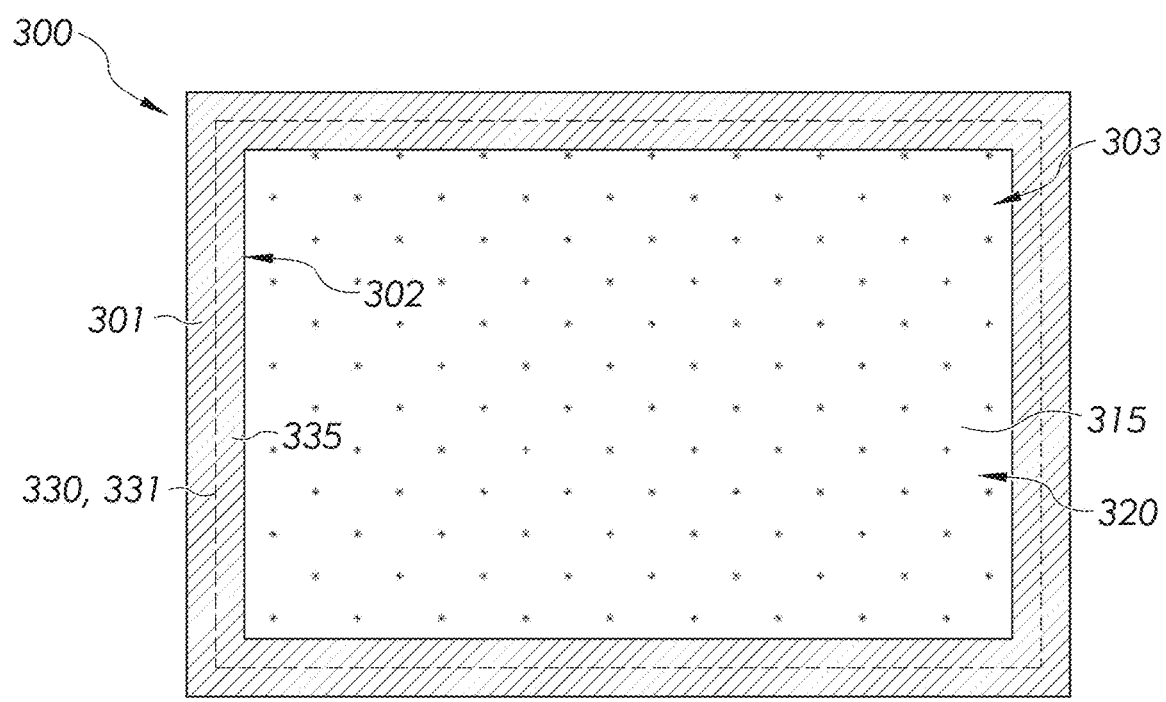
FIG. 24 shows a cross-sectional view of an exemplary embodiment of the third exemplary cell culture vessel along line 24-24 of FIG. 17 including a recess in accordance with embodiments of the disclosure.
Figure 29:
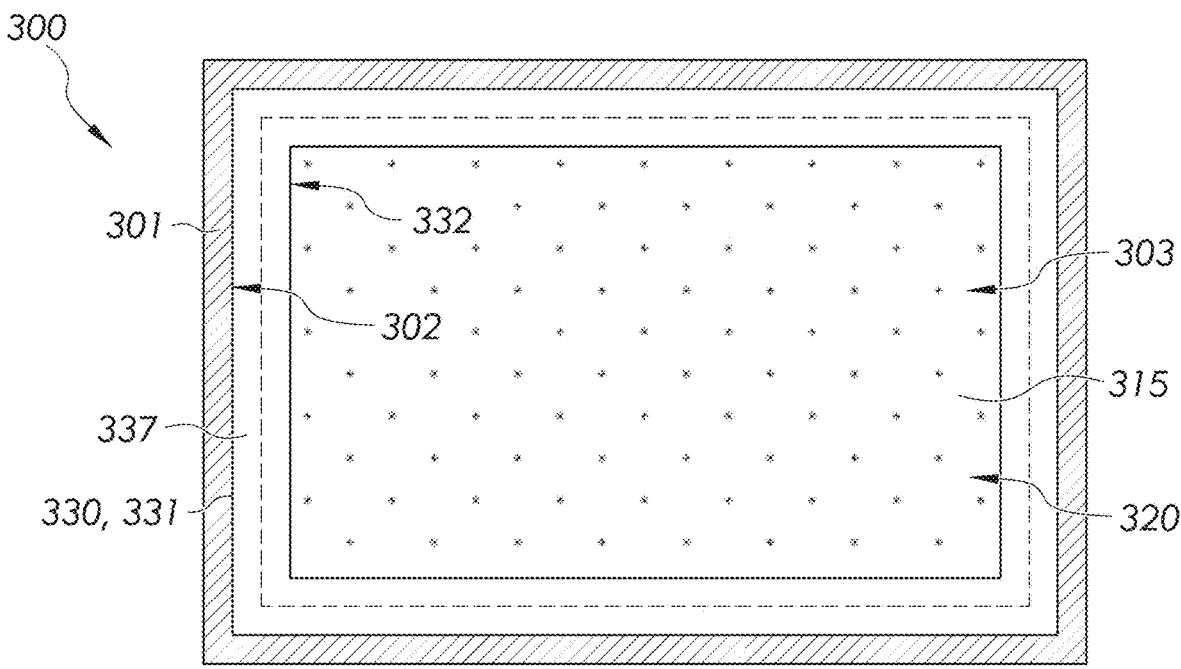
FIG. 29 is a cross-sectional view of a cell culture vessel of FIG. 24 including a protrusion in accordance with embodiments of the disclosure.

As shown in FIG. 19 and FIG. 20, in some embodiments, an outer perimeter 330 of the cell culture surface 315 can surround the plurality of microcavities 320, and at least a portion 331 of the outer perimeter 330 can be positioned in a recess 335 of the inner surface 302 of the wall 301 of the vessel 300. For example, FIG. 24 shows an exemplary cross-section view of the vessel 300 taken along line 24-24 of FIG. 30, where the entire outer perimeter 330 laterally circumscribes the plurality of microcavities 320 and the entire outer perimeter 330 is positioned in the recess 335. Alternatively, as shown in FIG. 25 and FIG. 26, in some embodiments, the outer perimeter 330 of the cell culture surface 315 can surrounds the plurality of microcavities 320, and at least a portion 331 of the outer perimeter 330 can be positioned on a protrusion 337 of the inner surface 302 of the wall 301 of the vessel 300. For example, FIG. 29 shows an alternative exemplary embodiment of the cross-sectional view of the third exemplary cell culture vessel 300 of FIG. 24, where the entire outer perimeter 330 laterally circumscribes the plurality of microcavities 320 and the entire outer perimeter 330 is positioned on the recess 335 protrusion 337. Throughout the disclosure, "surrounds" means that, in a top or bottom view in a direction perpendicular to a major feature of the cell culture surface 315, for example, an outer periphery defined by the first feature surrounds an outer periphery defined by the second feature. Thus, for example, as shown in the view of FIG. 24 and FIG. 42, an outer periphery (defined by the outer perimeter 330) of the cell culture surface 315 surrounds an outer periphery (defined by the plurality of microcavities 320) of the cell culture surface 315.

In embodiments, the cell culture surface 315 extends from wall 301 to wall 301. In embodiments, the cell culture surface 315 does not have any flat areas. That is, the cell culture surface is an array of microcavities 320 extending from wall to wall with no border, no flat areas between the cell culture surface and walls 301. In embodiments, the cell culture surface consisting essentially of a plurality of microcavities. In embodiments, there no flat areas in the cell culture chamber for cells to settle on. This is important to ensure that cells do not settle in the cell culture chamber outside of the microwells. When cells settle outside of microwells, on flat areas outside the cell culture surface, cells can grow as irregular cellular conglomerates 801 (See FIGS. 35A and 35B, 36A and 36B), and create an inhomogeneous population of multicellular 3D structures in the vessel. In embodiments, a cell culture surface consisting essentially of a plurality of microcavities.

Figure 21:
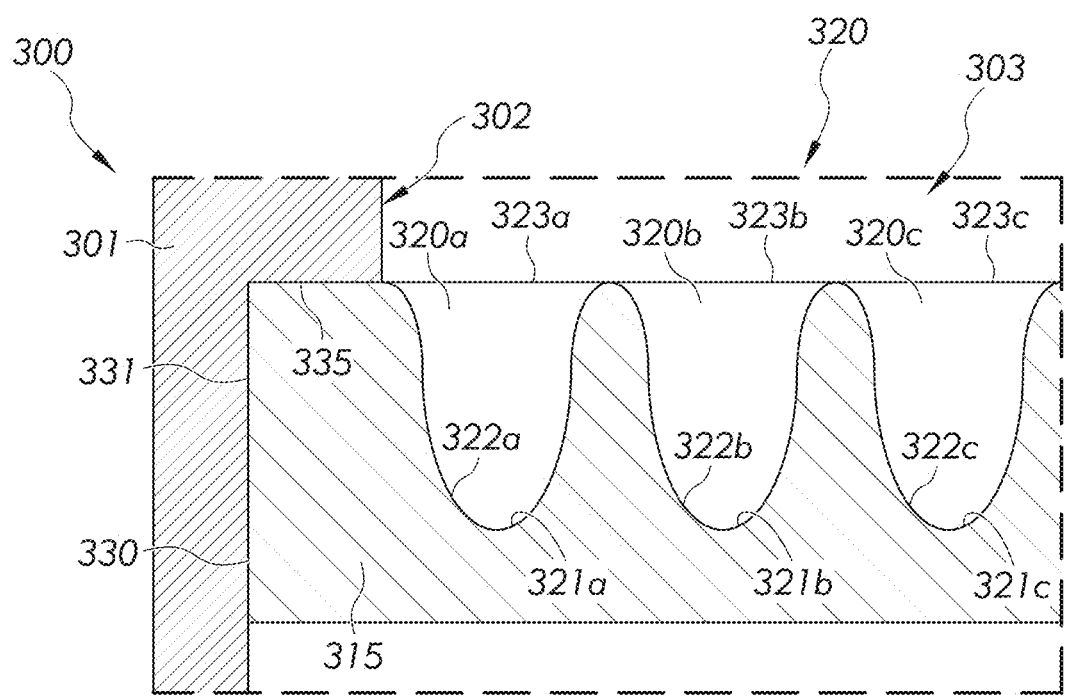
FIG. 21 is an enlarged schematic illustration of a portion of the third exemplary cell culture vessel taken at view 21 of FIG. 19 including a cell culture surface including a plurality of microcavities positioned in a recess in accordance with embodiments of the disclosure.
Figure 22:
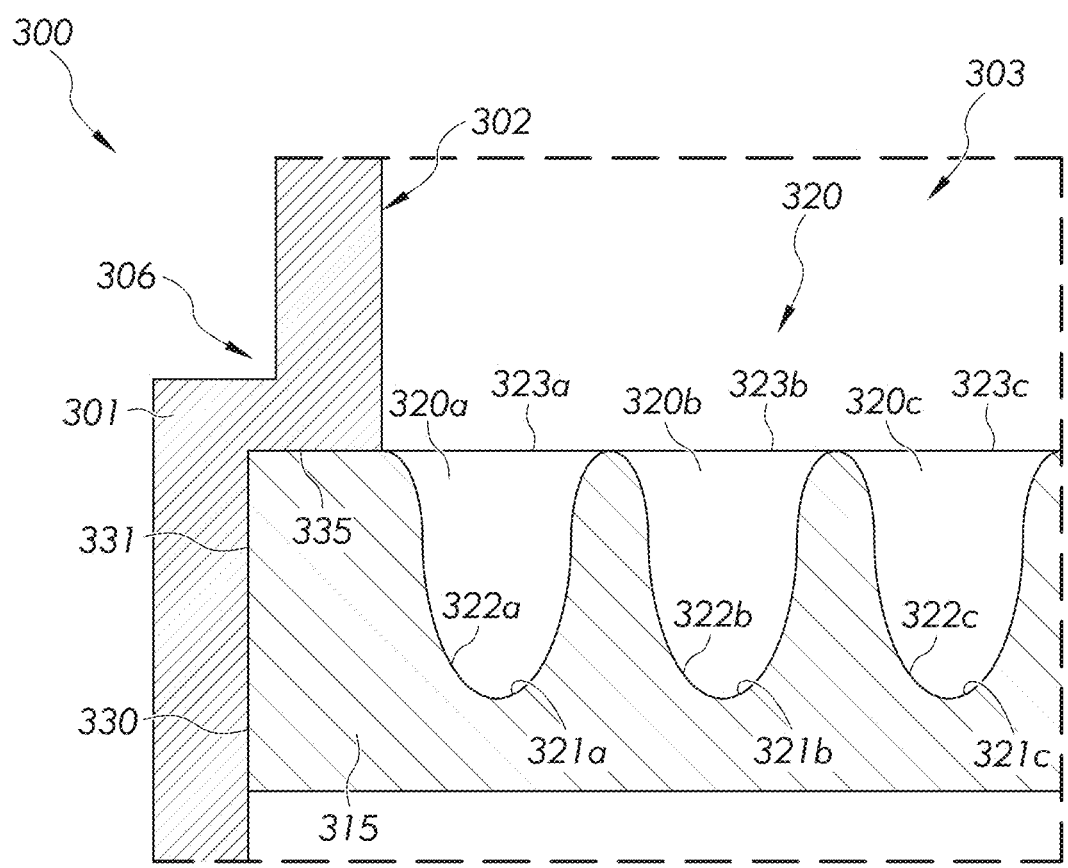
FIG. 22 shows an alternative embodiment of the portion of the cell culture vessel having a cell culture surface having a plurality of microcavities positioned in a recess of FIG. 21 including a stepped portion in accordance with embodiments of the disclosure.
Figure 23:
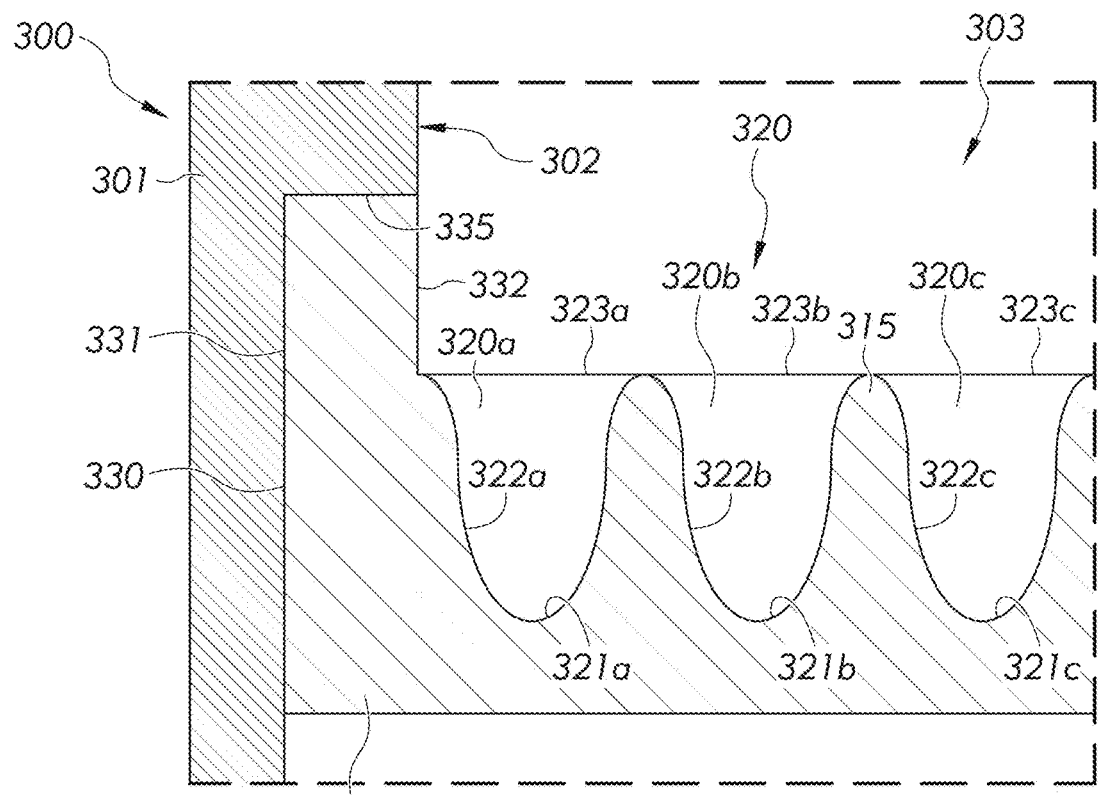
FIG. 23 shows an alternative embodiment of the cell culture vessel having a cell culture surface including a plurality of microcavities positioned in a recess of FIG. 21 including a peripheral surface of the cell culture surface in accordance with embodiments of the disclosure.
Figure 27:
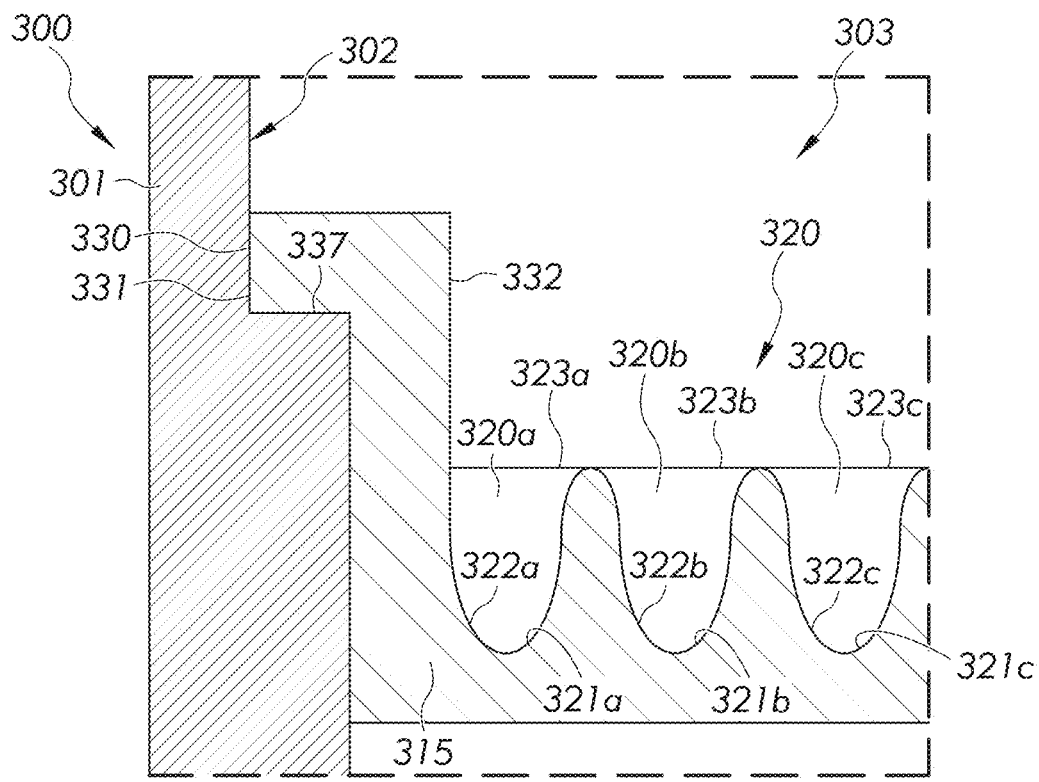
FIG. 27 is an enlarged schematic representation of an embodiment of a portion of the cell culture vessel taken at view 28 of FIG. 25 including a cell culture surface including a plurality of microcavities positioned on a protrusion in accordance with embodiments of the disclosure.
Figure 28:
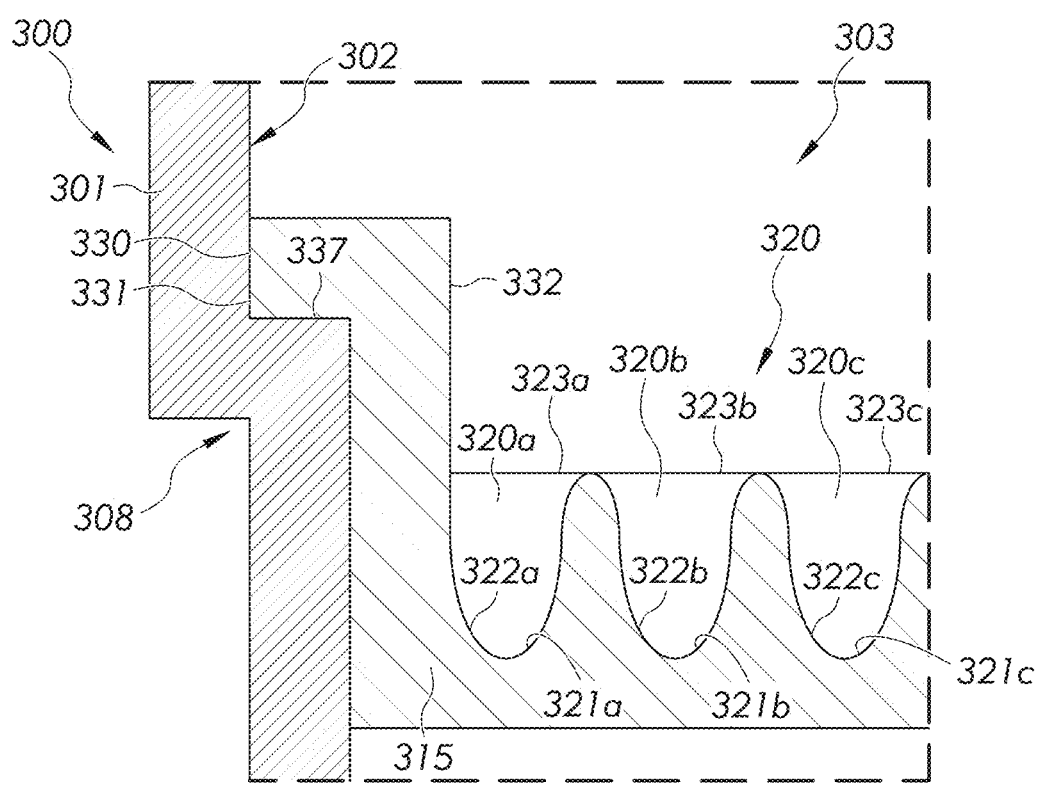
FIG. 28 shows an embodiment of the portion of the cell culture vessel including a cell culture surface including a plurality of microcavities positioned on a protrusion of FIG. 27 including a stepped portion in accordance with embodiments of the disclosure.

FIGS. 21-23 show exemplary embodiments of an enlarged view of a portion of the vessel 300 taken at view 21 of FIG. 19 including the at least a portion 331 of the outer perimeter 330 of the cell culture surface 315 positioned in the recess 335. Similarly, FIG. 27 and FIG. 28 show exemplary embodiments of an enlarged view of the vessel 300 taken at view 28 of FIG. 25 including the at least a portion 331 of the outer perimeter 330 positioned on the protrusion 337. In some embodiments, each microcavity 320a, 320b, 320c of the plurality of microcavities 320 can include a concave surface 321a, 321b, 321c defining a well 322a, 322b, 322c and an opening 323a, 323b, 323c Liquid enters and exits the microcavities through the openings 323a, 323b, 323c. In some embodiments, the cell culture surface 315 can be attached to the wall 301 of the vessel 300. For example, in some embodiments the cell culture surface 315 can be attached to the wall 301 of the vessel 300 with an adhesive (not shown), a solvent (not shown), or a fastener (not shown), by welding (laser welding or ultrasonic welding) or the wall and the cell culture surface 315 can be molded together. In addition or alternatively, in some embodiments the cell culture surface 315 can be attached to the inner surface 302 of the wall 301 of the vessel 300 based at least in part on, for example, operation of a plastic welding process, a laser welding process, an ultrasonic welding process. In some embodiments, at least one of the wall 301 and the outer perimeter 330 can include an energy director (not shown) to facilitate bonding of the cell culture surface 315 to the wall 301 of the vessel 300 based at least in part on operation of the plastic welding process.

Additionally, as shown in FIG. 22, in some embodiments, the vessel 300 can include a stepped portion 306 extending outward from the cell culture surface 315 and forming the recess 335. In some embodiments, the stepped portion 306 can increase at least one of a volume of the cell culture chamber 303 and a quantity of microcavities 320a, 320b, 320c of the plurality of microcavities 320 within the cell culture chamber 303. In addition or alternatively, the stepped portion 306 can provide a relatively larger recess 335 without increasing a thickness of the wall 301 of the vessel 300 as compared to the corresponding recess 335 and wall 301 thickness shown, for example, in FIG. 21. In some embodiments, the recess 335 formed by the stepped portion 306 can be oriented to accommodate the at least a portion 331 of the outer perimeter 330 of the cell culture surface 315 positioned in the recess 335. Similarly, as shown in FIG. 28, in some embodiments, the vessel 300 can include a stepped portion 308 extending inward toward the cell culture surface 315 and forming the protrusion 337. In some embodiments, the stepped portion 308 can provide a relatively larger protrusion 337 without increasing a thickness of the wall 301 of the vessel 300 as compared to the corresponding protrusion 337 and wall 301 thickness shown, for example, in FIG. 28. In some embodiments, the protrusion 337 formed by the stepped portion 308 can be oriented to accommodate the at least a portion 331 of the outer perimeter 330 of the cell culture surface 315 positioned on the protrusion 337.

In embodiments, the cell culture surface 315 extends from wall 301 to wall 301. In embodiments, the cell culture surface 315 does not have any flat areas. That is, the cell culture surface is an array of microcavities 320 extending from wall to wall with no border, no flat areas between the cell culture surface and walls 301. In embodiments, the cell culture surface consisting essentially of a plurality of microcavities. In embodiments, there no flat areas in the cell culture chamber for cells to settle on. This is important to ensure that cells do not settle in the cell culture chamber outside of the microwells. When cells settle outside of microwells, on flat areas outside the cell culture surface, cells can grow as irregular cellular conglomerates 801 (See FIGS. 35A and 35B, 36A and 36B), and create an inhomogeneous population of multicellular 3D structures in the vessel. In embodiments, a cell culture surface consisting essentially of a plurality of microcavities.

Additionally, as shown in FIG. 23, FIG. 25, and FIG. 28, in some embodiments, the at least a portion 331 of the outer perimeter 330 of the cell culture surface 315 can be spaced from the portion of the cell culture surface 315 including the openings 323a, 323b, 323c of the microcavities 320a, 320b, 320c in a direction away from the concave surface 321a, 321b, 321c of each microcavity 320a, 320b, 320c of the plurality of microcavities 320. For example, in some embodiments, the cell culture surface 315 can include a peripheral surface 332 extending from the at least a portion 331 of the outer perimeter 330 to the portion of the cell culture surface 315 including the openings 323a, 323b, 323c. In some embodiments, the peripheral surface 332 can include a vertical orientation (e.g., extending in the direction of gravity); however, in some embodiments, the peripheral surface 332 can be inclined relative to the direction of gravity to, for example, direct cells toward the openings 323a, 323b, 323c of the microcavities 320a, 320b, 320c.

Moreover, by positioning the at least a portion 331 of the outer perimeter 330 of the cell culture surface 315 in the recess 335, in some embodiments, the opening 323a of the microcavity 320a, for example, can be positioned to abut the inner surface 302 of the wall 301 at the location of the recess 335. For example, in some embodiments, the opening 323a of the microcavity 320a can be flush with the inner surface 302 of the wall 301 such that cells suspended in a liquid will fall (e.g., based at least on the force of gravity) and/or be directed by the inner surface 302 into the well 322a of the microcavity 320a without settling on or adhering to a surface of the vessel 300. Likewise, by positioning the at least a portion 331 of the outer perimeter 330 of the cell culture surface 315 on the protrusion 337, in some embodiments, the opening 323a of the microcavity 320a, for example, can be positioned to abut the peripheral surface 332 of the cell culture surface 315 with the outer perimeter 330 supported by the protrusion 337. For example, in some embodiments, the opening 323a of the microcavity 320a can be flush with the peripheral surface 332 of the cell culture surface 315 such that cells suspended in a liquid will fall (e.g., based at least on the force of gravity) and/or be directed by the peripheral surface 332 into the well 322a of the microcavity 320a without settling on or adhering to any other surface of the vessel 300. In embodiments, the cell culture surface 315 extends from wall 301 to wall 301. In embodiments, the cell culture surface 115 does not have any flat areas. That is, the cell culture surface is an array of microcavities 320 extending from wall to wall with no border, no flat areas between the cell culture surface and walls 301. In embodiments, the cell culture surface consisting essentially of a plurality of microcavities. In embodiments, there no flat areas in the cell culture chamber for cells to settle on. This is important to ensure that cells do not settle in the cell culture chamber outside of the microwells. When cells settle outside of microwells, on flat areas outside the cell culture surface, cells can grow as irregular cellular conglomerates 201 (See FIGS. 35A and 35B, 36A and 36B), and create an inhomogeneous population of multicellular 3D structures in the vessel. In embodiments, a cell culture surface consisting essentially of a plurality of microcavities.

Figure 35B:
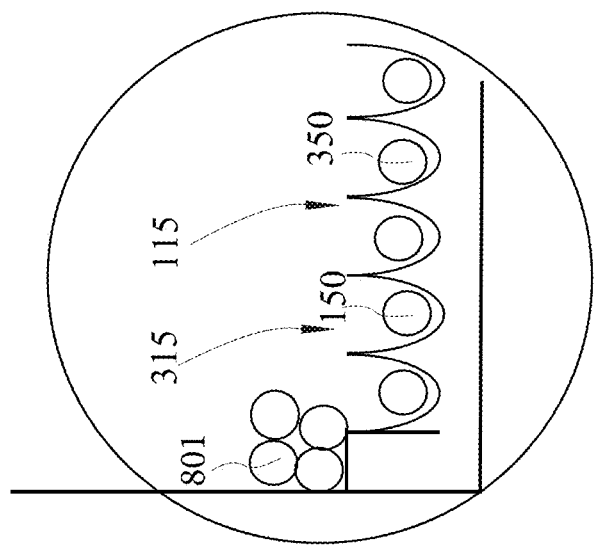
FIG. 35A and FIG. 35B are drawings illustrating cells growing as spheroids in microcavities and cells growing in irregular shapes on flat surfaces in a cell culture vessel.
Figure 35A:
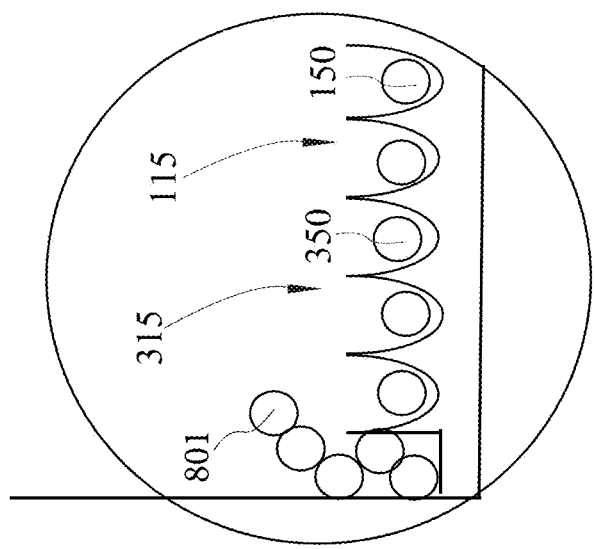

In some embodiments, cells that settle on or adhere to a surface of the vessel 300 can accumulate and grow (e.g., multiply) outside of the microcavities 320a, 320b, 320c causing problems with respect to desired growth of three-dimensional cells within the microcavities 320a, 320b, 320c. FIG. 35A and FIG. 35B are schematic drawings of cells accumulating in flat areas on the periphery of the microcavities. For example, in some embodiments, cells that do not fall (based at least on the force of gravity) into the well 322a, 322b, 322c and that accumulate or attach to other surfaces of the vessel 300 can grow outside of the well 322a, 322b, 322c. When cells settle outside of microwells, on flat areas outside the cell culture surface, cells can grow as irregular cellular conglomerates 801 which are undesirable. In addition, these irregular cellular conglomerates 801 can creep into neighboring microcavities and disrupt (e.g., discourage, alter, slow, or prevent) desired growth of three-dimensional cells within the well 322a, 322b, 322c. Similarly, in some embodiments, cells that accumulate or attach to other surfaces of the vessel 300 can grow and dislodge three-dimensional cells in the well 322a, 322b, 322c, thereby disrupting or destroying desired growth of three-dimensional cells within the well 322a, 322b, 322c and altering desired size uniformity of the cells. Accordingly, in some embodiments, by positioning at least a portion 331 of the outer perimeter 330 of the cell culture surface 315 in the recess 335 or on the protrusion 337, all cells suspended within the liquid can be directed into the wells 322a, 322b, 322c, thus reducing and eliminating problems that can otherwise occur if cells attach to surfaces of the vessel 300 outside the wells 322a, 322b, 322c.

Figure 30:
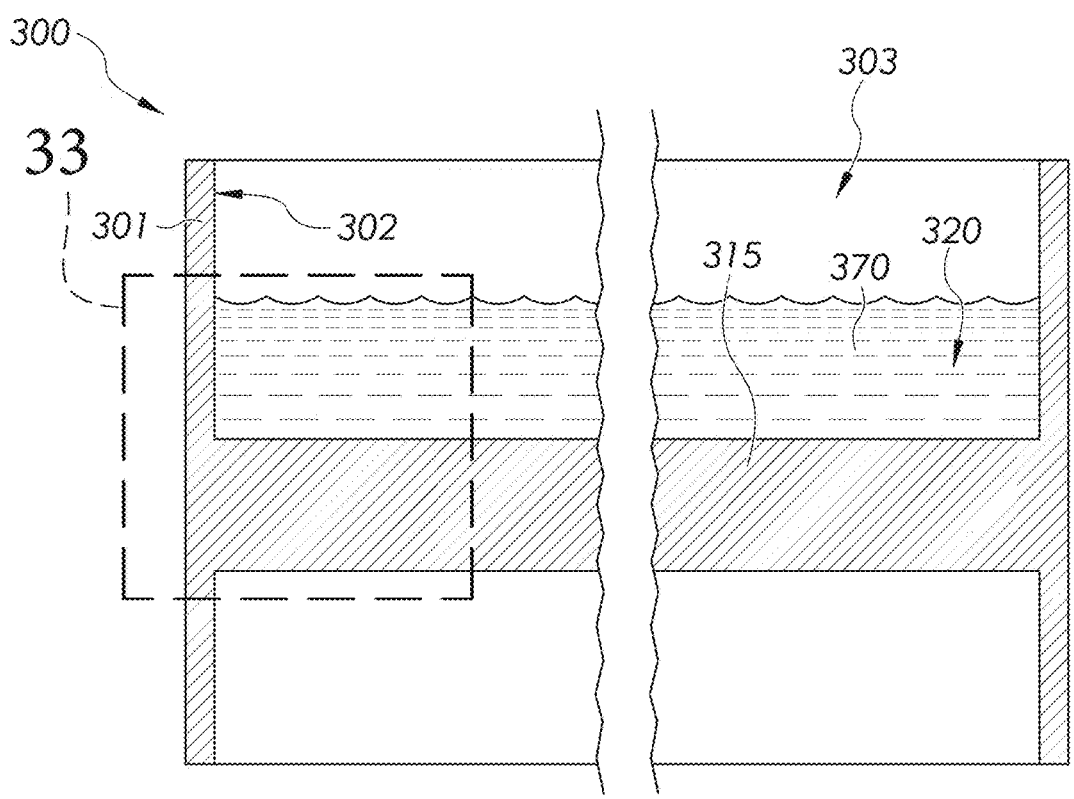
FIG. 30 is a cross-sectional view of a cell culture vessel of FIG. 19 including a predetermined amount of liquid in accordance with embodiments of the disclosure.
Figure 31:
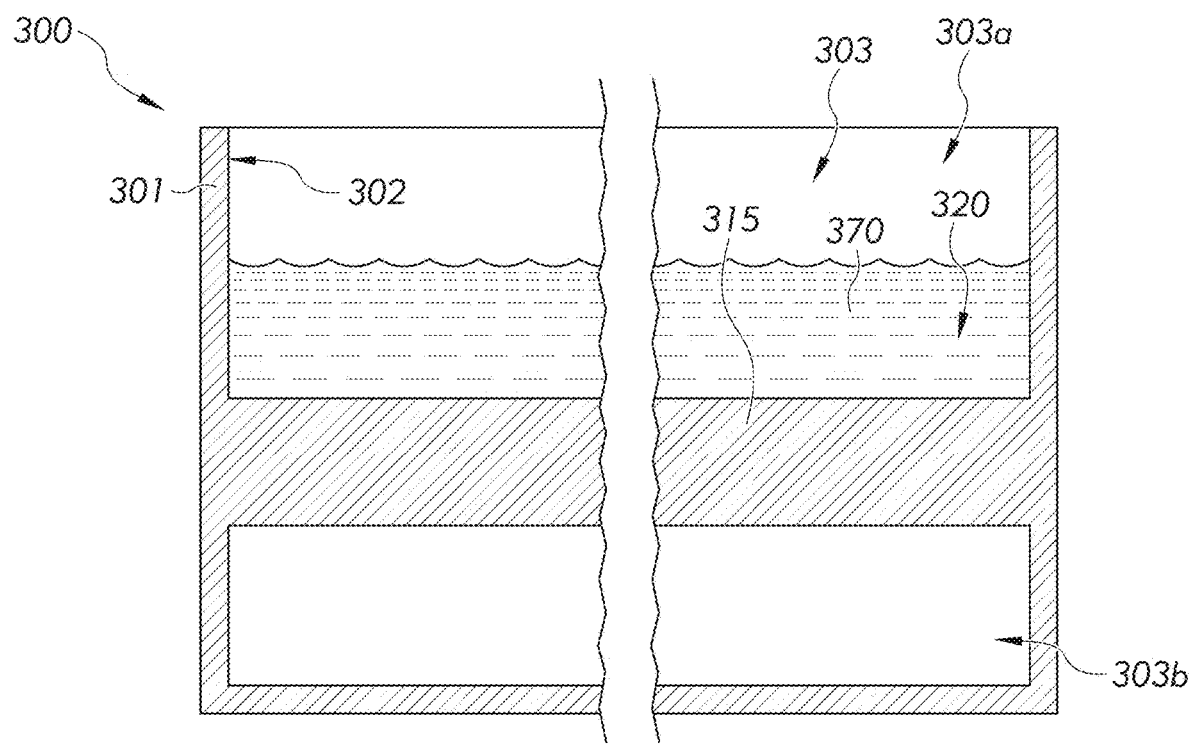
FIG. 31 is a cross-sectional view of a cell culture vessel including a predetermined amount of liquid of FIG. 30 in accordance with embodiments of the disclosure.

Another exemplary embodiment of the cell culture vessel 300 is shown in the cross-sectional view of FIG. 30. In some embodiments, the cell culture vessel 300 and the cell culture surface 315 can be manufactured from the same material. For example, in some embodiments, the cell culture surface 315 including the plurality of microcavities 320 can be manufactured (e.g., formed, machined, pressed, extruded, molded, printed by operation of 3D printing, etc.) as an integral part of the wall 301 of the vessel 300, such that there is no distinct boundary between the cell culture surface 315 and the wall 301 of the vessel 300. As shown in FIG. 30, in some embodiments, the cell culture surface 315 and the inner surface 302 of the wall 301 (integrally formed together) can define the cell culture chamber 303 of the vessel 300. Alternatively, as shown in FIG. 31, in some embodiments, the inner surface 302 of the wall 301 can define the cell culture chamber 303 of the vessel 300, including a first region 303a and a second region 303b, and the cell culture surface 315 (integrally formed with the wall 301) can be positioned in the cell culture chamber 303 between the first region 303a and the second region 303b. In some embodiments, the vessel 300 including the wall 301 and cell culture surface 315 integrally manufactured together can include a material that is non-permeable. Alternatively, in some embodiments (e.g., where the cell culture surface 315 is attached to the wall 301 of the vessel 300), the wall 301 of the vessel 300 can be manufactured from a non-permeable material, and the cell culture surface 315 can be manufactured from one or more of a non-permeable material, a non-porous material, a gas permeable material or a porous material, integrally formed with the wall 301.

In this embodiment, where the cell culture surface 315 and the wall 301 are manufactured as a single part, the cell culture surface 315 extends from wall 301 to wall 301. In embodiments, the cell culture surface 315 does not have any flat areas. That is, the cell culture surface is an array of microcavities 320 extending from wall to wall with no border, no flat areas between the cell culture surface and walls 301. In embodiments, the cell culture surface consisting essentially of a plurality of microcavities. In embodiments, there no flat areas in the cell culture chamber for cells to settle on. This is important to ensure that cells do not settle in the cell culture chamber outside of the microwells. When cells settle outside of microwells, on flat areas outside the cell culture surface, cells can grow as irregular cellular conglomerates 201 (See FIGS. 35A and 35B, 36A and 36B), and create an inhomogeneous population of multicellular 3D structures in the vessel. In embodiments, a cell culture surface consisting essentially of a plurality of microcavities.

Additionally, in some embodiments, the vessel 300 can include a predetermined amount of liquid 370, and a method of culturing cells in the cell culture vessel 300 can include depositing liquid 370 in at least one microcavity 320*a*, 320*b*, 320*c* of the plurality of microcavities 320 and culturing cells in the at least one microcavity 320*a*, 320*b*, 320*c* after depositing the liquid 370 in the at least one microcavity 320*a*, 320*b*, 320*c*.

As shown in FIG. 45, which shows an enlarged view of the integrally formed cell culture surface 315 and wall 301 of the vessel 300 at view 45 of FIG. 43, the predetermined amount of liquid 370 can contact submerged surfaces 325 of the vessel 300 and occupy a region of the cell culture chamber 303 of the vessel 300. FIG. 46, shows an alternate exemplary embodiment of FIG. 45, including features of the at least a portion 331 of the outer perimeter 330 of the cell culture surface 315 positioned in the recess 335 of the wall 301 of the vessel 300 with the predetermined amount of liquid contacting submerged surfaces 325 of the vessel 300, including the peripheral surface 332 of the cell culture surface 315, and occupying a region of the cell culture chamber 303 of the vessel 300. Similarly, FIG. 34, shows an alternate exemplary embodiment of FIG. 32, including features of the at least a portion 331 of the outer perimeter 330 of the cell culture surface 315 positioned on the protrusion 337 of the wall 301 of the vessel 300 with the predetermined amount of liquid 370 contacting submerged surfaces 325 of the vessel 300, including the peripheral surface 332 of the cell culture surface 315, and occupying a region of the cell culture chamber 303 of the vessel 300.

Figure 32:
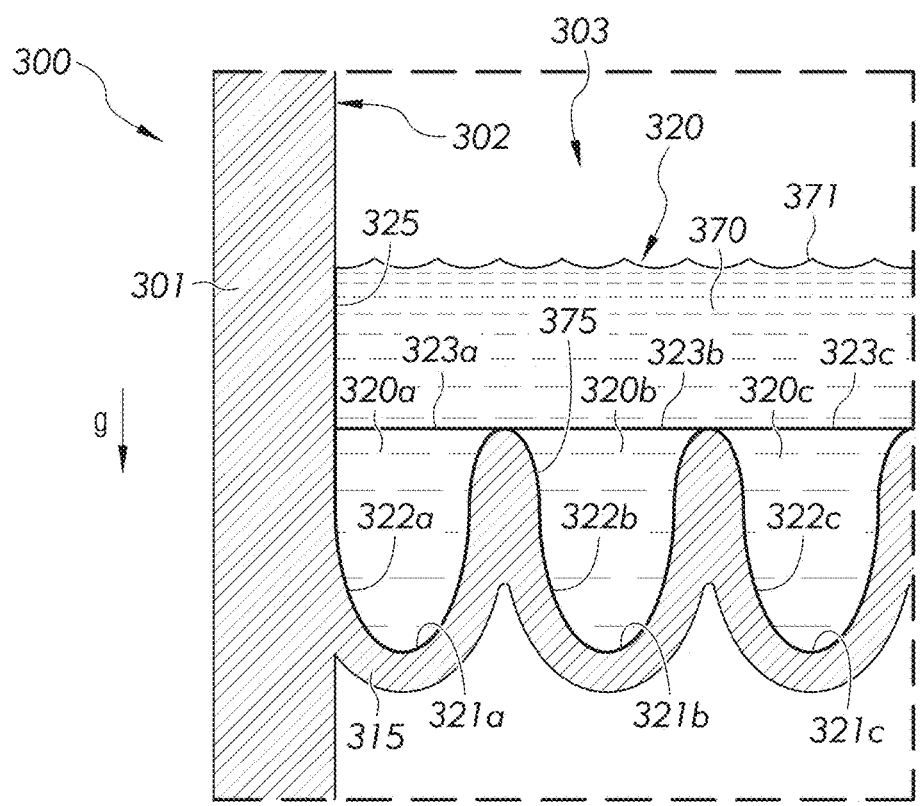
FIG. 32 is an enlarged schematic representation of an embodiment of a portion of the cell culture vessel taken at view 32 of FIG. 30 including submerged surfaces of the vessel in accordance with embodiments of the disclosure.
Figure 33:
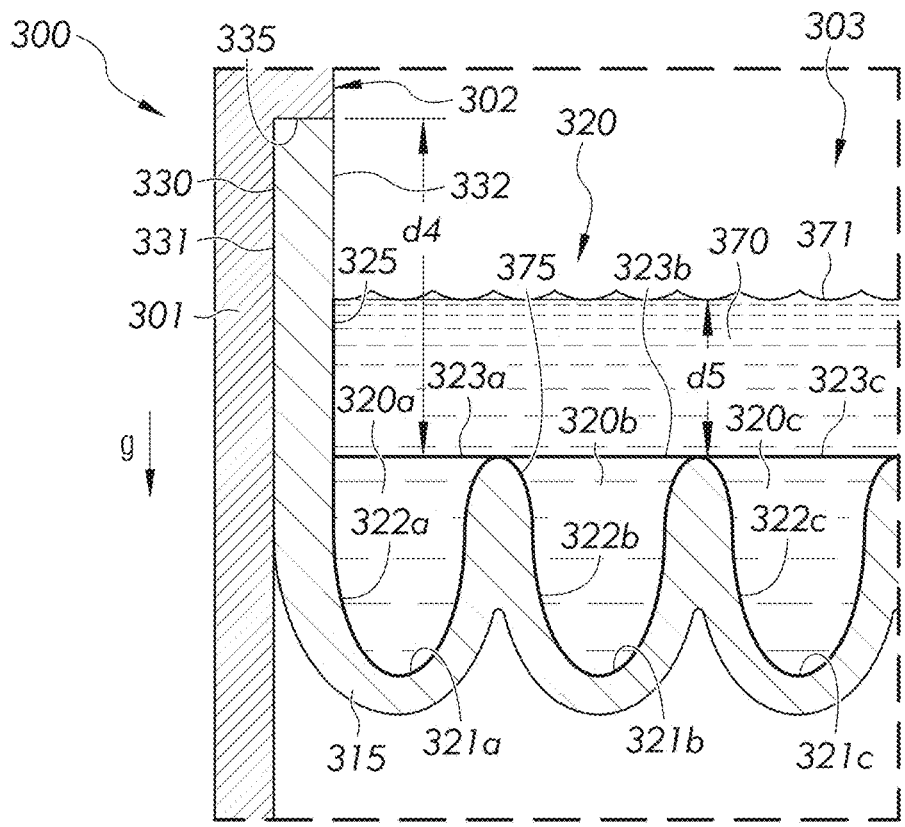
FIG. 33 shows an alternative embodiment of the portion of the cell culture vessel including submerged surfaces of the vessel of FIG. 32 including a recess in accordance with embodiments of the disclosure.
Figure 34:
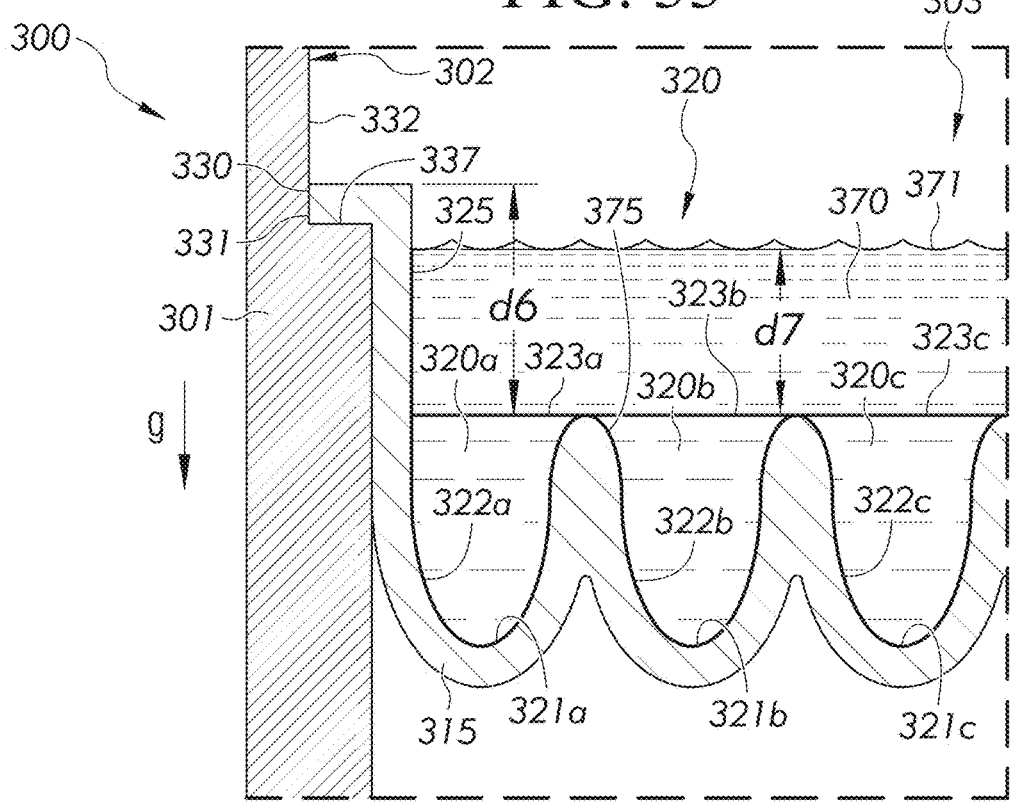
FIG. 34 shows an alternative exemplary embodiment of the portion of a cell culture vessel including submerged surfaces of the vessel of FIG. 32 including a protrusion in accordance with embodiments of the disclosure.

For illustrative purposes only, the submerged surfaces 325 are shown with thicker line weights in FIGS. 32-34 with the understanding that, in some embodiments, submerged surfaces 325 can include surfaces of the vessel 300 that are in contact with the predetermined amount of liquid 370. In some embodiments, the submerged surfaces 325 can be defined relative to the direction of gravity "g" at or during a specified step of a method of culturing cells in the vessel 300. For example, in some embodiments, the predetermined amount of liquid 370 can define a liquid level 371, where the submerged surfaces 325 include surfaces of the vessel 300 in contact with the predetermined amount of liquid 370 that are, relative to the direction of gravity "g", positioned below the liquid level 371 and, therefore, submerged in the predetermined amount of liquid 370. In some embodiments, the level 371 of the predetermined amount of liquid 370 can define a planar free surface of the predetermined amount of liquid 370 spaced a distance from a portion 375 of the cell culture surface 315. For example, the portion 375 of the cell culture surface 315 can include the openings 323*a*, 323*b*, 323*c* and the planar free surface defined by the liquid level 371 of the predetermined amount of liquid 370 can be spaced a distance from the portion 375 in a direction away from the concave surface 321*a*, 321*b*, 321*c* of each microcavity 320*a*, 320*b*, 320*c* of the plurality of microcavities 320.

Additionally, in some embodiments, the submerged surfaces 325 of the vessel 300 do not include planar surface portions parallel to the planar free surface of the predetermined amount of liquid 370. By providing submerged surfaces 325 that do not include planar surface portions parallel to the planar free surface of the level 371 of the predetermined amount of liquid 370, cells suspended in the liquid 370 will fall (e.g., based at least on the force of gravity) and/or be directed by the submerged surfaces 325 into the wells 322*a*, 322*b*, 322*c* of the microcavities 320*a*, 320*b*, 320*c* because there are no submerged surfaces 325 on which the cells can settle or to which the cells can adhere. As noted above, in some embodiments, cells that settle on or adhere to a surface of the vessel 300 can accumulate and grow (e.g., multiply) outside of the microcavities 320*a*, 320*b*, 320*c* causing problems with respect to desired growth of three-dimensional cells within the microcavities 320*a*, 320*b*, 320*c*. For example, in some embodiments, cells that do not fall (based at least on the force of gravity) into the well 322*a*, 322*b*, 322*c* and that accumulate or attach to other surfaces of the vessel 300 (e.g., if the submerged surfaces 325 were to include planar surface portions parallel to the planar free surface of the predetermined amount of liquid 370) can grow outside of the well 322*a*, 322*b*, 322*c* and disrupt (e.g., discourage, alter, slow, or prevent) desired growth of three-dimensional cells within the well 322*a*, 322*b*, 322*c*. Similarly, in some embodiments, if the submerged surfaces 325 were to include planar surface portions parallel to the planar free surface of the predetermined amount of liquid 370, cells could accumulate or attach to the planar surface portions and could grow and dislodge three-dimensional cells in the well 322*a*, 322*b*, 322*c*, thereby disrupting or destroying desired growth of three-dimensional cells within the well 322*a*, 322*b*, 322*c*. Accordingly, in some embodiments, by providing submerged surfaces 325 that do not include planar surface portions parallel to the planar free surface of the level 371 of the predetermined amount of liquid 370, all cells suspended within the liquid 370 can be directed into the wells 322*a*, 322*b*, 322*c*, thus reducing and eliminating problems that can otherwise occur if cells attach to surfaces of the vessel 300 outside the wells 322*a*, 322*b*, 322*c*.

As shown in FIG. 33, in some embodiments, at least a portion 331 of the outer perimeter 330 of the cell culture surface 315 can be spaced a distance "d4" from the portion 375 of the cell culture surface 315 in a direction away from the concave surface 321*a*, 321*b*, 321*c* of each microcavity 320*a*, 320*b*, 320*c* of the plurality of microcavities 320. Additionally, the cell culture surface 315 can include the peripheral surface 332 extending from the at least a portion 331 of the outer perimeter 330 to the portion 375 of the cell culture surface 315. In some embodiments, a depth "d5" of the predetermined amount of liquid 370 from the liquid level 371 defining the planar free surface to the portion 375 of the cell culture surface 315 along the direction can be less than the distance "d4". Likewise, as shown in FIG. 47, in some embodiments, at least a portion 331 of the outer perimeter 330 of the cell culture surface 315 can be spaced a distance "d6" from the portion 375 of the cell culture surface 315 in a direction away from the concave surface 321*a*, 321*b*, 321*c* of each microcavity 320*a*, 320*b*, 320*c* of the plurality of microcavities 320. The cell culture surface 315 can include the peripheral surface 332 extending from the at least a portion 331 of the outer perimeter 330 to the portion 375 of the cell culture surface 315. In some embodiments, a depth "d7" of the predetermined amount of liquid 370 from the liquid level 371 defining the planar free surface to the portion 375 of the cell culture surface 315 along the direction can be less than the distance "d6".

Accordingly, in some embodiments, by providing submerged surfaces 325 that do not include planar surface portions parallel to the planar free surface of the level 371 of the predetermined amount of liquid 370, alone or in combination with, a depth "d5" of the predetermined amount of liquid 370 from the liquid level 371 defining the planar free surface to the portion 375 of the cell culture surface 315 along the direction can be less than the distance "d4" (e.g., FIG. 33, including the recess 335) and a depth "d7" of the predetermined amount of liquid 370 from the liquid level 371 defining the planar free surface to the portion 375 of the cell culture surface 315 along the direction can be less than the distance "d6" (e.g., FIG. 34, including the protrusion 337), all cells suspended within the liquid 370 can be directed into the wells 322a, 322b, 322c, thus reducing and eliminating problems that can otherwise occur if cells attach to surfaces of the vessel 300 outside the wells 322a, 322b, 322c. Moreover, although not explicitly illustrated, in some embodiments, a method of culturing cells (See FIG. 16) in the vessel 300 can include depositing a portion of the predetermined amount of liquid 370 in at least one microcavity 320a, 320b, 320c of the plurality of microcavities 320a, 320b, 320c; and culturing cells in the at least one microcavity 320a, 320b, 320c after depositing the portion of the predetermined amount of liquid 370 in the at least one microcavity 320a, 320b, 320c.

Referring to FIGS. 32-34, in some embodiments, a method of culturing cells in the cell culture vessel 300 can include filling a region of a cell culture chamber 303 of the vessel 300 with a predetermined amount of liquid 370. In some embodiments, the cell culture chamber 303 can be defined at least in part by an inner surface 302 of the wall 301 of the vessel 300, and the method can include depositing a portion of the predetermined amount of liquid 370 in at least one microcavity 320a, 320b, 320c of the plurality of microcavities 320 of the cell culture surface 315. The cell culture surface 315 can define at least a portion 331 of the region, and each microcavity 320a, 320b, 320c of the plurality of microcavities 320 can include a concave surface 321a, 321b, 321c defining a well 322a, 322b, 322c and an opening 323a, 323b, 323c in a portion 375 of the cell culture surface 315 defining a path into the well 322a, 322b, 322c. In some embodiments, the method can further include culturing cells in the at least one microcavity 320a, 320b, 320c after depositing the portion of the predetermined amount of liquid 370 in the at least one microcavity 320a, 320b, 320c, with the predetermined amount of liquid 370 contacting submerged surfaces 325 of the vessel 300. In some embodiments, while culturing the cells in the at least one microcavity 320a, 320b, 320c, the submerged surfaces 325 do not include planar surface portions including a surface normal that is opposite the direction of gravity "g". Optionally, in some embodiments, while culturing the cells in the at least one microcavity 320a, 320b, 320c of the plurality of microcavities 320, a level 371 of the predetermined amount of liquid 370 can define a planar free surface of the predetermined amount of liquid 370 that is perpendicular relative to the direction of gravity "g".

By providing submerged surfaces 325 that do not include planar surface portions including a surface normal that is opposite the direction of gravity "g", cells suspended in the liquid 370 will fall (e.g., based at least on the force of gravity) and/or be directed by the submerged surfaces 325 into the wells 322a, 322b, 322c of the microcavities 320a, 320b, 320c because there are no submerged surfaces 325 on which the cells can settle or to which the cells can adhere. As noted above, in some embodiments, cells that settle on or adhere to a surface of the vessel 300 can accumulate and grow (e.g., multiply) outside of the microcavities 320a, 320b, 320c causing problems with respect to desired growth of three-dimensional cells within the microcavities 320a, 320b, 320c. For example, in some embodiments, cells that do not fall (based at least on the force of gravity) into the well 322a, 322b, 322c and that accumulate or attach to other surfaces of the vessel 300 (e.g., if the submerged surfaces 325 were to include planar surface portions including a surface normal that is opposite the direction of gravity "g") can grow outside of the well 322a, 322b, 322c and disrupt (e.g., discourage, alter, slow, or prevent) desired growth of three-dimensional cells within the well 322a, 322b, 322c. Similarly, in some embodiments, if the submerged surfaces 325 were to include planar surface portions including a surface normal that is opposite the direction of gravity "g", cells could accumulate or attach to the planar surface portions and could grow and dislodge three-dimensional cells in the well 322a, 322b, 322c, thereby disrupting or destroying desired growth of three-dimensional cells within the well 322a, 322b, 322c. Accordingly, in some embodiments, by providing submerged surfaces 325 that do not include planar surface portions including a surface normal that is opposite the direction of gravity "g", all cells suspended within the liquid 370 can be directed into the wells 322a, 322b, 322c, thus reducing and eliminating problems that can otherwise occur if cells settle on or attach to surfaces of the vessel 300 outside the wells 322a, 322b, 322c.

Moreover, for purposes of the disclosure, unless other noted, "planar surface portion" is intended to mean any planar surface portion including a planar dimension greater than about 5 microns. For example, in some embodiments, submerged surfaces 325 that do not include planar surface portions parallel to the planar free surface of the level 371 of the predetermined amount of liquid 370 can be defined as submerged surfaces 325 that do not include planar surface portions, including a planar dimension greater than about 5 microns, parallel to the planar free surface of the level 371 of the predetermined amount of liquid 370. Similarly, in some embodiments, submerged surfaces 325 that do not include planar surface portions including a surface normal that is opposite the direction of gravity "g" can be defined as submerged surfaces 325 that do not include planar surface portions, including a planar dimension greater than about 5 microns, including a surface normal that is opposite the direction of gravity "g".

For example, in some embodiments, the submerged surfaces 325 can include a planar portion; however, if a planar dimension of the planar surface portion is, for example, less than or equal to 5 microns, in some embodiments, the planar surface portion is considered too small for cells to reasonably accumulate or attach. Accordingly, in some embodiments, by providing submerged surfaces 325 that do not include planar surface portions including a planar dimension greater than about 5 microns, all cells suspended within the liquid 370 can be directed into the wells 322a, 322b, 322c, thus reducing and eliminating problems that can otherwise occur if cells settle on or attach to surfaces of the vessel 300 outside the wells 322a, 322b, 322c. In some embodiments, however, the submerged surfaces 325 can be entirely free of planar surface portions, irrespective of a threshold dimension defining the planar surface portion.

FIG. 35A and FIG. 35B are drawings illustrating cells growing as spheroids in microcavities and cells growing as irregular cellular conglomerates 201. These irregular cellular conglomerates can occur in the embodiments shown in FIG. 1-16 (cell culture surface 115) or in the embodiments shown in FIG. 17-34 (cell culture surface 315), where flat surfaces occur in a vessel. It is important to avoid flat surfaces in the cell culture chamber 103 or 303, to avoid these irregular cellular conglomerates.

Figure 36A:
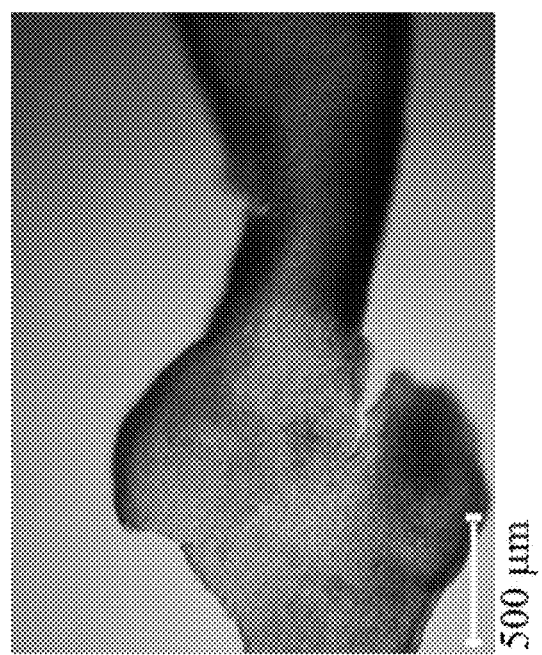
FIG. 36A is a photograph of spheroids in an array of microcavities.
Figure 36B:
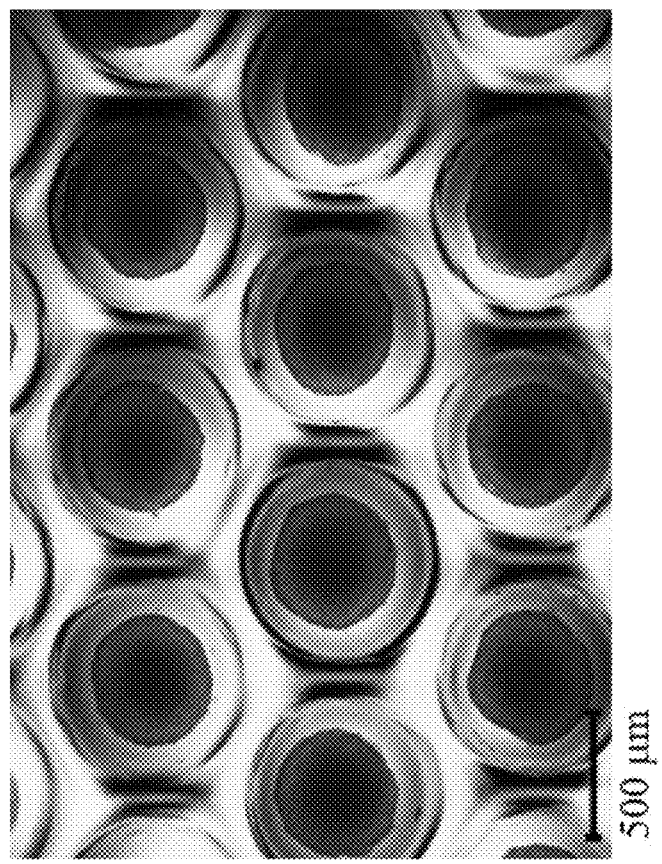
FIG. 36B is a photograph of cells growing in irregular cellular conglomerates.

FIG. 36A is a photograph of spheroids in an array of microcavities under suitable conditions provide a homogeneous population of spheroids in the vessel. FIG. 36B is a photograph of irregular cellular conglomerates 801 isolated from a vessel having flat surfaces in the cell growth chamber 103, 303. To avoid producing these irregular cellular conglomerates 801, embodiments of a cell culture vessel are provided which do not have flat surfaces in the cell culture surface, or do not have flat surfaces in the submerged region of the cell culture surface. That is, in embodiments of a cell culture vessel, the cell culture surface consists essentially of an array of microcavities, and does not provide flat surfaces that can produce undesirable irregular cellular conglomerates 801.

Throughout the disclosure, the terms "material", "liquid", and "gas" can be used to describe properties of a material employed when, for example, culturing cells in the cell culture vessel. Unless otherwise noted, for purposes of the disclosure, "material" can include fluid material (e.g., liquid or gas). Additionally, material can include a culture solution or media including a liquid including solid particles (e.g., cells) suspended in the liquid. Unless otherwise noted, for purposes of the disclosure, "liquid" can include cleaning or rinsing solutions, aqueous solutions, or other liquid that can be added to or removed from the vessel to, for example, clean the cell culture chamber, sterilize one or more features of the cell culture surface and the vessel, prepare the cell culture surface for cellular growth and other uses of liquid. Additionally, liquid can include a culture solution or media including a liquid including solid particles (e.g., cells) suspended in the liquid. Unless otherwise noted, for purposes of the disclosure, "gas" can include air, filtered or treated air, or other gases.

Throughout the disclosure, the terms "non-permeable", "gas-permeable", and "porous" can be used to describe properties (e.g., material properties, characteristics, parameters) of one or more features of a cell culture surface.

Unless otherwise noted, for purposes of the disclosure, a "non-permeable" cell culture surface (e.g., material of a non-permeable cell culture surface) is considered to be impermeable to solid, liquid, and gas under normal conditions (e.g., no external influence including but not limited to pressure and force) and, therefore, does not permit the transfer of solid, liquid, or gas in to, through, or out of, the non-permeable cell culture surface under normal conditions. In some embodiments, a non-permeable cell culture surface can form a portion of the wall of the vessel. Additionally, the cell culture chamber of the vessel is considered to be sterile when a non-permeable cell culture surface forms a portion of the wall of the vessel because bacteria, for example, cannot pass through the non-permeable cell culture surface. However, when filling the plurality of microcavities of the cell culture surface with material, gas can become trapped within the microcavity of a non-permeable cell culture surface based on surface tension of the liquid, thereby, in some embodiments, preventing material from filling the microcavities and preventing growth of a spheroid.

Unless otherwise noted, for purposes of the disclosure, a "gas-permeable" cell culture surface (e.g., material of a gas-permeable cell culture surface) is considered to be impermeable to solid and liquid, and permeable to gas under normal conditions. Therefore, a gas-permeable cell culture surface does not permit the transfer of solid and liquid in to, through, or out of, the gas-permeable cell culture surface and does permit the transfer of gas in to, through, or out of, the gas-permeable cell culture surface. In some embodiments, a gas-permeable cell culture surface can form a portion of the wall of the vessel. Additionally, the cell culture chamber of the vessel is considered to be sterile when a gas-permeable cell culture surface forms a portion of the wall of the vessel because bacteria, for example, cannot reasonably pass through the gas-permeable cell culture surface. However, although the cell culture surface is gas-permeable, gas can still become trapped in the microcavity during filling with material because gas-permeation rates through the gas-permeable cell culture surface can be slower than the rate required to displace gas from the cavity under ordinary operating conditions and can therefore take an unacceptably long amount of time to permeate through the cell culture surface. Thus, in some embodiments, slowly filling the microcavities allows the liquid front to enter each microcavity at an angle, thereby displacing gas as the liquid fills the microcavity. In some embodiments, after filling the cavity with liquid, gas can permeate (slowly) through the gas-permeable cell culture surface.

Unless otherwise noted, for purposes of the disclosure, a "porous" cell culture surface (e.g., material of a porous cell culture surface) is considered to be impermeable to solid and permeable to liquid and gas under normal conditions. Therefore, a porous cell culture surface does not permit the transfer of solid in to, through, or out of, the porous cell culture surface and does permit the transfer of liquid and gas in to, through, or out of, the porous cell culture surface. A porous cell culture surface cannot form a portion of the vessel because bacteria can pass through a porous cell culture surface, thus causing sterility issues in the cell culture chamber. Thus, when using a porous cell culture surface, the cell culture surface must be enclosed (entirely enclosed) in the sterile cell culture chamber of the vessel. During filling of the microcavities with material, however, gas can escape (e.g., pass) through the porous cell culture surface. Thus, filling of the microcavities can be performed rapidly without concern for entrapping gas in the microcavities. In some embodiments, liquid can only pass through the porous cell culture surface with added pressure or physical contact and disturbance of the cell culture surface. Thus, in some embodiments, material including liquid can be contained in the microcavities of the cell culture surface so long as the cell culture surface is not exposed to added pressure or physical contact and disturbance. For example, in some embodiments, the porous cell culture surface can be supported in the cell culture chamber to allow gas to pass through the cell culture surface during filling as well as during culturing and to isolate the cell culture surface from added pressure or physical contact and disturbance from external forces (e.g., outside the cell culture chamber).

A number of aspects of cell culture vessels and methods of culturing cells have been disclosed herein. A summary of some selected aspects is presented below.

In a first aspect, the disclosure provides a cell culture vessel comprising: a cell culture surface consisting essentially of a plurality of microcavities; a wall attached to the cell culture surface, the cell culture surface and an inner surface of the wall define a cell culture chamber of the vessel.

In a second aspect, the disclosure provides the cell culture vessel of aspect 1, each microcavity of the plurality of microcavities comprises a concave bottom and an opening.

In a third aspect, the disclosure provides the cell culture vessel of aspect 1 or 2, further comprising a necked opening.

In a fourth aspect, the disclosure provides the cell culture vessel of aspect 3 further comprising and dam in the necked opening.

In a fifth aspect, the disclosure provides the cell culture vessel of aspect 1 or 2 further comprising a lid.

In a sixth aspect, the disclosure provides the cell culture vessel of aspect 3 or 4 further comprising a lid.

In a seventh aspect, the disclosure provides the cell culture vessel of aspect 6 wherein the lid comprises a hinged opening.

In an eighth aspect, the disclosure provides the cell culture vessel of aspect 4 wherein the lid comprises a sliding opening.

In a ninth aspect, the disclosure provides the cell culture vessel of aspect 3, 4, or 6-8 wherein the necked opening comprises a bend.

In a tenth aspect, the disclosure provides the cell culture vessel of any one of aspects 1-9 wherein the wall comprises a recess and the cell culture surface is attached to the recess.

In an eleventh aspect, the disclosure provides the cell culture vessel of any one of aspects 1-9 wherein the wall comprises a protrusion and the cell culture surface is attached to the protrusion.

In a twelfth aspect, the disclosure provides a cell culture vessel comprising: a cell culture surface comprising a plurality of microcavities, the microcavities having a non-flat sinusoidal shape; a wall attached to the cell culture surface, the cell culture surface and an inner surface of the wall define a cell culture chamber of the vessel; wherein the cell culture surface is substantially free of flat areas.

In a thirteenth aspect, the disclosure provides the cell culture vessel of aspect 12, each microcavity of the plurality of microcavities comprises a concave bottom and an opening.

In a fourteenth aspect, the disclosure provides the cell culture vessel of aspect 12 or 13, further comprising a necked opening.

In a fifteenth aspect, the disclosure provides the cell culture vessel of aspect 14 further comprising and dam in the necked opening.

In a sixteenth aspect, the disclosure provides the cell culture vessel of aspect 12 or 13 further comprising a lid.

In a seventeenth aspect, the disclosure provides the cell culture vessel of aspect 14 or 15 further comprising a lid.

In an eighteenth aspect, the disclosure provides the cell culture vessel of aspect 17 wherein the lid comprises a hinged opening.

In a nineteenth aspect, the disclosure provides the cell culture vessel of aspect 17 wherein the lid comprises a sliding opening.

In a twentieth aspect, the disclosure provides the cell culture vessel of any one of aspects 14, 15, or 17-19 wherein the necked opening comprises a bend.

In a twenty-first aspect, the disclosure provides the cell culture vessel of any one of aspects 12-17 wherein the wall comprises a recess and the cell culture surface is attached to the recess.

In a twenty-second aspect, the disclosure provides the cell culture vessel of any one of claims 12-17 wherein the wall comprises a protrusion and the cell culture surface is attached to the protrusion.

It will be appreciated that the various disclosed embodiments can involve particular features, elements or steps that are described in connection with that particular embodiment. It will also be appreciated that a particular feature, element or step, although described in relation to one particular embodiment, can be interchanged or combined with alternate embodiments in various non-illustrated combinations or permutations.

It is to be understood that, as used herein the terms "the," "a," or "an," mean "at least one," and should not be limited to "only one" unless explicitly indicated to the contrary. Thus, for example, reference to "a component" includes embodiments having two or more such components unless the context clearly indicates otherwise.

Ranges can be expressed herein as from "about" one particular value, and/or to "about" another particular value. When such a range is expressed, embodiments include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments can be disclosed using the transitional phrase "comprising," it is to be understood that alternative embodiments, including those that can be described using the transitional phrases "consisting" or "consisting essentially of," are implied. Thus, for example, implied alternative embodiments to an apparatus that comprises A+B+C include embodiments where an apparatus consists of A+B+C and embodiments where an apparatus consists essentially of A+B+C.

It will be apparent to those skilled in the art that various modifications and variations can be made to the present disclosure without departing from the spirit and scope of the disclosure. Thus, it is intended that the present disclosure cover the modifications and variations of this disclosure provided they come within the scope of the appended claims and their equivalents.

What is claimed is:

1. A cell culture vessel comprising:
   a cell culture surface comprising a plurality of microcavities, wherein a first side of the cell culture surface comprises a non-flat sinusoidal shape;
   a wall attached to the cell culture surface, wherein the cell culture surface and an inner surface of the wall define a cell culture chamber of the vessel; and
   a necked opening;
   wherein the cell culture surface is substantially free of flat areas; and
   wherein the necked opening comprises an inner surface and a bend, the bend having an obtuse angle on a bottom portion of the inner surface and the bend having a location higher than the cell culture surface when the cell culture surface is approximately perpendicular to the direction of gravity.

2. The cell culture vessel of claim 1, each microcavity of the plurality of microcavities comprises a concave bottom and an opening.

3. The cell culture vessel of claim 1, further comprising a dam in the necked opening.

4. The cell culture vessel of claim 3, further comprising a lid.

5. The cell culture vessel of claim 4, wherein the lid comprises a hinged opening.

6. The cell culture vessel of claim 4, wherein the lid comprises a sliding opening.

7. The cell culture vessel of claim 1, further comprising a lid.

8. The cell culture vessel of claim 1, wherein the wall comprises a recess and the cell culture surface is attached to the recess.

9. The cell culture vessel of claim 1, wherein the wall comprises a protrusion and the cell culture surface is attached to the protrusion.

10. The cell culture vessel of claim 1, wherein the cell culture surface comprises a second side and the second side comprises a non-flat sinusoidal shape.

\* \* \* \* \*